(12) United States Patent
Lee

(10) Patent No.: US 9,498,463 B2
(45) Date of Patent: *Nov. 22, 2016

(54) COMPOUND OBTAINED FROM GAMBOGE RESIN, AND MEDICAL USES OF THE SAME

(75) Inventor: Sen-Bin Lee, Tauyuan (TW)

(73) Assignee: Taiwan Sunpan Biotechnology Development Co., Ltd., Tauyuan (TW)

( * ) Notice: Subject to any disclaimer, the term of this patent is extended or adjusted under 35 U.S.C. 154(b) by 814 days.

This patent is subject to a terminal disclaimer.

(21) Appl. No.: 13/068,716

(22) Filed: May 17, 2011

(65) Prior Publication Data

US 2011/0306658 A1 Dec. 15, 2011

(30) Foreign Application Priority Data

Jun. 11, 2010 (TW) .............................. 99119107 A

(51) Int. Cl.
| | |
|---|---|
| A61K 31/35 | (2006.01) |
| A61K 31/20 | (2006.01) |
| A61K 31/352 | (2006.01) |
| C07D 493/22 | (2006.01) |
| A61K 36/38 | (2006.01) |

(52) U.S. Cl.
CPC ............ *A61K 31/352* (2013.01); *A61K 36/38* (2013.01); *C07D 493/22* (2013.01)

(58) Field of Classification Search
CPC .... A61K 31/352; A61K 31/35; A61K 31/20; C07D 493/22
USPC .......................... 514/453, 559; 549/384, 381
See application file for complete search history.

(56) References Cited

U.S. PATENT DOCUMENTS

| | | |
|---|---|---|
| 6,462,041 B1 | 10/2002 | Cai et al. |
| 7,138,428 B2 | 11/2006 | Lee et al. |
| 2005/0261363 A1 | 11/2005 | Lee et al. |
| 2007/0093456 A1 | 4/2007 | Cai et al. |
| 2007/0149610 A1 | 6/2007 | Han et al. |
| 2011/0306658 A1* | 12/2011 | Lee .............................. 514/450 |

FOREIGN PATENT DOCUMENTS

| | | |
|---|---|---|
| CN | 1391892 A | 1/2003 |
| CN | 1699368 A | 11/2005 |
| CN | 1245407 C | 3/2006 |
| CN | 1289505 C | 12/2006 |
| CN | 1927861 A | 3/2007 |
| CN | 100413868 C | 8/2008 |
| EP | 1 619 195 A2 | 1/2006 |
| EP | 2395007 A1 | 12/2011 |
| JP | 2005-330261 A | 12/2005 |
| JP | 5441947 B2 | 3/2014 |
| TW | 200538140 A | 12/2005 |
| TW | I282280 B | 6/2007 |

OTHER PUBLICATIONS

Cheng et al, antitumor effects of neogambogic acid in vivo and vitro, 2008, Zhongcaoyao, 39(2), p. 236-240, (an abstract page).*

(Continued)

*Primary Examiner* — T. Victor Oh
(74) *Attorney, Agent, or Firm* — Quine IP Law Group

(57) ABSTRACT

Disclosed herein are seventeen new compounds obtained from an acetone-extracted product of gamboge resin. The seventeen new compounds have activities in inhibiting the growth of tumor/cancer cells.

1 Claim, 5 Drawing Sheets

(56) References Cited

OTHER PUBLICATIONS

Feng et al, Anti-tumor QSAR of gambogic acid analogues, Zhongguo Yao Daxue Xuebao , 2007, 38(4), p. 311-314 , (one abstract page ).*
Kong et al. (1996) "Studies on the Acute Toxicity and Anti-inflammatory Effect of Processed Products of Gamboge," China Journal of Chinese Materia Medica, 4(21):214-216 with English translation (4 pages).
Asano et al. (1996) "Cytotoxic Xanthones From Garcinia Hanburyi." *Phytochemistry*, 41(3): 815-820.
European Search Report, dated Oct. 10, 2011, for EP application No. 11167255.6.
Han et al. (2006) "Cytotoxic Polyprrenylated Xanthones from the Resin of Garcinia hanburyi," *Chem. Pharm Bull.*, 54(2): 265-267.
Hong et al. (2008) "Studies of Chemical Constituents of Gamboage," *Chin Pham J*, 43(12): 1001-2494. (Abstract Only).
Ming-Mei et al. (2008) "Chemical Constitutes of Garcinia Hanburyi," *ACTA Chemica Sinca*, 22: 2513-2517. (English Abstract).
Panthong et al. (2007) "Anti-inflammatory, analgesic and anti-pyretic activities of the extract of gamboges from Garcinia hanburyi Hook f." Journal of Ethnopharmacology, 111: 335-340.
Ren et al. (2010) "Proteasome-inhabitory and cytotoxic constituents of Garcinia lateriflora: absolute configuration of caged xanthones." *Tetrahedron*, 66: 53311-5320.
Tao et al. (2009) "Cytotoxic Polyprenylated Xanthones from the Resin fo Garcinia hanburyi," *Journal of Natural Products*, 72(1): 117-124.
Wang et al. (2010) "Studies on chemical modification and biology of a natural product, gambogic acid (II): Synthesis and bioevaluation of gambogellic acid and its derivatives from gambogic acid and antitumor agents." *European Journal of Medical Chemistry*, 45: 4343-4353.
Feng et al. (2007) "Anti-tumor QSAR of gambogic acid analogues," *Journal of China Pharmaceutial University*, 38(4): 311-314.
Search Report for Chinese Application No. CN201010204256.6 (with English Translation).
Weng et al. (2008) "A new cytotoxic caged polyprenylated xanthone from the resin of Garcinia hanburyi," *Chinese Chemical Letters*, 19: 1221-1223.
Kong et al. (1996) "Studies on the Acute Toxicity and Anti-inflammatory Effect of Processed Products of Gamboge," China Journal of Chinese Materia Medica, 4(21):214-215 with English abstract (1 page).
Search Report dated Aug. 8, 2012 from TW application No. 099119107 (1 page) and English translation (1 page).
Search Report dated Feb. 21, 2013 from CN application No. 201010204256.6 (2 pages) and English translation (2 pages).
Wang et al. (2005) "Reversal of full-length mutant huntingtin neuronal cell phenotype by chemical inhibitors of polyglutamine-mediated aggregation," BMC Neuroscience, 6:1-12.
Wang et al. (2009) "Studies on chemical structure and biology of a natural product, gambogic acid (I): Synthesis and biological evaluation of oxidized analogues of gambogic acid," European Journal of Medical Chemistry, 44:2611-2620.
Jia, et al. (2008), "Chemical Constitutes of Garcinia hanburyi," *ACTA Chemica Sinica*, 66(22):2513-2517.
Office Action dated Nov. 17, 2014 and Search Report from CN 201310282342.2, including, English translation of Search Report.
Han, et al. (2006) "A pair of novel cytotoxic polyprenylated xanthone epimers from gamboges." *Chem Biodivers.*, 3(1):101-105.
I. j. Lin et al (1993) Isogambogic acid and isomorellinol from *Garcinia hanburyi magnetic resonance in chemistry*, 31:340-347.
Q.B. Han, 2006, *Planta Med.* 72:281-284.
Li, et al. (2008) "Improved high-performance liquid chromatographic method for simultaneous determination of 12 cytotoxic caged xanthones in gamboges, a potential anticancer resin from *Garcinia hanburyi*" *Biomed Chromatogr.*, 22(6):637-644.

* cited by examiner

COMPOUND OBTAINED FROM GAMBOGE RESIN, AND MEDICAL USES OF THE SAME

CROSS-REFERENCE TO RELATED APPLICATION

This application claims priority of Taiwanese Application No. 099119107, filed on Jun. 11, 2010.

BACKGROUND OF THE INVENTION

1. Field of the Invention

This invention relates to seventeen new compounds obtained from an acetone-extracted product of gamboge resin. The seventeen new compounds have been demonstrated to have activities in inhibiting the growth of tumor/cancer cells. Therefore, this invention also relates to the use of the seventeen new compounds in the preparation of pharmaceutical compositions.

2. Description of the Related Art

Gamboge resin is the gum-resin secreted by the plant of *Garcinia* sp. of the family Guttiferae. It has been used as a source of vegetative dyes and pigments since the old days. It is also used in folk medicine in some areas such as India and Thailand.

*Garcinia* (TENGHUANG in pinyin), which is commonly known as gamboge, is a kind of evergreen trees that grow in tropical regions. The main species grown in India is "*Garcinia morella* Desv," whereas the main species grown in Thailand is "*G. harburyi* Hook f." Before the flowering period, the bark of the tree is cut open in a spiral shape about 2 meters from the ground to collect the exuding resin. The resin is then subjected to heat-drying to result in a solidified gamboge resin.

According to traditional Chinese medicine (TCM), gamboge is effective in combating inflammations, clearing away toxins, stopping blood bleeding, and killing worms. Ever since 1934, there have been a number of reports on the components of the gamboge resin. At present, it is known that many compounds can be isolated from extracts of gamboge resin, including: morellin, morellic acid, gambogic acid, morellinol, isomorellin, isomorellic acid, isogambogic acid, isomorellinol, neogambogic acid, desoxymorellin, dihydroisomorellin, α-guttiferin, β-guttiferin, gambogenic acid, desoxygambogenin, gambogellic acid, epigambogic acid, epiisogambogic acid, isogambogenic acid, 30-hydroxygambogic acid, etc.

Some studies have reported the cytotoxic activity of certain components of gamboge resin on human cervical cancer cells HeLa, human nasopharyngeal cancer cells KB, human leukemia cells K562, and doxorubicin-resistant K562 cell lines, etc. (J. Asano et al. (1996), *Phytochemistry*, 41:815-820; L. J. Lin et al. (1993), *Magnetic Resonance in Chemistry*, 31:340-347; Q. B. Han et al. (2006), *Planta Med.*, 72:281-284; Q. B. Han et al. (2006), *Chem. Pharm. Bull.*, 54:265-267; Q. B. Han et al. (2006), *Chemistry & Biodiversity*, 3:101-105).

U.S. Pat. No. 6,462,041 B1 has disclosed gambogic acid and its analogs and derivatives as represented by the following Formulae I, II and III:

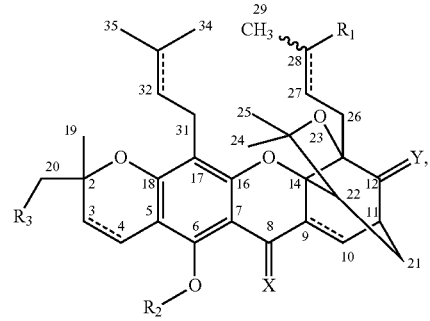

(I)

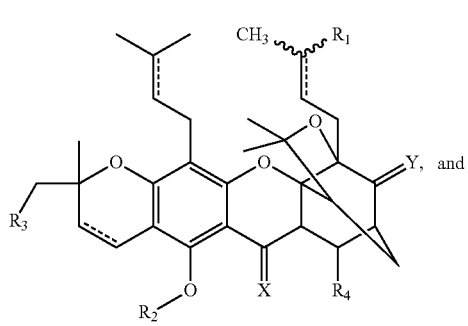

(II)

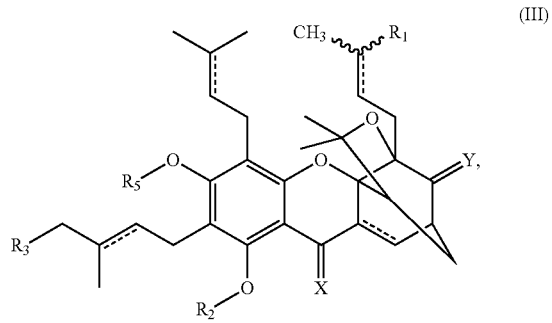

(III)

wherein a dash line denotes a single bond, a double bond, or an epoxy group; and X, Y, and $R_1$ to $R_3$ have the definitions as disclosed in said US patent.

Compounds having one of the aforesaid Formulae I-III are disclosed to be activators of caspases and inducers of apoptosis. However, U.S. Pat. No. 6,462,041 B1 has disclosed neither a compound of Formula I that has a 32,33-epoxy group, nor a process for preparing the same.

In Acta *Chimica Sinica*, 2008, 66(22):2513-2517, Ming-Meia Jia et al., studied the chemical components of *Garcinia hanburyi* and isolated fifteen compounds from the cold ethanol-extracted product of *Garcinia hanburyi* via silica gel column chromatography (gradient elution solvent system: petroleum ether-acetone, acetone, methanol) and preparative HPLC. According to structure identification, the fifteen compounds were identified as 2α-hydroxy-3β-acetoxy-lup-20(29)-en-28-oic acid (1), 10α-hydroxyepigambogic acid (2), gambogic acid (3), isogambogic acid (4), gambogin (5), gambogoic acid B (6), desoxymorellin (7), isomorellin (8), gambogenic acid (9), isogambogenin (10), gambogellic acid (11), desoxygambogenin (12), morellic acid (13), isomorellic acid (14), and 30-hydroxygambogic acid (15).

U.S. Pat. No. 7,138,428 B2 (corresponding to TW I282280 and CN 100413868 C) has disclosed an acetone-extracted product from gamboge resin, i.e., TSB-14. In addition, nine compounds were further purified from said acetone-extracted product TSB-14, including a new compound formoxanthone A, and eight known compounds betulin, betulinic acid, morellic acid, isomorellic acid, gambogic acid, isogambogic acid, isomorellinol and desoxymorellin.

The acetone-extracted product TSB-14 and the nine purified compounds have been demonstrated to have effects in inhibiting the growth of tumor/cancer cells such as liver cancer cells (HepG2), lung cancer cells (A549), breast cancer cells (MCF-7), colon cancer cells (HT-29), leukemia cells (HL-60), and lymphoma cancer cells (U937).

US 2007/0093456 A1 has disclosed a derivative of gambogic acid, which is identified as "methyl 37,38-dihydroxy-gambogate" and has the following chemical structure:

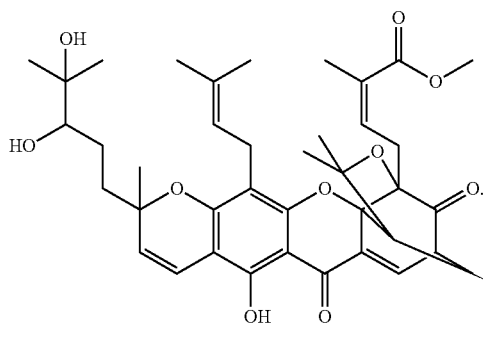

(methyl 37,38-dihydroxy-gambogate)

It has been found from experiments that methyl 37,38-dihydroxy-gambogate can act as an activator of caspases and an inducer of apoptosis.

In *Journal of Natural Products* (2009), 72:117-124, S. J. Tao et al. reported that twelve new xanthones (such as oxygambogic acid shown below, methyl 8,8a-dihydromorellate, 7-methoxygambogellic acid, etc.) and a pair of new natural products (i.e., 8,8a-dihydro-8-hydroxygambogic acid and its isomer) were isolated from the resin of *G. hanbury*.

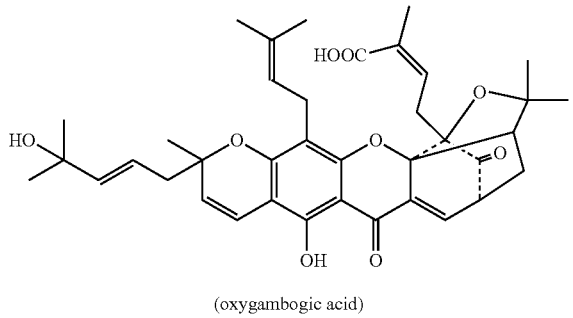

(oxygambogic acid)

The stereostructure of oxygambogic acid has yet to be confirmed since the configuration of the $C_{15}/C_{16}$ double bond could not be determined due to the overlapping of the H-15 and H-16 signals in the $^1$H-NMR spectral data. S. J. Tao et al. further found from pharmacological experiments that in addition to methyl 8,8a-dihydromorellate, all of the other tested thirteen compounds were effective in inhibiting the growth of HeLa cancer cells.

In addition to the activities in inhibiting the growth of tumor/cancer cells, the extracts of gamboge resin have been demonstrated to have other biological activities. For instance, in the report of A. Panthong et al. *Journal of Ethnopharmacology* (2007), 111:335-340, an ethyl acetate extract obtained from the resin of *G. hanburyi* Hook f. and named GH5763 was demonstrated to exhibit anti-inflammatory, analgesic and antipyretic activities.

Despite the aforesaid, there still exists a need for medicinal chemists and pharmaceutical manufacturers in the pharmaceutical industry to explore new compound(s) or new extract(s) that can be easily prepared and that exhibit desirable biological activities such as anti-cancer activity, analgesic activity, anti-inflammatory activity, etc.

Upon further investigation, the applicants have obtained seventeen new compounds from the acetone-extracted product TSB-14 of gamboge resin, in which the seventeen new compounds have been demonstrated to have anti-cancer activity.

SUMMARY OF THE INVENTION

Therefore, according to a first aspect, this invention provides a compound purified from gamboge resin and selected from the group consisting of:

(1) a compound of the formula:

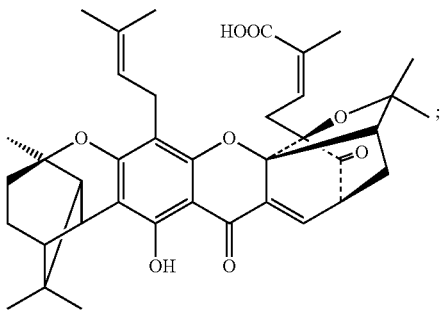

(2) a compound of the formula:

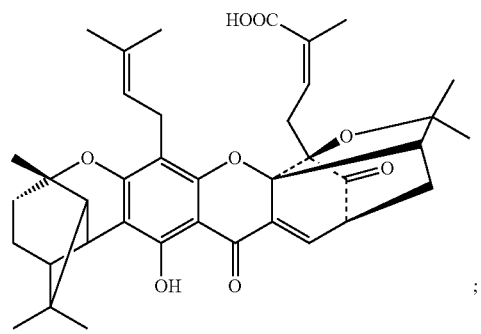

(3) a compound of the formula:

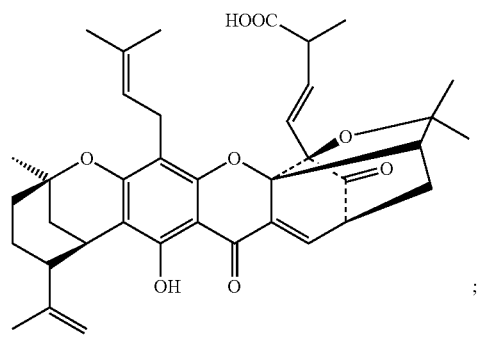

(4) a compound of the formula:
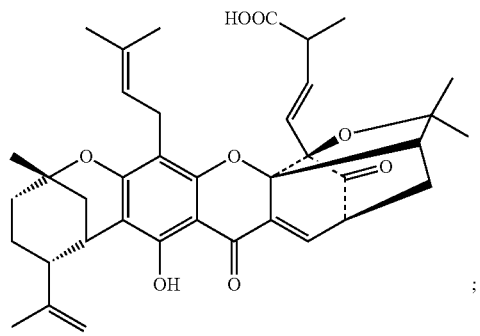
;
(5) a compound of the formula:
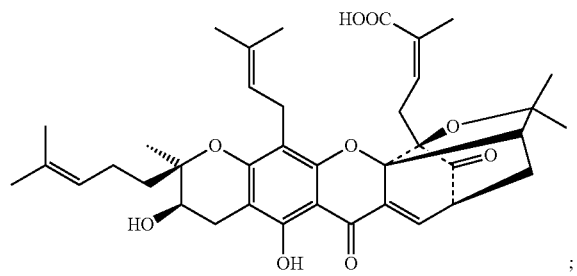
;
(6) a compound of the formula:
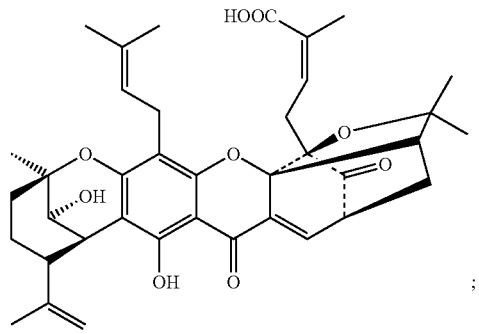
;
(7) a compound of the formula:
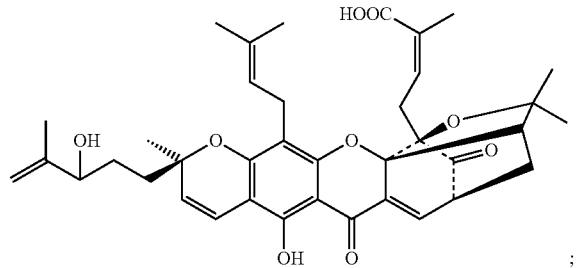
;
(8) a compound of the formula:
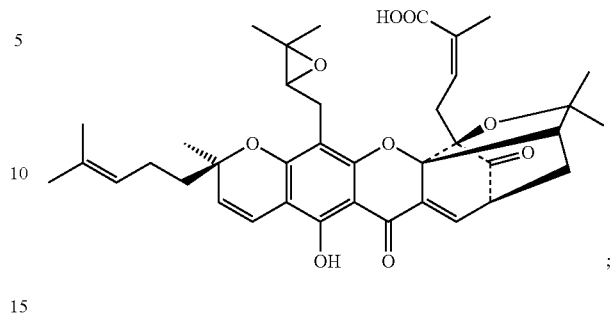
;
(9) a compound of the formula:
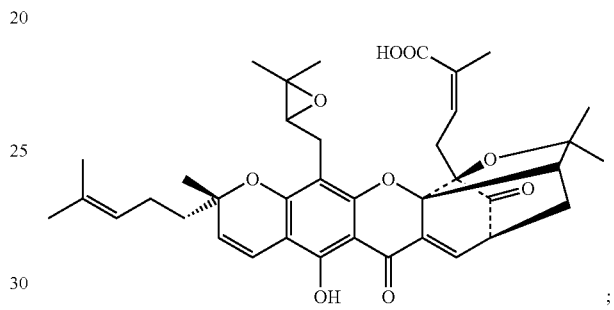
;
(10) a compound of the formula:
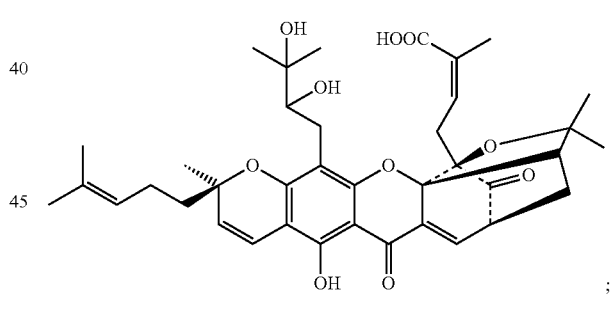
;
(11) a compound of the formula:
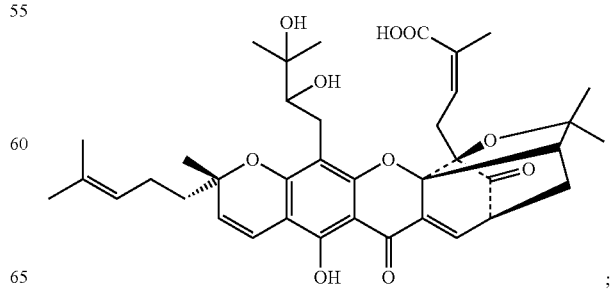
;

(12) a compound of the formula:

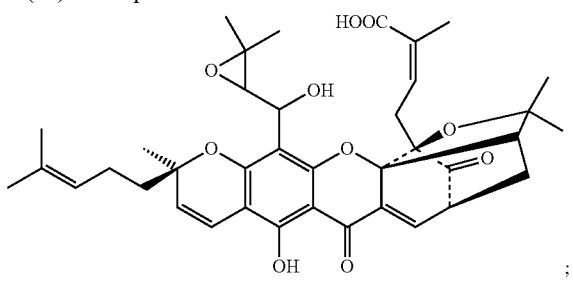

;

(13) a compound of the formula:

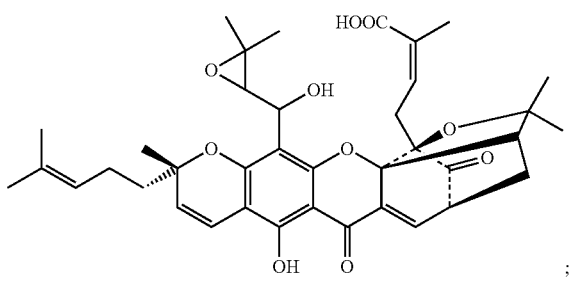

;

(14) a compound of the formula:

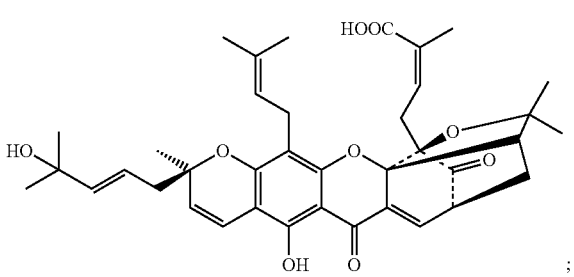

;

(15) a compound of the formula:

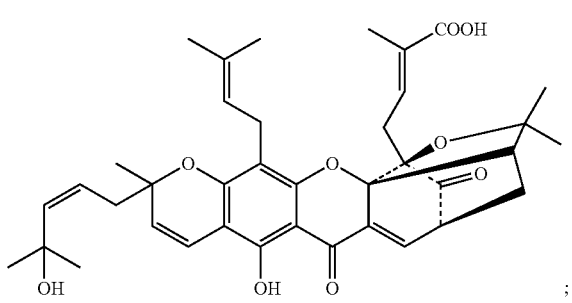

;

(16) a compound of the formula:

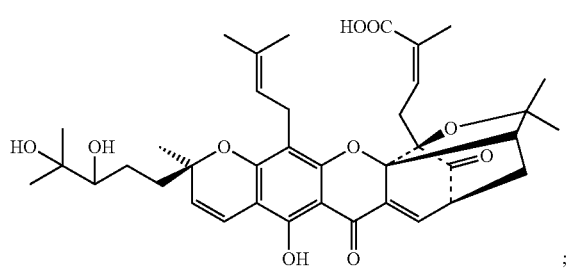

;

and
(17) a compound of the formula:

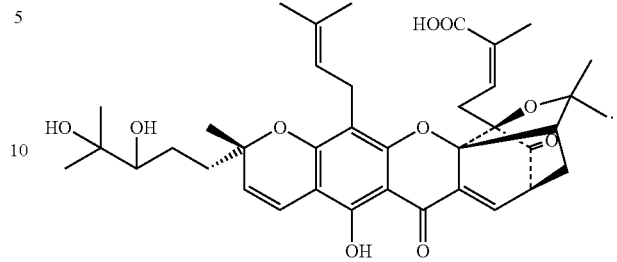

.

According to a second aspect, this invention provides a pharmaceutical composition comprising one or more of the seventeen compounds described above.

According to a third aspect, this invention provides an anti-cancer composition comprising one or more of the seventeen compounds described above.

According to a fourth aspect, this invention provides a method of inhibiting the growth of tumor/cancer cells, comprising contacting the cells with one or more of the seventeen compounds described above.

According to a fifth aspect, this invention provides a method of treating a cancer in a subject, comprising administering to the subject one or more of the seventeen compounds described above.

BRIEF DESCRIPTION OF THE DRAWINGS

The above and other objects, features and advantages of this invention will become apparent with reference to the following detailed description and the preferred embodiments taken in conjunction with the accompanying drawings, in which.

DETAILED DESCRIPTION OF THE PREFERRED EMBODIMENTS

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this invention belongs. One skilled in the art will recognize many methods and materials similar or equivalent to those described herein, which could be used in the practice of this invention. Indeed, this invention is in no way limited to the methods and materials described. For clarity, the following definitions are used herein.

As used herein, the term "active component" or "biologically active compound" is understood to include any substance or material, or combination of substances and materials, which is pharmacologically active and, hence, has therapeutic value.

In Example 1 of U.S. Pat. No. 7,138,428 B2, the applicants disclosed an acetone-extracted product from gamboge resin, i.e., TSB-14, which was obtained by pulverizing gamboge resin into powder, followed by extracting the pulverized powder with acetone. The acetone-extracted product TSB-14 was further identified to contain formoxanthone A, betulin, betulinic acid, morellic acid, isomorellic acid, gambogic acid, isogambogic acid, isomorellinol, and desoxymorellin. In order to explore any other biologically active component(s) that might exist in the acetone-extracted product TSB-14, in this invention, the applicants employed analytical RP-HPLC (reversed phase high performance liquid chromatography) and semi-preparative RP-HPLC analyses to isolate and purify any possible new biologically active compound(s) existing in the acetone-extracted product TSB-14.

Figure 1:
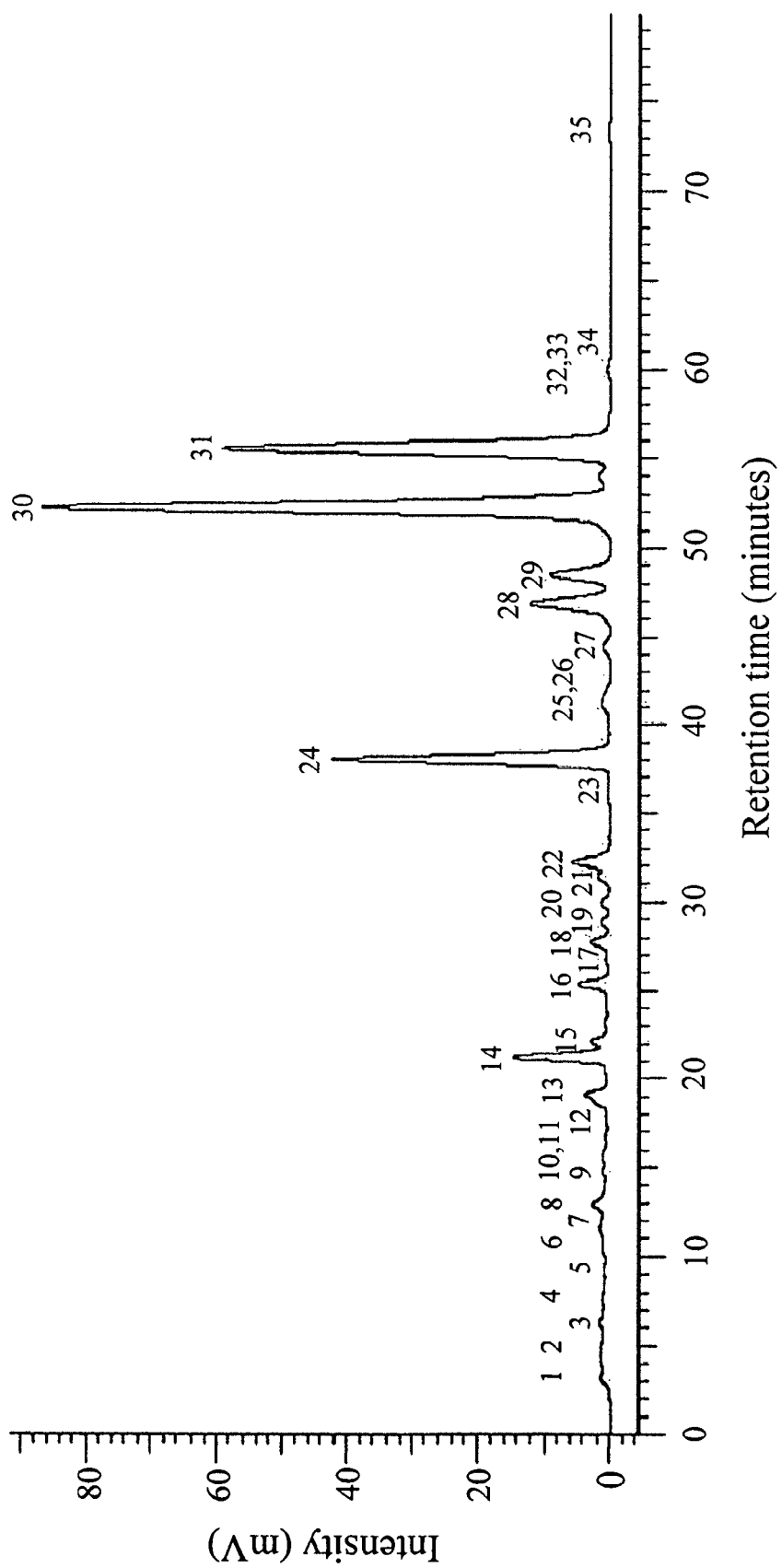
FIG. 1 shows the analytical RP-HPLC elution profile of an acetone-extracted product from gamboge resin, which is referred to as "TSB-14" hereinafter and which was prepared according to the method disclosed in Example 1 of U.S. Pat. No. 7,138,428 B2, in which peaks 1-35 respectively correspond to the thirty-five major components discovered during the retention time from 0 to 80 minutes.

Firstly, the acetone-extracted product TSB-14 was subjected to an analytical RP-HPLC analysis using an analytical RP-C8 column (Luna 3μ C8(2)). As shown in FIG. 1, the obtained analytical RP-HPLC elution profile was observed to have 35 major peaks, which were designated as peaks 1 to 35, respectively.

Figure 2:
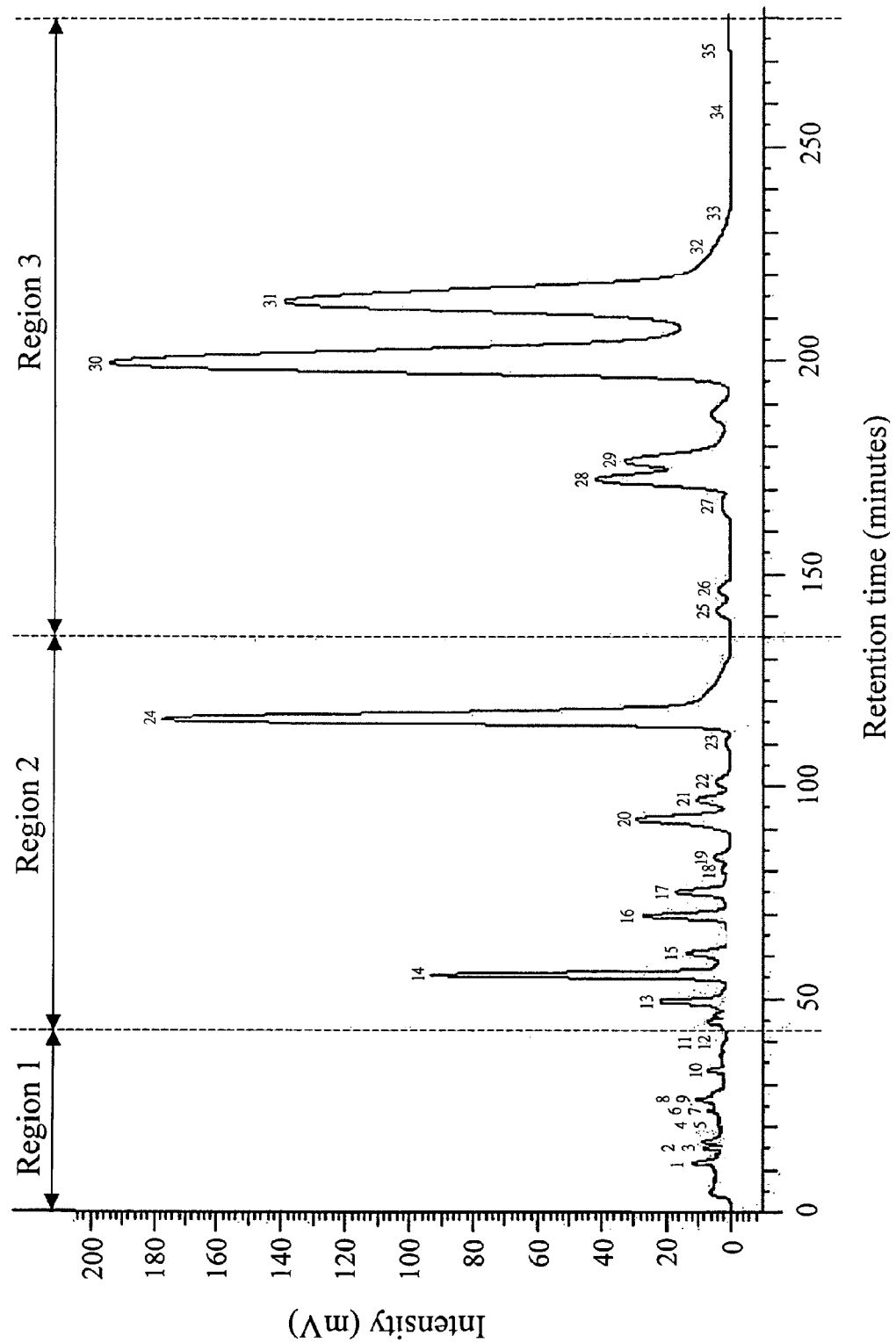
FIG. 2 shows the elution profile of the product TSB-14 obtained from the semi-preparative RP-HPLC analysis conducted in section A, entitled "Semi-preparative RP-HPLC analysis of the product TSB-14," of Example 2, infra, in which the observed peaks 1-35 correspond to those shown in of FIG. 1, respectively.

The acetone-extracted product TSB-14 was then subjected to a semi-preparative RP-HPLC using a semi-preparative RP-C12 column (Synergi 4μ C12). The obtained semi-preparative RP-HPLC elution profile as shown in FIG. 2, which was found to have 35 major peaks comparatively corresponding to those shown in FIG. 1, was divided into three regions, in which Region 1 included peaks 1-12 discovered during the retention time from 0 to 42 minutes; Region 2 included peaks 13 to 24 discovered during the retention time from 42 to 135 minutes; and Region 3 includes peaks 25 to 35 discovered during the retention time from 135 to 280 minutes.

Based on the three divided regions shown in FIG. 2, the acetone-extracted product TSB-14 was fractionated by semi-preparative RP-HPLC to provide three eluates that respectively corresponded to said three divided regions. The three eluates thus collected were respectively subjected to the following treatment: partitioning a collected eluate in $H_2O$ and ethyl acetate; after washing with $H_2O$ so as to remove TFA, the organic layer was dried on anhydrous $Na_2SO_4$, filtered, and the organic solvent was removed using a vacuum rotatory evaporator. Three corresponding fractions 1-3 thus obtained were separately subjected to the semi-preparative RP-HPLC analysis to provide elution profiles as shown in FIGS. 3, 4 and 5, which were observed to have peaks 1-12, 13-24 and 25-35, respectively.

Figure 3:
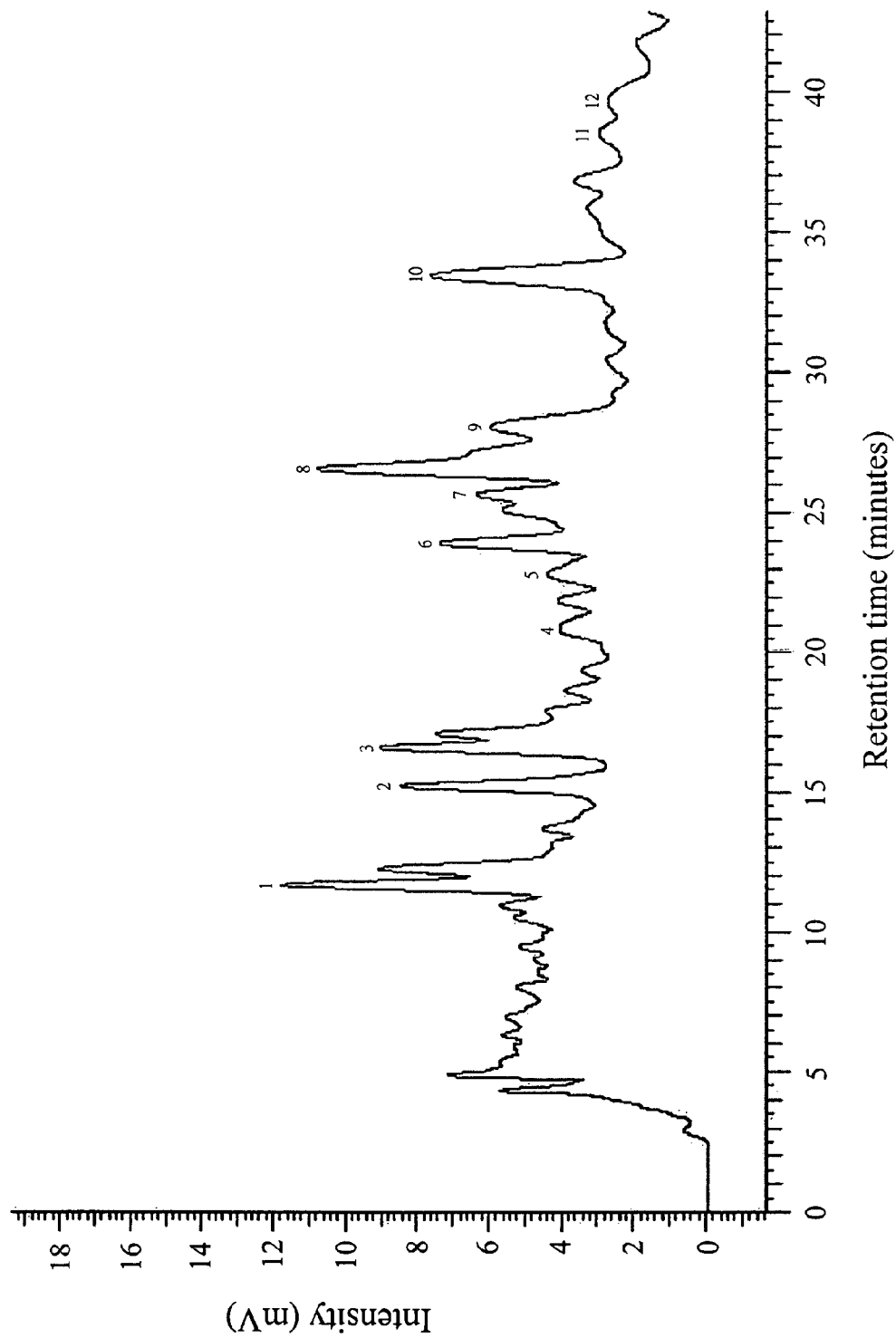
FIG. 3 shows the semi-preparative RP-HPLC elution profile of fraction 1 obtained in section B, entitled "Preparation of fractions 1-3" of Example 2, infra, in which the observed twelve peaks correspond to peaks 1-12 shown in FIG. 2, respectively.

The obtained fraction 1 was subjected to the semi-preparative RP-HPLC analysis and, according to its elution profile shown in FIG. 3, twelve evaluates that respectively corresponded to peaks 1-12 shown in FIG. 3 were collected. The collected eluates 1-12 were then subjected to the following treatment: partitioning a collected eluate in $H_2O$ and ethyl acetate; after washing with $H_2O$ so as to remove TFA, the organic layer was dried on anhydrous $Na_2SO_4$, filtered, and the organic solvent was removed using a vacuum rotatory evaporator. Twelve crude products were obtained, each of which was further purified. After completion of purification, twelve purified products were obtained from the eluates 1-12 of fraction 1 and were designated as Gh-3261, Gh-3271, Gh-3272, Gh-3311, Gh-3332, Gh-1036, Gh-3291, Gh-631, Gh-1052, Gh-3351, Gh-3353 and Gh-3352, respectively (see Table 1 of Example 2, infra).

Figure 4:
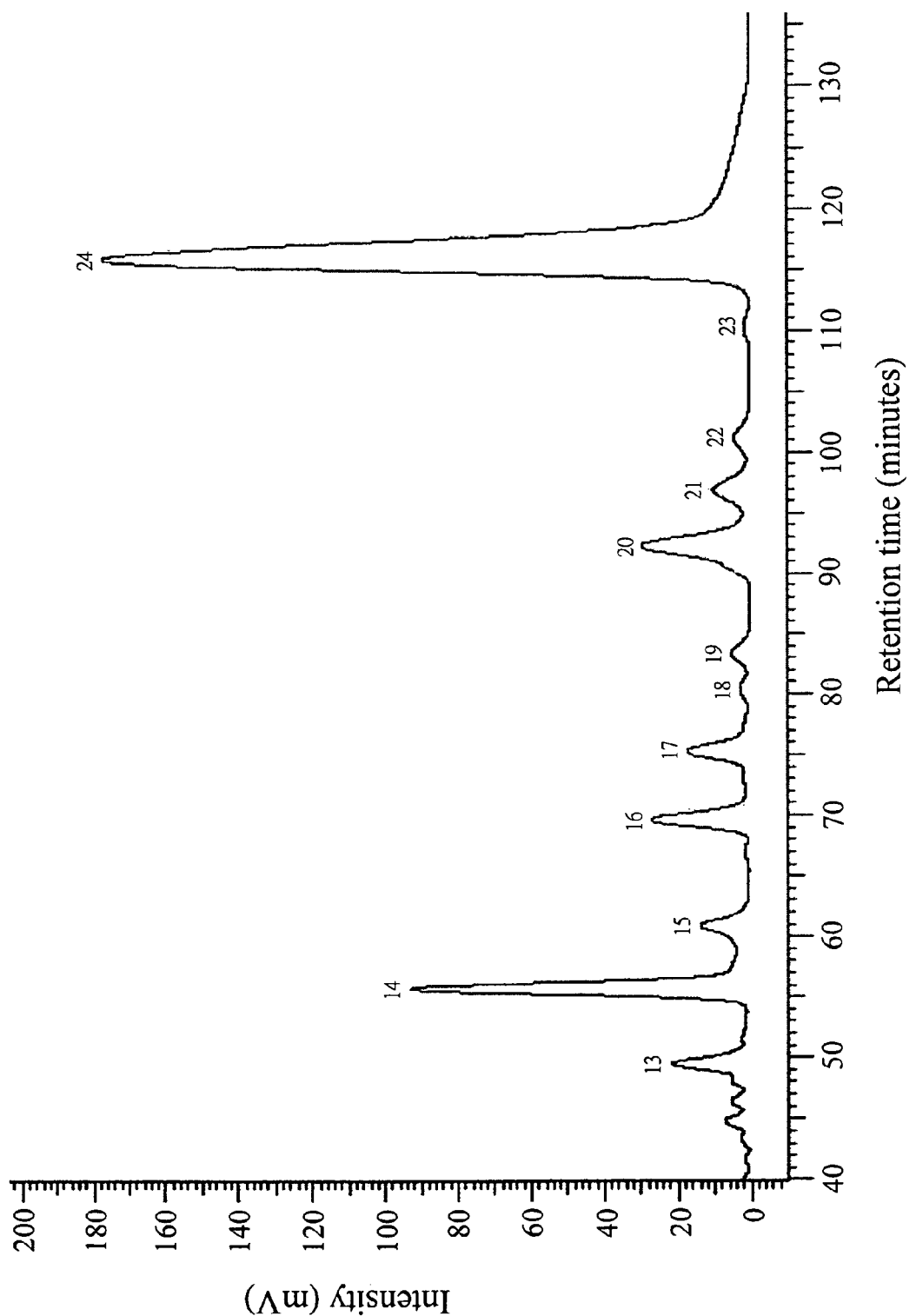
FIG. 4 shows the semi-preparative RP-HPLC elution profile of fraction 2 obtained in Example 2, infra, in which the observed twelve peaks correspond to peaks 13-24 shown in FIG. 2, respectively.

Fraction 2 was treated in a manner identical to fraction 1, and according to its elution profile shown in FIG. 4, eluates 13-24 that respectively corresponded to peaks 13-24 shown in FIG. 4 were collected, and twelve purified products were further obtained from the eluates 13-24 of fraction 2 and were designated as Gh-47, Gh-4602, Gh-4601, Gh-1601-A, Gh-1050, Gh-1602, Gh-1631, Gh-2641-1, Gh-2501, Gh-2642, Gh-2507 and Gh-2505, respectively (see Table 2 of Example 2, infra).

Figure 5:
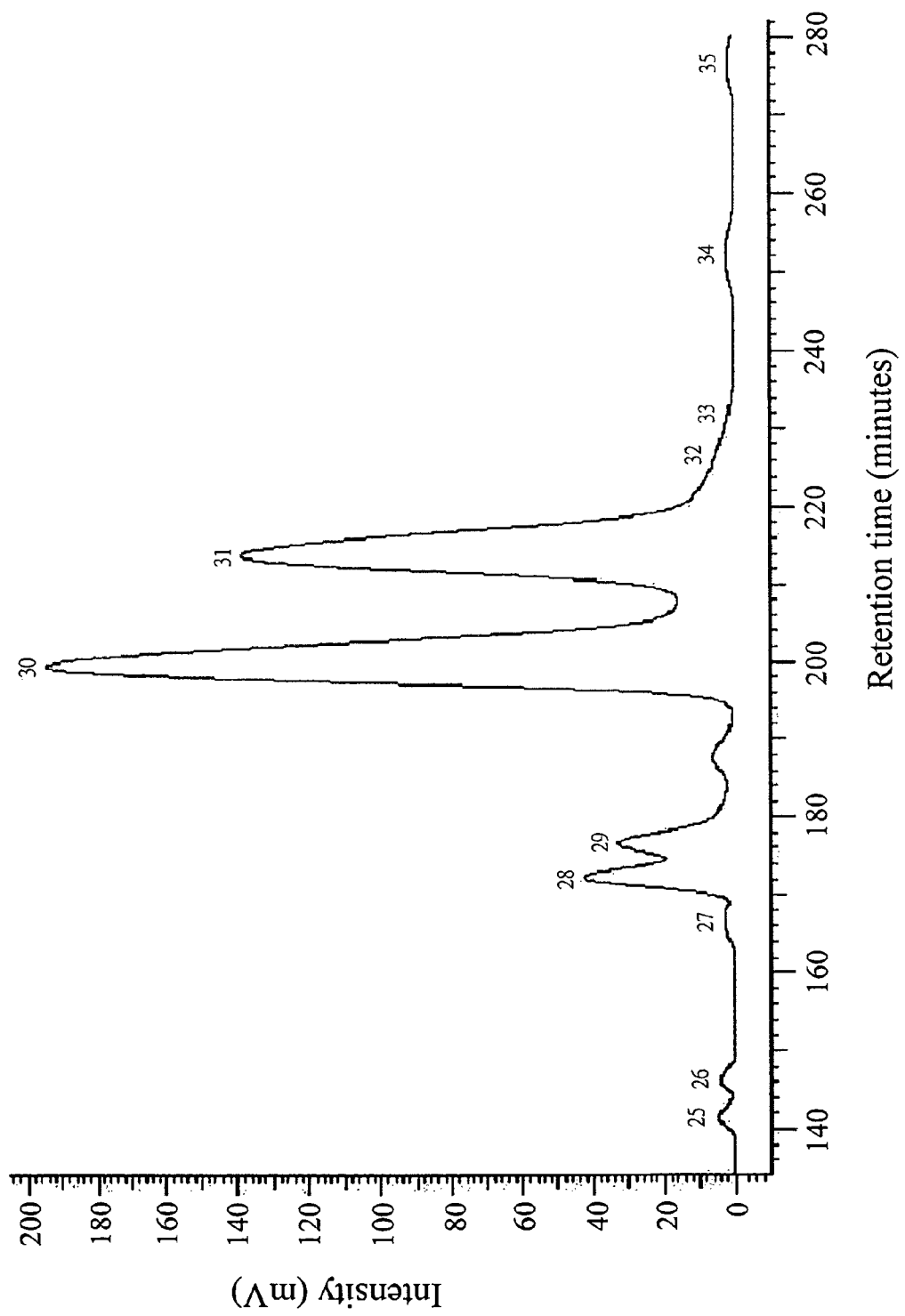
FIG. 5 shows the semi-preparative RP-HPLC elution profile of fraction 3 obtained in Example 2, infra, in which the observed eleven peaks correspond to peaks 25-35 shown in FIG. 2, respectively.

Fraction 3 was likewise treated in a manner identical to fraction 1, and according to its elution profile shown in FIG. 5, eluates 25-35 that respectively corresponded to peaks 25-35 shown in FIG. 5 were collected, and eleven purified products were further obtained from the eluates 25-35 of fraction 3 and were designated as Gh-2508, Gh-2603-1, Gh-2603-2, Gh-1641, Gh-1642, Gh-2605, Gh-2606, Gh-2607-B, Gh-2607-1A, Gh-2301 and Gh-4301, respectively (see Table 3 of Example 2, infra)

The thirty-five products purified from fractions 1-3 were subjected to physical and chemical analyses, including melting point determination, nuclear magnetic resonance (NMR) spectroscopy (e.g., $^1$H-NMR and $^{13}$C-NMR spectroscopy), mass spectrometry (e.g., electron impact mass spectrometry (EIMS), high-resolution electron impact mass spectrometry (HREIMS), fast atom bombardment mass spectrometry (FABMS), and high-resolution fast atom bombardment mass spectrometry (HRFABMS), etc.), etc.

Product Gh-631 has been confirmed by chemical structure analysis to be a known compound, i.e., "formoxanthone A" disclosed in U.S. Pat. No. 7,138,428 B2, which has the following chemical structure:

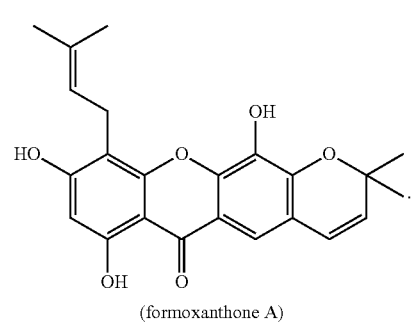

(formoxanthone A)

Products Gh-4602 and Gh-47 have been confirmed by chemical structure analysis to be two known morellic acid stereoisomers, morellic acid and isomorellic acid, which have the following chemical structures, respectively:

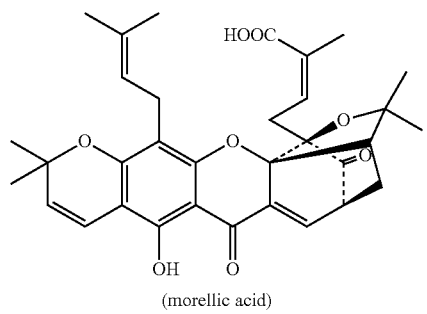
(morellic acid) Gh-4602

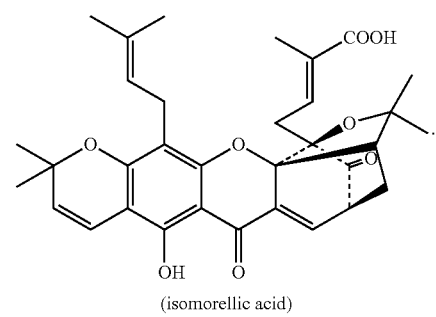
(isomorellic acid) Gh-47

Product Gh-4601 has been confirmed by chemical structure analysis to be a known derivative of isomorellic acid, i.e., isomorellinol, which has the following chemical structure:

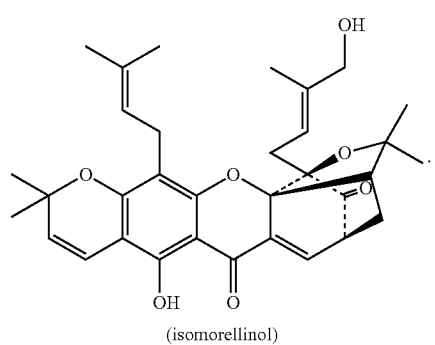
(isomorellinol) Gh-4601

Products Gh-1601-A and Gh-1602 have been confirmed by chemical structure analysis to be two known C-2 epimers of 30-hydroxygambogic acid, i.e., 30-hydroxygambogic acid and 30-hydroxyepigambogic acid, which have the following chemical structures, respectively:

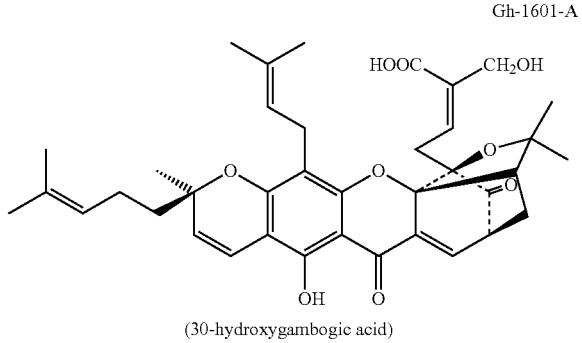
(30-hydroxygambogic acid) Gh-1601-A

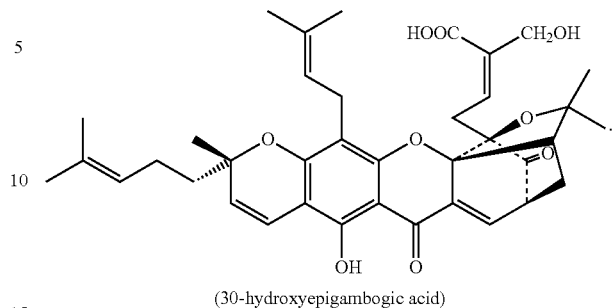
(30-hydroxyepigambogic acid) Gh-1602

Product Gh-2641-1 has been confirmed by chemical structure analysis to be neogambogic acid, which has the following chemical structure:

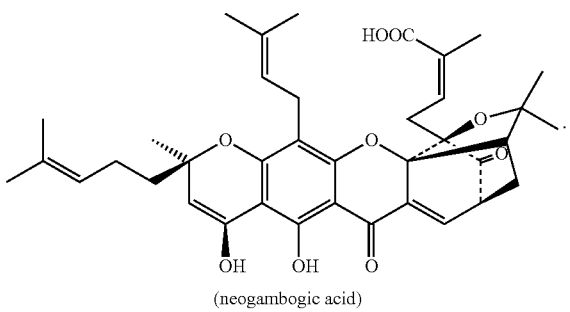
(neogambogic acid) Gh-2641-1

Product Gh-2501 has been confirmed by chemical structure analysis to be isomorellin, which has the following chemical structure:

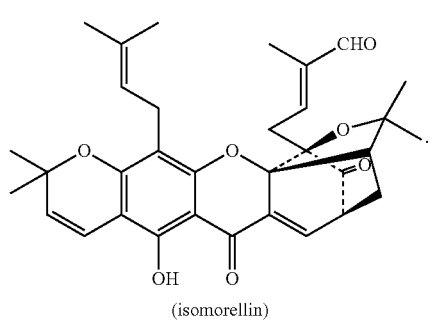
(isomorellin) Gh-2501

Products Gh-2505 and Gh-2642 have been confirmed by chemical structure analysis to be two known gambogenic stereoisomers, i.e., gambogenic acid and isogambogenic acid, which have the following chemical structures, respectively:

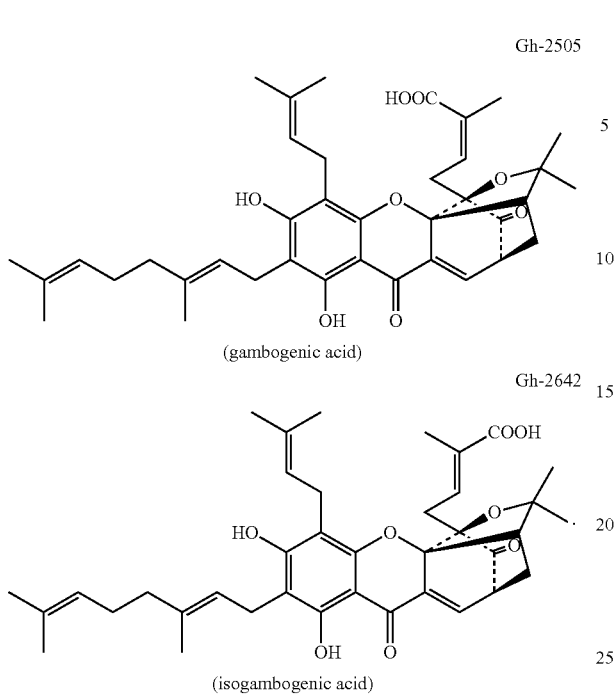

(gambogenic acid) Gh-2505

(isogambogenic acid) Gh-2642

Products Gh-2603-2 and Gh-2603-1 have been confirmed by chemical structure analysis to be two known C-2 epimers of gambogellic acid, i.e., gambogellic acid and epigambogellic acid, which have the following chemical structures, respectively:

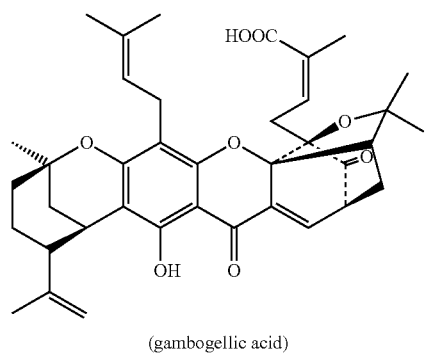

(gambogellic acid) Gh-2603-2

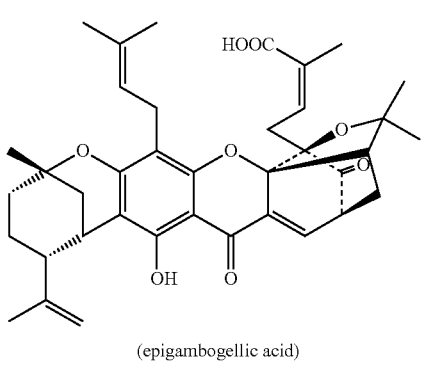

(epigambogellic acid) Gh-2603-1

Products Gh-1641 and Gh-1642 have been confirmed by chemical structure analysis to be two known C-2 epimers of isogambogic acid, i.e., isogambogic acid and epiisogambogic acid, which have the following chemical structures, respectively:

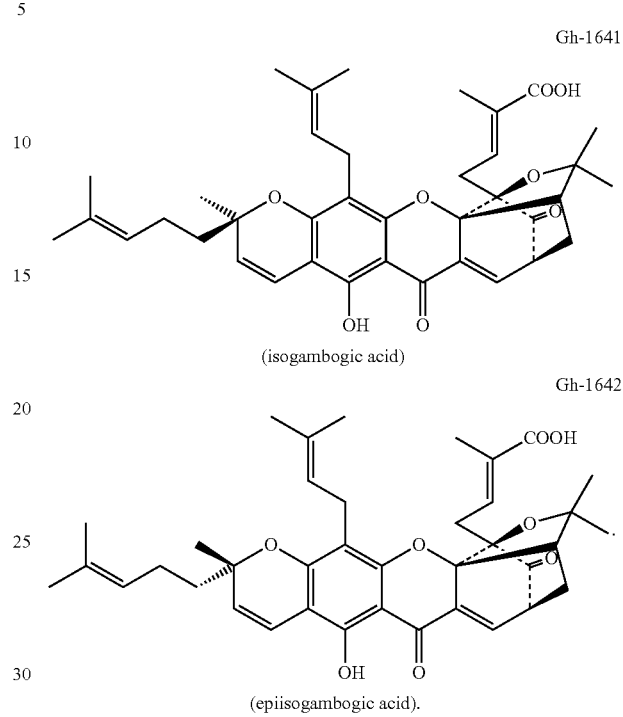

(isogambogic acid) Gh-1641

(epiisogambogic acid) Gh-1642

Products Gh-2605 and Gh-2606 have been confirmed by chemical structure analysis to be two known C-2 epimers of gambogic acid, i.e., gambogic acid and epigambogic acid, which have the following chemical structures, respectively:

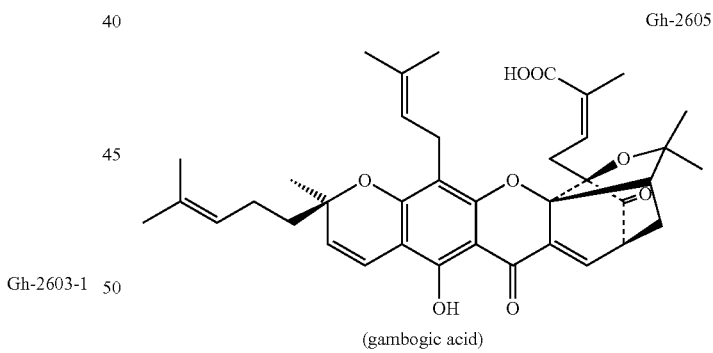

(gambogic acid) Gh-2605

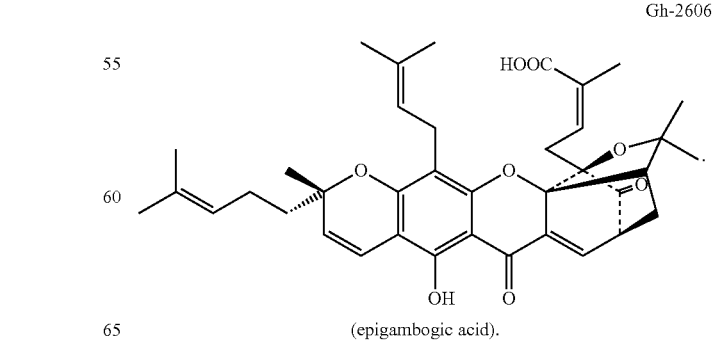

(epigambogic acid) Gh-2606

Product Gh-2301 has been confirmed by chemical structure analysis to be a known compound, i.e., desoxymorellin, which has the following chemical structure:

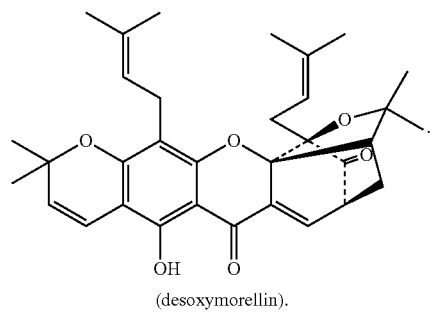
(desoxymorellin).

Product Gh-4301 has been confirmed by chemical structure analysis to be a known compound, i.e., desoxygambogenin, which has the following chemical structure:

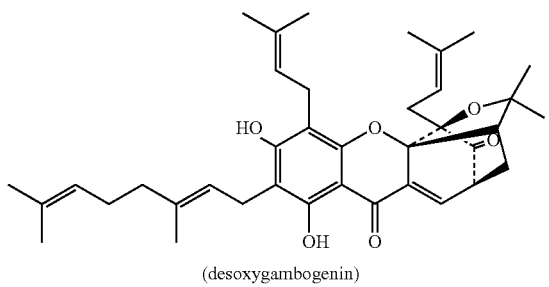
(desoxygambogenin)

It has been confirmed from the results of chemical structure analysis and a comparison with the spectroscopic data of known compounds that products Gh-3352 and Gh-3351 are two novel compounds which are hitherto not reported. Products Gh-3352 and Gh-3351, which are C-2 epimers with the following chemical structures, are herein named as "formoxanthone E" and "epiformoxanthone E," respectively:

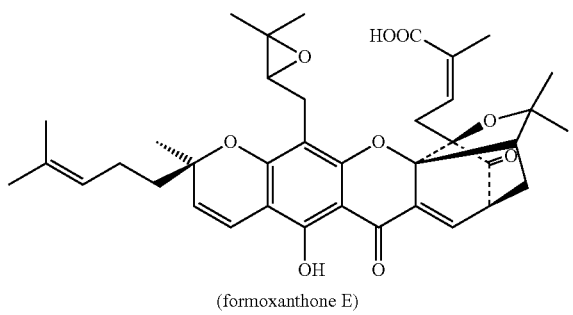
(formoxanthone E)

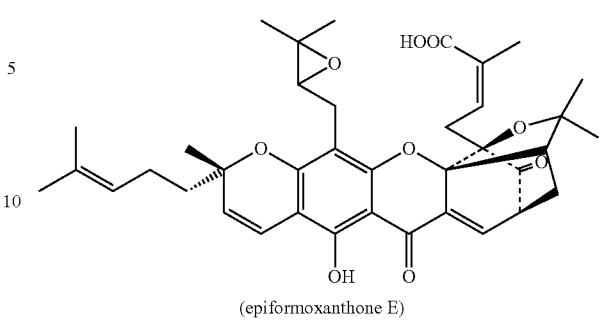
(epiformoxanthone E)

It has been confirmed from the result of chemical structure analysis and a comparison with the spectroscopic data of known compounds that products Gh-1052 and Gh-1036 are two novel compounds which are hitherto not reported. Products Gh-1052 and Gh-1036, which are C-2 epimers with the following chemical structures, are herein named as "formoxanthone F" and "epiformoxanthone F," respectively:

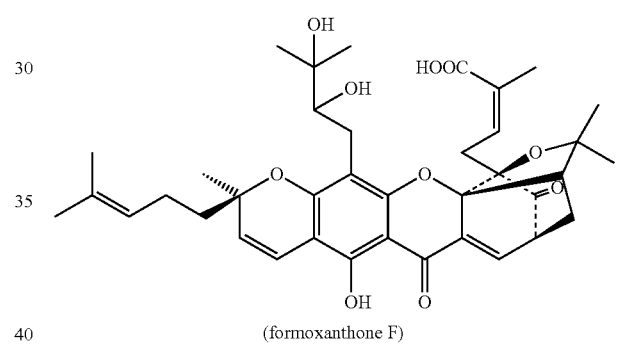
(formoxanthone F)

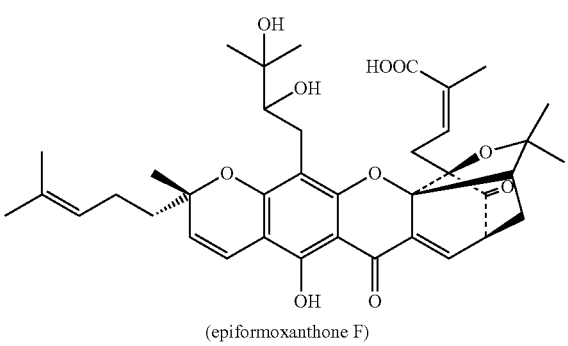
(epiformoxanthone F)

It has been confirmed from the result of chemical structure analysis and a comparison with the spectroscopic data of known compounds that products Gh-3353 and Gh-3311 are two novel compounds which are hitherto not reported. Products Gh-3353 and Gh-3311, which are C-2 epimers with the following chemical structures, are herein named as "formoxanthone G" and "epiformoxanthone G," respectively:

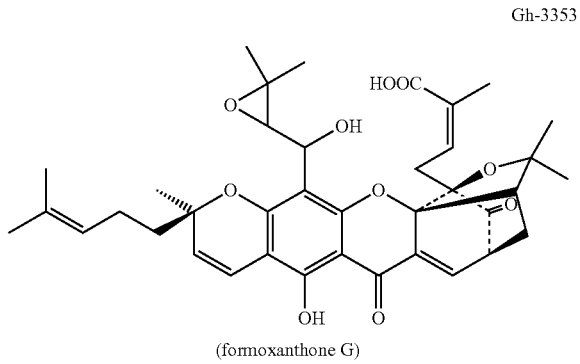
(formoxanthone G)

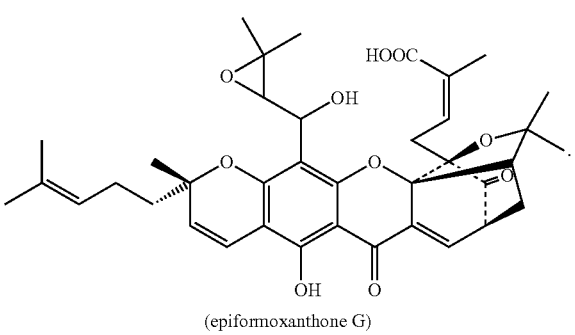
(epiformoxanthone G)

It has been confirmed from the result of chemical structure analysis and a comparison with the spectroscopic data of known compounds that products Gh-3261 and Gh-3271 are two novel compounds which are hitherto not reported. Products Gh-3261 and Gh-3271, which are C-2 epimers with the following chemical structures, are herein named as "formoxanthone J" and "epiformoxanthone J," respectively:

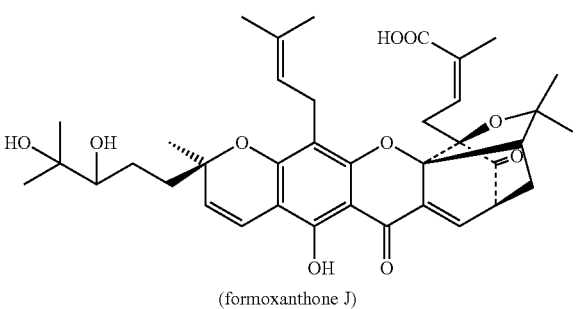
(formoxanthone J)

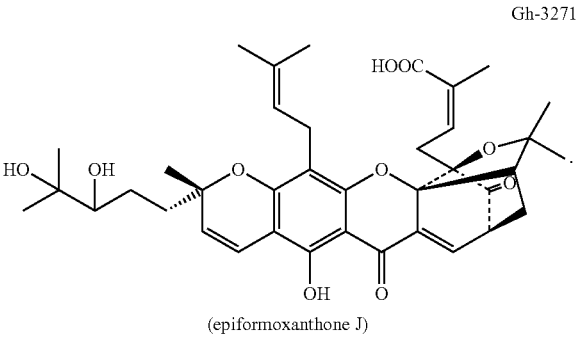
(epiformoxanthone J)

It has been confirmed from the result of chemical structure analysis and a comparison with the spectroscopic data of known compounds that product Gh-3272 is a novel compound which is hitherto not reported. Product Gh-3272 is herein named as "formoxanthone H" and has the following chemical structure:

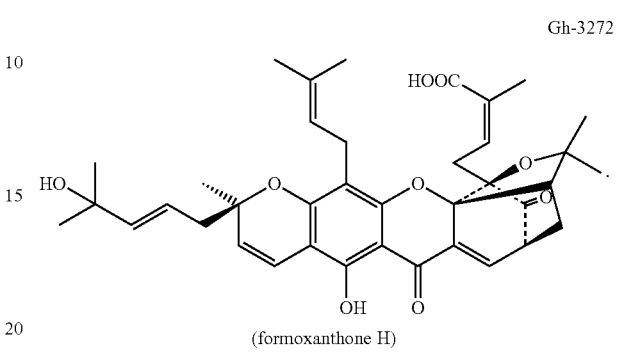
(formoxanthone H)

It has been confirmed from the result of chemical structure analysis and a comparison with the spectroscopic data of known compounds that product Gh-3332 is a novel compound which is hitherto not reported. Product Gh-3332 is herein named as "isoformoxanthone I" and has the following chemical structure:

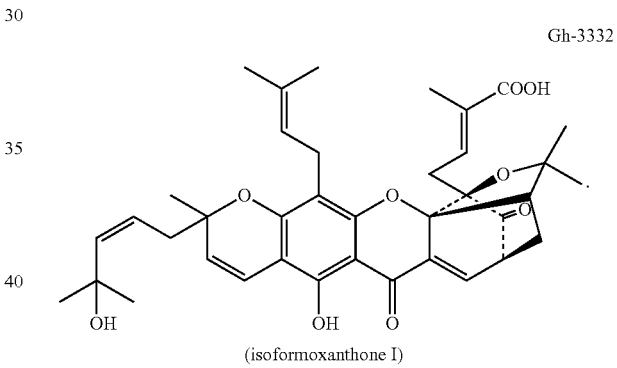
(isoformoxanthone I)

It has been confirmed from the result of chemical structure analysis and a comparison with the spectroscopic data of known compounds that product Gh-3291 is a novel compound which is hitherto not reported. Product Gh-3291 is herein named as "formoxanthone D" and has the following chemical structure:

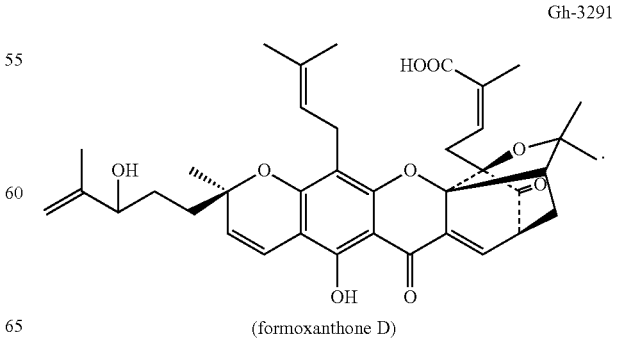
(formoxanthone D)

It has been confirmed from the result of chemical structure analysis and a comparison with the spectroscopic data of known compounds that product Gh-1631 is a novel compound which is hitherto not reported. Product Gh-1631 is herein named as "formoxanthone C" and has the following chemical structure:

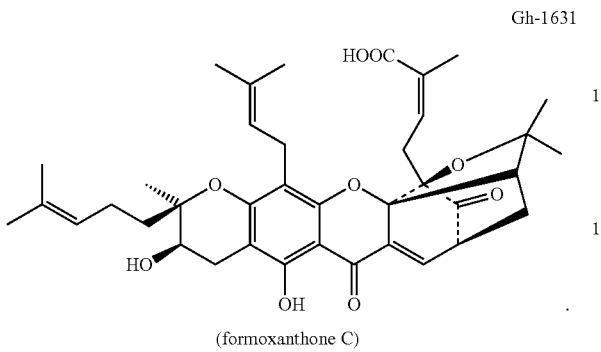

(formoxanthone C)

It has been confirmed from the result of chemical structure analysis and a comparison with the spectroscopic data of known compounds that product Gh-1050 is a novel compound which is hitherto not reported. Product Gh-1050 is herein named as "3α-hydroxygambogellic acid" and has the following chemical structure:

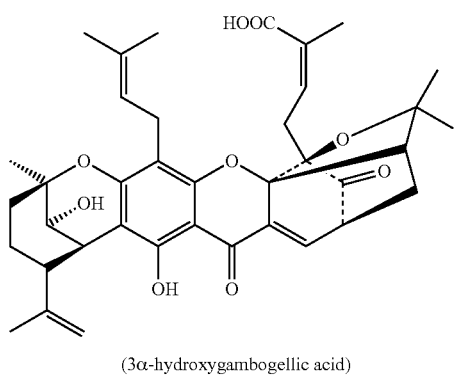

(3α-hydroxygambogellic acid)

It has been confirmed from the result of chemical structure analysis and a comparison with the spectroscopic data of known compounds that products Gh-2508 and Gh-2507 are two novel compounds which are hitherto not reported. Products Gh-2508 and Gh-2507, which are C-2 epimers with the following chemical structures, are herein named as "β-gambogellic acid" and "β-epigambogellic acid," respectively:

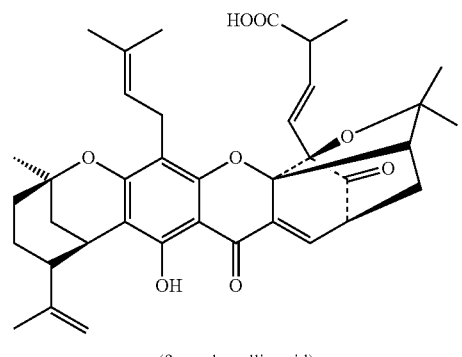

(β-gambogellic acid)

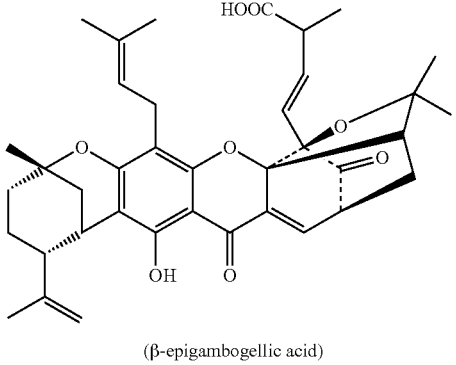

(β-epigambogellic acid)

It has been confirmed from the result of chemical structure analysis and a comparison with the spectroscopic data of known compounds that products Gh-2607-B and Gh-2607-1A are two novel compounds which are hitherto not reported. Products Gh-2607-B and Gh-2607-1A are C-2 epimers with the following chemical structures, are herein named as "formoxanthone B" and "epiformoxanthone B," respectively:

(formoxanthone B)

(epiformoxanthone B)

After comparing the chemical structures of the seventeen new compounds obtained from fractions 1-3, the applicants found that these seventeen new compounds share a common skeleton structure and may be represented by the following formula (I):

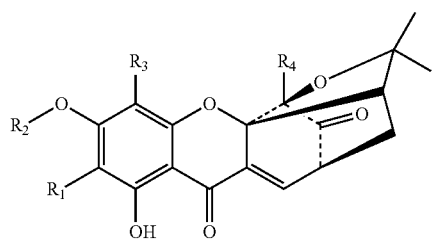

(I)

wherein:

R$_1$ and R$_2$ together form a moiety selected from the group consisting of:

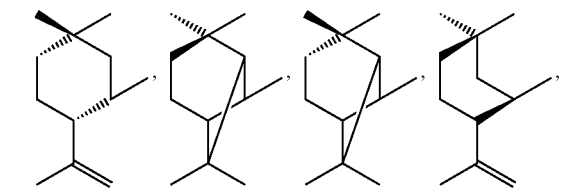

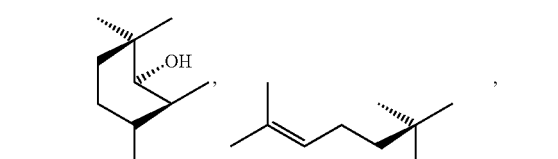

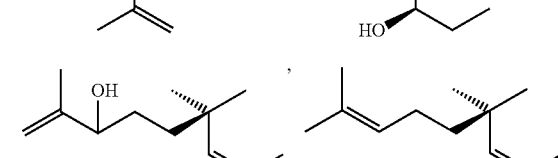

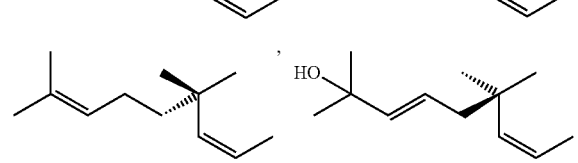

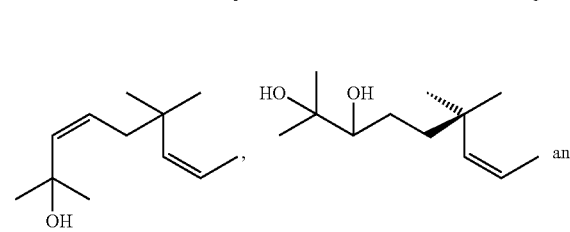

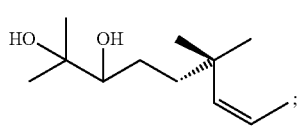;

R$_3$ is selected from the group consisting of: 3-methyl-2-butenyl, 1-hydroxy-2,3-epoxy-3-methylbutyl, 2,3-epoxy-3-methylbutyl, and 2,3-dihydroxy-3-methylbutyl; and R$_4$ is selected from the group consisting of: 3-carboxyl-2Z-butenyl, 3-carboxyl-2E-butenyl, and 3-carboxyl-1E-butenyl;

but excluding compounds of the following formulae:

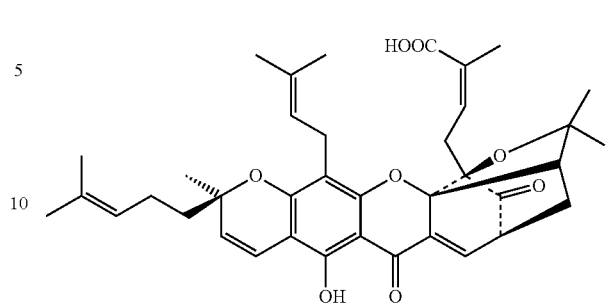

,

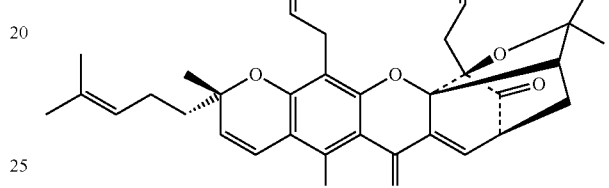

,

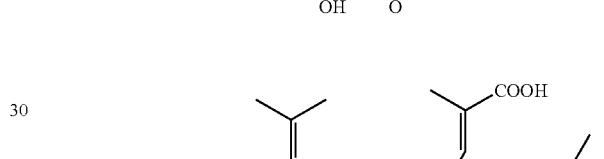

,

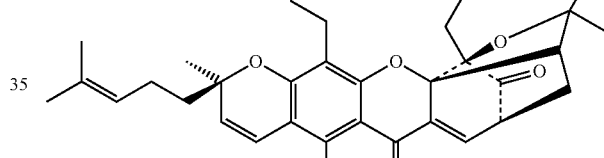

,

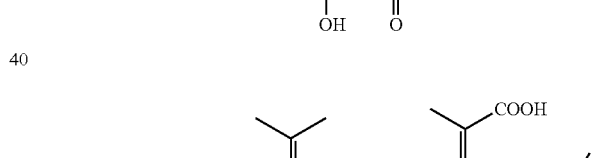

,

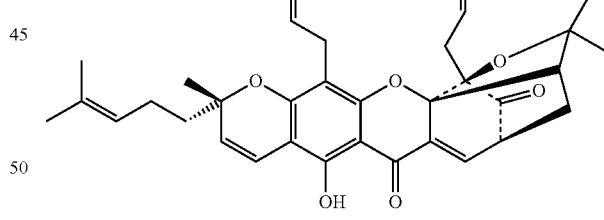

,

,

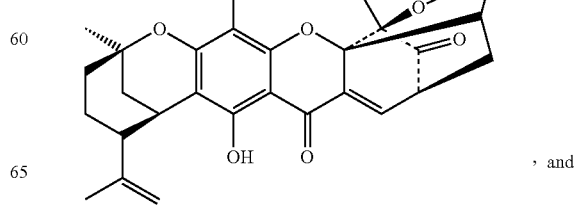

, and

-continued

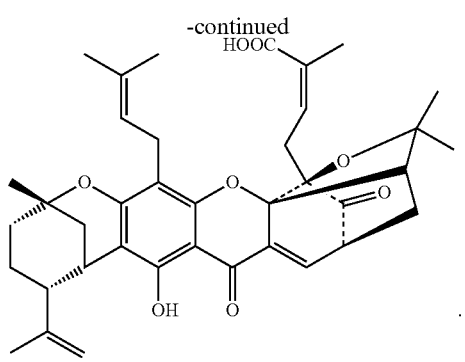

According to the chemical structure shown in the above formula (I), the seventeen new compounds obtained in this invention may be chemically synthesized by methodologies well known to those skilled in the art.

In this invention, the seventeen new purified compounds obtained from the acetone-extracted product TSB-14 from gamboge resin were subjected to in vitro anti-cancer tests and were found to exhibit inhibitory activities against the growth of tumor/cancer cells (such as human breast adenocarcinoma cells, human colon adenocarcinoma cells, human promyelocytic leukemia cells, human hepatocellular carcinoma cells, human lung carcinoma cells, and human histocytic lymphoma cells). It is therefore contemplated that the seventeen new purified compounds have potential for use in cancer therapy.

Accordingly, this invention provides a compound purified from gamboge resin and selected from the group consisting of:

(1) a compound of the formula:

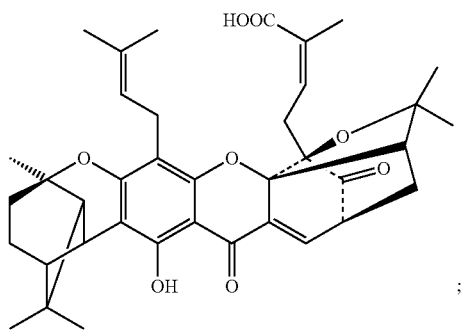

;

(2) a compound of the formula:

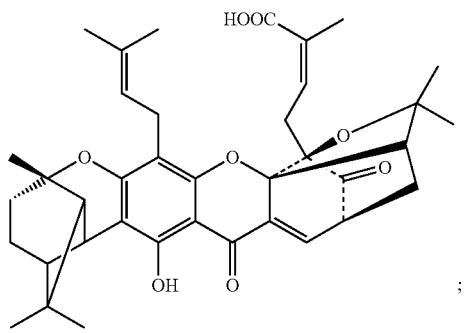

;

(3) a compound of the formula:

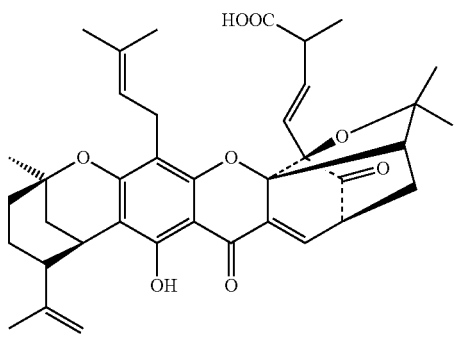

;

(4) a compound of the formula:

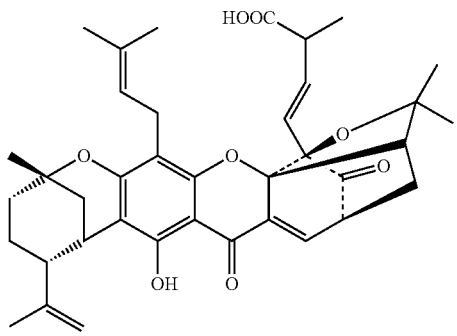

;

(5) a compound of the formula:

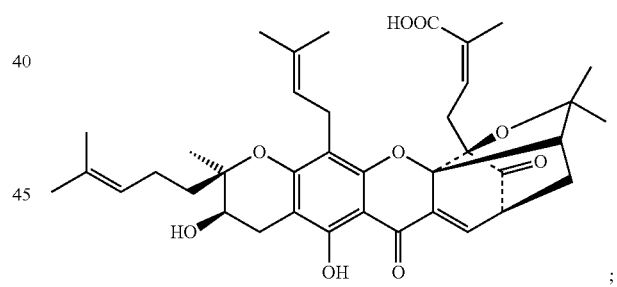

;

(6) a compound of the formula:

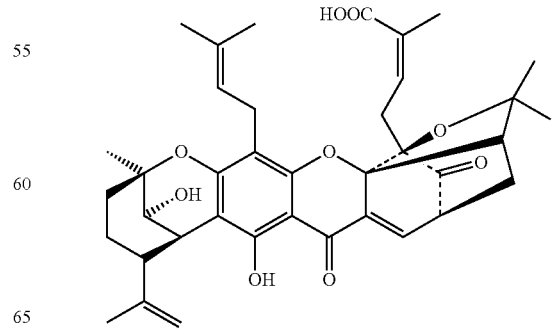

;

(7) a compound of the formula:
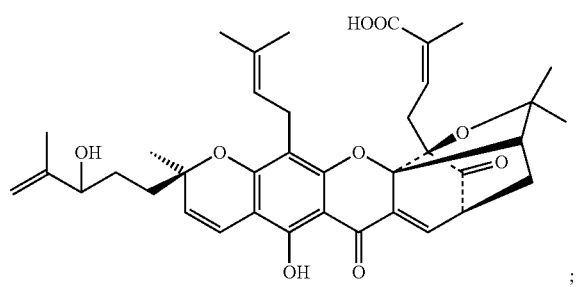
;
(8) a compound of the formula:
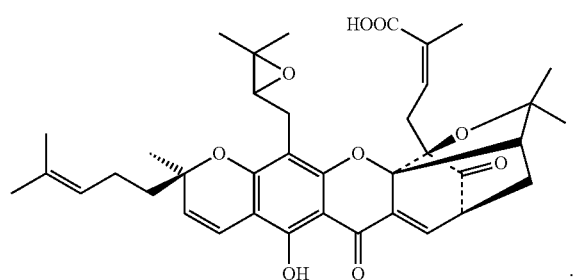
;
(9) a compound of the formula:
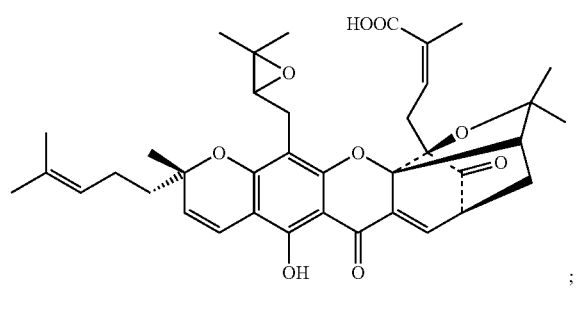
;
(10) a compound of the formula:
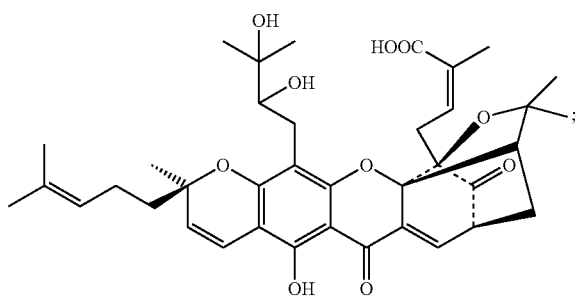
;
(11) a compound of the formula:
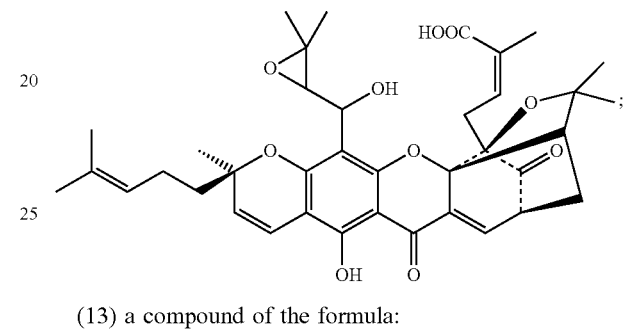
;
(12) a compound of the formula:
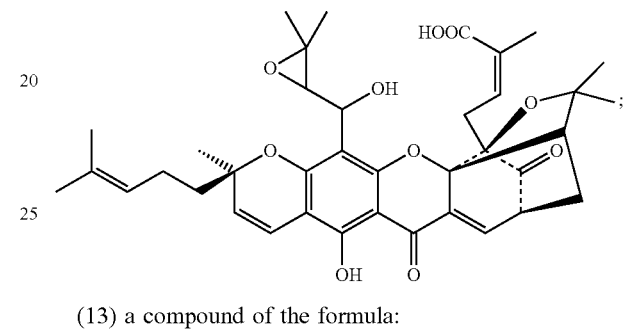
;
(13) a compound of the formula:
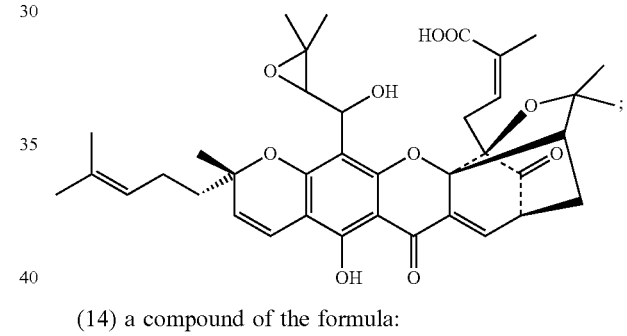
;
(14) a compound of the formula:
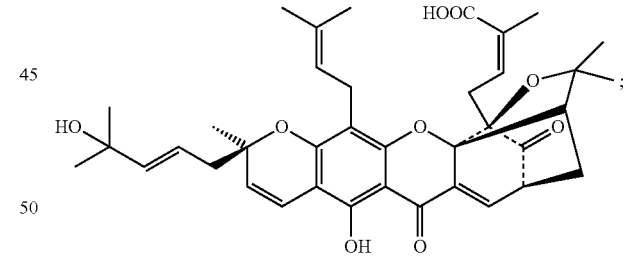
;
(15) a compound of the formula:
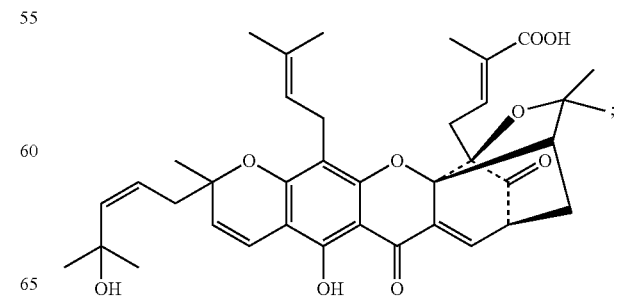
;

(16) a compound of the formula:

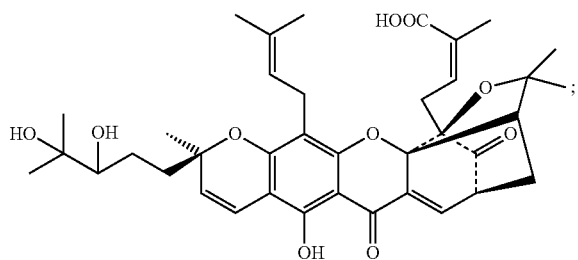

and

(17) a compound of the formula:

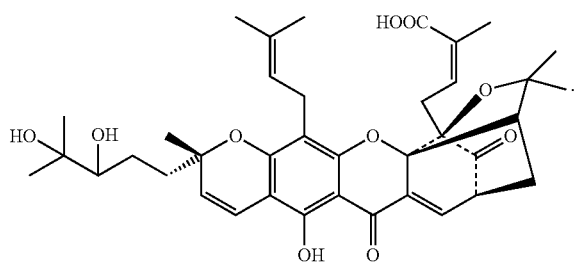

This invention further provides a pharmaceutical composition comprising one or more of the seventeen compounds described above.

This invention also provides a method of inhibiting the growth of tumor/cancer cells, comprising contacting the cells with one or more of the seventeen compounds described above.

In addition, this invention further provides an anti-cancer composition comprising one or more of the seventeen compounds described above.

This invention also provides a method of treating a cancer in a subject, comprising administering to the subject one or more of the seventeen compounds described above.

The pharmaceutical composition according to this invention can be formulated into a dosage form suitable for parenteral, topical, or oral administration using technology well known to those skilled in the art, which includes, but is not limited to, injections (e.g., sterile aqueous solutions or dispersions), sterile powder, tablets, troches, pills, capsules, and the like.

The pharmaceutical composition according to this invention can be parenterally administered via one or more of the following routes: intravenous injection, intramuscular injection, and subcutaneous injection.

In a preferred embodiment according to this invention, the pharmaceutical composition is formulated into a dosage form suitable for oral administration.

The pharmaceutical composition according to this invention can additionally comprise a pharmaceutically acceptable carrier widely employed in the art of drug-manufacturing. For instance, the pharmaceutically acceptable carrier may include one or more of the following agents: solvents, emulsifiers, suspending agents, decomposers, binding agents, excipients, stabilizing agents, chelating agents, diluents, gelling agents, preservatives, lubricants, absorption delaying agents, plasticizer, filling agents, disintegrants, surfactants, thickening agents, liposomes, and the like.

The dosage and the frequency of administration of the pharmaceutical composition according to this invention may vary depending on the following factors: the severity of the disease to be treated, the route of administration, and the weight, age, physical condition and response of the subject to be treated. For instance, the daily dosage of the pharmaceutical composition according to this invention may be 2.1 to 3.0 mg per kilogram of the body weight, and may be administered in a single dose or in several doses.

The present invention will be described in more detail with reference to the following examples, which are given for the purpose of illustration only and are not intended to limit the scope of the present invention.

EXAMPLES

General Procedures

Melting point was determined using a micro melting-point apparatus (Yanaco, Japan).

EIMS spectra and HREIMS spectra were recorded on a MAT-95 XL high-resolution mass spectrometer.

FABMS spectra and HRFABMS spectra were recorded on a JEOL JMSSX SX 102A mass spectrometer or a Finnigan MAT 95 XL mass spectrometer.

$^1$H-NMR and $^{13}$C-NMR spectra, $^1$H-$^1$H COSY (homonuclear correlation spectroscopy) spectra, HMQC (heteronuclear multiple-quantum coherence) spectra, HMBC (heteronuclear multiple-bond coherence) spectra, and NOESY (nuclear Overhauser effect spectroscopy) spectra, were recorded on a BRUKER AM400 spectrometer, a VARIAN GEMINI-400 spectrometer, or a BRUKER ADVANCE DMX-600 spectrometer, in which CDCl$_3$ or acetone-d$_6$ was used as a solvent for the NMR measurements, and the chemical shift (δ) is expressed in ppm relative to a standard.

Analytical reversed-phase high performance liquid chromatography (RP-HPLC) was performed using the following instruments: a Hitachi L-7400 UV detector, a Hitachi L-7100 pump, a Hitachi HPLC D-7000 system, a column oven (Super CO-150, Enshine, Taiwan), a guard column (SecurityGuard cartridge C8, size: 3.0 mm×4.0 mm, Phenomenex, USA), and an analytical column (Luna 3μ C8(2) 100 Å, size: 4.6 mm×150 mm, Phenomenex, USA). Operation conditions for analytical RP-HPLC were as follows: a sample injection volume of 5 μL; mobile phase: 0.05% trifluoroacetic acid (TFA)$_{(aq.)}$/100% acetonitrile (35:65, v/v); column flow rate: 0.75 mL/min; column oven temperature: 35° C.; and detection wavelength: 360 nm.

Semi-preparative RP-HPLC was performed using the following instruments: a Hitachi L-7400 UV detector, a Hitachi L-7150 pump, a Hitachi HPLC D-7000 system, a column oven (Super CO-150, Enshine, Taiwan), a guard column (SecurityGuard Cartridge C12, size: 10 mm×10 mm, Phenomenex, USA), and an analytical column (Synergi 4μ C12 80 Å, size: 10 mm×150 mm, Phenomenex, USA). Operation conditions for semi-preparative RP-HPLC were as follows: a sample injection volume of 250 μL; mobile phase, which was selected depending on experiment; column flow rate: 4.5 mL/min; column oven temperature: 27° C.; and detection wavelength: 360 nm.

Example 1

Analysis of an Acetone-Extracted Product from Gamboge Resin (TSB-14) by Analytical RP-HPLC An acetone-extracted product from gamboge resin, i.e., TSB-14, which was prepared according to Example 1 of U.S. Pat. No. 7,138,428 B2, was subjected to an analytical RP-HPLC analysis, so as to determine the chemical constituent(s) contained therein.

Briefly, 1.0 mg of the product TSB-14 was dissolved in 1 mL of acetone and then subjected to an analytical RP-HPLC analysis along the lines as described in the previous section of "General Procedures," and an elution profile as shown in FIG. 1 was obtained.

Referring to FIG. 1, 35 major peaks (numbered from 1 to 35) are present in the elution profile of the product TSB-14 within the retention time of 0 to 80 minutes. According to the results shown in FIG. 1, the applicants postulated that it might be possible to isolate 35 compounds from the product TSB-14. To verify this postulation, the product TSB-14 was subjected to the following experiments.

Example 2

Preparation of Purified Compounds from the Product TSB-14

A. Semi-Preparative RP-HPLC Analysis of the Product TSB-14

3 g of the product TSB-14 was dissolved in 30 mL of acetone/acetonitrile (v/v=1:9) and then subjected to a semi-preparative RP-HPLC analysis along the lines as described in the previous section of "General Procedures," in which a mobile phase containing 0.05% $TFA_{(aq.)}$/65% acetonitrile $_{(aq.)}$(35:65) was used. The elution profile thus obtained is shown in FIG. 2.

After comparing the two elution profiles shown in FIGS. 1 and 2, the major peaks 1-35 as identified in FIG. 1 were also identified in the elution profile of FIG. 2, which was subsequently divided into three regions, i.e., Region 1, which includes peaks 1-12 eluted at a retention time of 0 to 42 minutes; Region 2, which includes peaks 13 to 24 eluted at a retention time of 42 to 135 minutes; and Region 3, which includes peaks 25 to 35 eluted at a retention time of 135 to 280 minutes.

B. Preparation of Fractions 1-3

3 g of the product TSB-14 was subjected to a semi-preparative RP-HPLC analysis as described in the preceding section A, and three eluates that respectively correspond to Regions 1, 2 and 3 of the elution profile shown in FIG. 2 were collected and then respectively subjected to the following treatment: partitioning a collected eluate in $H_2O$ and ethyl acetate; after washing with $H_2O$ so as to remove TFA, the organic layer was dried on anhydrous $Na_2SO_4$, filtered, and the organic solvent was removed using a vacuum rotatory evaporator.

After the aforesaid treatment of the three collected eluates, three corresponding fractions 1-3 were obtained.

C. Semi-Preparative RP-HPLC Analysis of Fractions 1-3

100 mg of each of fractions 1-3 as obtained in the preceding section B was dissolved in 1 mL of acetone, followed by subjecting to a semi-preparative RP-HPLC analysis as described in the preceding section A. The elution profiles of fractions 1-3 thus obtained are shown in FIGS. 3-5.

After comparing FIGS. 3, 4 and 5 with FIG. 2, it can be clearly seen that peaks 1-12, peaks 13-24 and peaks 25-35 are present in the semi-preparative RP-HPLC elution profiles of fractions 1, 2 and 3, respectively.

D. Preparation of Purified Compounds from Fraction 1

100 mg of fraction 1 as obtained in the preceding section B was dissolved in 1 mL of acetone, followed by subjecting to a semi-preparative RP-HPLC analysis as described in the preceding section A, in which eluates 1-12 that respectively correspond to the elution peaks 1-12 in the semi-preparative RP-HPLC elution profile of fraction 1 as shown in FIG. 3, were collected.

In order to obtain eluates 1-12 in large amount, elution of fraction 1 by the semi-preparative RP-HPLC analysis as described above was repeated for 50 to 100 times. Eluates 1-12 thus collected were individually placed into a 4 L brown glass bottle, followed by concentrating in a vacuum rotatory evaporator, to thereby give concentrates 1-12, each of which was in turn treated as follows: partitioning a concentrate in $H_2O$ and ethyl acetate; after washing with $H_2O$ so as to remove TFA, the organic layer was dried on anhydrous $Na_2SO_4$, filtered, and the organic solvent was removed using a vacuum rotatory evaporator.

After the aforesaid treatment of concentrates 1-12, twelve crude products were obtained, each of which was further purified as follows: 100 mg of a crude product was dissolved in 1.0 mL of acetone and then subjected to an analytical RP-HPLC analysis along the lines as described in the previous section of "General Procedures," so that an analytical RP-HPLC elution profile containing only a single elution peak was obtained. If the obtained elution profile failed to show the presence of a single peak, the remainder of said crude product was subjected to further purification by repeating the above-described treatments until an analytical RP-HPLC elution profile showing a single peak was obtained.

After completion of purification, twelve purified products were obtained from the eluates 1-12 of fraction 1 and were designated as Gh-3261, Gh-3271, Gh-3272, Gh-3311, Gh-3332, Gh-1036, Gh-3291, Gh-631, Gh-1052, Gh-3351, Gh-3353 and Gh-3352, respectively. The obtained weights of these twelve purified products are summarized in Table 1.

TABLE 1

The weights of twelve purified products from fraction 1.

| Eluate/Peak | Product | Weight (mg) |
| --- | --- | --- |
| 1 | Gh-3261 | 9 |
| 2 | Gh-3271 | 8 |
| 3 | Gh-3272 | 7 |
| 4 | Gh-3311 | 7 |
| 5 | Gh-3332 | 6 |
| 6 | Gh-1036 | 10 |
| 7 | Gh-3291 | 7 |
| 8 | Gh-631 | 12 |
| 9 | Gh-1052 | 6 |
| 10 | Gh-3351 | 9 |
| 11 | Gh-3353 | 7 |
| 12 | Gh-3352 | 5 |

E. Preparation of Purified Compounds from Fraction 2

100 mg of fraction 2 as obtained in the preceding section B was dissolved in 1 mL of acetone, followed by subjecting to a semi-preparative RP-HPLC analysis as described in the preceding section A, in which eluates 13-24 that respectively correspond to the elution peaks 13-24 in the semi-preparative RP-HPLC elution profile of fraction 2 as shown in FIG. 4, were collected.

In order to obtain eluates 13-24 in large amount, elution of fraction 2 by the semi-preparative RP-HPLC analysis as described above was repeated for 50 to 100 times. Eluates 13-24 thus collected were individually placed into a 4 L brown glass bottle, followed by concentrating in a vacuum rotatory evaporator, to thereby give concentrates 13-24, each of which was in turn subjected to partitioning separation and purification according to the procedures as described in the preceding section D.

After completion of purification, twelve purified products were obtained from the eluates 13-24 of fraction 2 and were designated as Gh-47, Gh-4602, Gh-4601, Gh-1601-A, Gh-1050, Gh-1602, Gh-1631, Gh-2641-1, Gh-2501, Gh-2642, Gh-2507 and Gh-2505, respectively. The obtained weights of these twelve purified products are summarized in Table 2.

TABLE 2

The weights of twelve purified products from fraction 2.

| Eluate/Peak | Product | Weight (mg) |
|---|---|---|
| 13 | Gh-47 | 14 |
| 14 | Gh-4602 | 48 |
| 15 | Gh-4601 | 27 |
| 16 | Gh-1601-A | 20 |
| 17 | Gh-1050 | 16 |
| 18 | Gh-1602 | 16 |
| 19 | Gh-1631 | 19 |
| 20 | Gh-2641-1 | 17 |
| 21 | Gh-2501 | 13 |
| 22 | Gh-2642 | 19 |
| 23 | Gh-2507 | 8 |
| 24 | Gh-2505 | 56 |

F. Preparation of Purified Compounds from Fraction 3

100 mg of fraction 3 as obtained in the preceding section B was dissolved in 1 mL of acetone, followed by subjecting to a semi-preparative RP-HPLC analysis as described in the preceding section A, in which eluates 25-35 that respectively correspond to the elution peaks 25-35 in the semi-preparative RP-HPLC elution profile of fraction 3 as shown in FIG. 5, were collected.

In order to obtain eluates 25-35 in large amount, elution of fraction 3 by the semi-preparative RP-HPLC analysis as described above was repeated for 50 to 100 times. Eluates 25-35 thus collected were individually placed into a 4 L brown glass bottle, followed by concentrating in a vacuum rotatory evaporator, to thereby give concentrates 25-35, each of which was in turn subjected to partitioning separation and purification according to the procedures as described in the preceding section D.

After completion of purification, eleven purified products were obtained from the eluates 25-35 of fraction 3 and were designated as Gh-2508, Gh-2603-1, Gh-2603-2, Gh-1641, Gh-1642, Gh-2605, Gh-2606, Gh-2607-B, Gh-2607-1A, Gh-2301 and Gh-4301, respectively. The obtained weights of these eleven purified products are summarized in Table 3.

TABLE 3

The weights of eleven purified products from fraction 3.

| Peak | Product | Weight (mg) |
|---|---|---|
| 25 | Gh-2508 | 18 |
| 26 | Gh-2603-1 | 16 |
| 27 | Gh-2603-2 | 18 |
| 28 | Gh-1641 | 20 |
| 29 | Gh-1642 | 25 |
| 30 | Gh-2605 | 162 |
| 31 | Gh-2606 | 124 |
| 32 | Gh-2607-B | 10 |
| 33 | Gh-2607-1A | 12 |
| 34 | Gh-2301 | 14 |
| 35 | Gh-4301 | 22 |

Example 3

Identification and Characterization of Compounds Isolated and Purified from Fractions 1-3

The physical and chemical properties of the thirty five products purified as obtained from fractions 1-3 in the above Example 2 were analyzed according to the methodologies set forth in the preceding section of "General Procedures," including melting point (mp) measurement, $^1$H-NMR, $^{13}$C-NMR, $^1$H-$^1$H COSY, HMQC, HMBC, NOESY, EIMS, HREIMS, FABMS, and HRFABMS. The experimental data thus obtained are summarized below.

1. Product Gh-47:

Product Gh-47, which was purified from eluate 13 of fraction 2, was determined to have the following properties:

Yellow flake crystals; mp 204~209° C.

EIMS m/z (relative intensity): 560 [M]$^+$ (100), 545 (47), 532 (22), 517 (36), 405 (44), 389 (11), 363 (24), 349 (17), 307 (12), 287 (22), 285 (16), 245 (15), 215 (12), 189 (5).

$^1$H-NMR (400 MHz, CDCl$_3$): δ 7.56 (1H, d, J=6.9 Hz), 6.63 (1H, d, J=9.6 Hz), 5.51 (1H, d, J=9.6 Hz), 5.12 (1H, dd, J=13.6, 6.8 Hz), 3.52 (1H, dd, J=6.2, 4.7 Hz), 3.26 (2H, d, J=7.4 Hz), 2.66 (1H, m), 2.55 (2H, m), 2.35 (1H, dd, J=13.4, 4.6 Hz), 1.75 (3H, s), 1.72 (3H, s), 1.65 (3H, s), 1.44 (3H, s), 1.43 (3H, s), 1.35 (3H, s), 1.30 (3H, s).

$^{13}$C-NMR (100 MHz, CDCl$_3$): δ 200.93, 178.91, 171.86, 161.10, 157.64, 157.28, 136.97, 135.39, 133.35, 131.70, 128.63, 126.18, 122.12, 115.44, 108.27, 103.18, 100.49, 90.71, 83.71, 83.64, 78.65, 49.06, 46.88, 29.95, 28.93, 28.33, 25.71, 25.31, 21.62, 18.09, 11.34.

According to the obtained spectral data, product Gh-47 was identified to be a known compound having the following chemical structure, i.e., isomorellic acid:

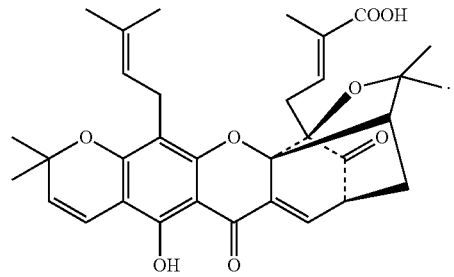

2. Product Gh-631:

Product Gh-631, which was purified from eluate 8 of fraction 1, was determined to have the following properties:

Yellow needle crystals; mp 115~118° C.

EIMS m/z (relative intensity): 394 [M]$^+$ (66), 393 (23), 379 (100), 339 (30), 323 (16), 311 (13), 295 (5), 278 (10), 203 (4), 162 (7).

$^1$H-NMR (600 MHz, acetone-d$_6$): δ 13.09 (1H, s, OH-1), 7.40 (1H, s, H-8), 6.55 (1H, d, J=10.0 Hz, H-11), 6.32 (1H, s, H-2), 5.87 (1H, d, J=10.0 Hz, H-12), 5.36 (H, m, H-17), 3.55 (2H, d, J=7.3 Hz, H-16), 1.84 (3H, s, H-20), 1.63 (3H, s, H-19), 1.48 (6H, s, H-14, H-15).

$^{13}$C-NMR (150 MHz, acetone-d$_6$): δ 181.24 (C=O), 163.41 (C-3), 162.26 (C-1), 155.56 (C-4a), 146.94 (C-6), 146.43 (C-10a), 134.42 (C-18), 132.30 (C-12), 131.77 (C-5), 123.33 (C-17), 122.08 (C-11), 119.03 (C-7), 115.20 (C-8a), 113.15 (C-8), 107.54 (C-4), 103.26 (C-9a), 98.40 (C-2), 78.84 (C-13), 28.26 (C-14, 15), 25.93 (C-19), 22.16 (C-16), 18.00 (C-20).

According to the obtained spectral data, product Gh-631 was identified to be a known compound having the following chemical structure, i.e., formoxanthone A:

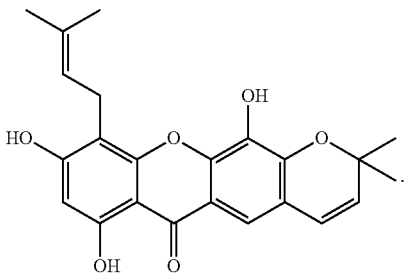 [SMILES: CC(C)=CCc1c(O)cc(O)c2c(=O)c3cc4c(c(O)c3oc12)OC(C)(C)C=C4]

3. Product Gh-4601:

Product Gh-4601, which was purified from eluate 15 of fraction 2, was determined to have the following properties:

Orange powder; mp 137~139° C.

EIMS m/z (relative intensity): 546 [M]$^+$ (100), 531 (18), 518 (44), 503 (40), 485 (9), 433 (7), 405 (33), 391 (10), 363 (19), 349 (13), 307 (10), 287 (25), 245 (8), 231 (18), 214 (12), 189 (5), 105 (6).

$^1$H-NMR (400 MHz, CDCl$_3$): δ 12.68 (1H, s), 7.41 (1H, d, J=7.2 Hz), 6.59 (1H, d, J=10.0 Hz), 5.49 (1H, d, J=10.0 Hz), 5.19 (1H, t, J=7.0 Hz), 4.73 (1H, t, J=8.0 Hz), 3.61 (2H, q, J=10.2 Hz), 3.49 (1H, d, J=4.7 Hz), 3.47 (1H, d, J=4.7 Hz), 3.32 (1H, dd, J=14.5, 6.8 Hz), 3.24 (1H, dd, J=14.3, 7.7 Hz), 2.60 (1H, d, J=7.7 Hz), 2.48 (1H, d, J=9.4 Hz), 2.31 (1H, dd, J=13.5, 4.7 Hz), 1.74, 1.68, 1.64, 1.25, 1.01 (each 3H, s), 1.41 (6H, s).

$^{13}$C-NMR (100 MHz, CDCl$_3$): δ 203.35, 180.33, 161.06, 157.80, 157.44, 138.01, 134.40, 133.63, 131.87, 126.31, 121.90, 118.20, 115.50, 108.44, 103.00, 100.72, 90.48, 84.50, 83.41, 78.66, 67.92, 49.09, 47.00, 30.09, 28.96, 28.28, 28.21, 25.71, 25.29, 21.57, 18.14, 12.49.

According to the obtained spectral data, product Gh-4601 was identified to be a known compound having the following chemical structure, i.e., isomorellinol:

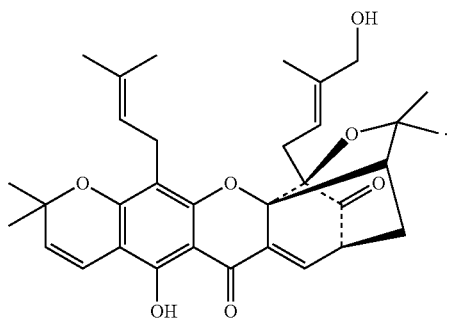

4. Product Gh-4602:

Product Gh-4602, which was purified from eluate 14 of fraction 2, was determined to have the following properties:

Orange powder; mp 106~109° C.

EIMS m/z (relative intensity): 560 [M]$^+$ (100), 545 (56), 532 (63), 517 (48), 487 (12), 433 (9), 405 (81), 391 (22), 363 (38), 349 (24), 307 (18), 287 (64), 245 (40), 231 (21), 215 (20), 189 (10).

$^1$H-NMR (400 MHz, CDCl$_3$): δ 12.71 (1H, s), 7.51 (1H, d, J=6.8 Hz), 6.49 (1H, d, J=10.0 Hz), 6.05 (1H, t, J=7.0 Hz), 5.39 (1H, d, J=10.0 Hz), 4.99 (1H, d, J=6.0 Hz), 3.45 (1H, dd, J=6.4, 4.7 Hz), 3.27 (1H, m), 3.08 (1H, m), 2.97 (2H, sept, J=8.0 Hz), 2.49 (1H, d, J=9.3 Hz), 2.28 (1H, dd, J=13.4, 4.5 Hz), 1.70, 1.69, 1.67, 1.60, 1.36, 1.34, 1.26 (each 3H, s).

$^{13}$C-NMR (100 MHz, CDCl$_3$): δ 203.47, 179.07, 171.74, 161.22, 157.65, 157.34, 138.46, 135.39, 133.42, 131.46, 127.64, 126.00, 122.22, 115.44, 108.04, 103.16, 100.55, 90.93, 83.82, 78.55, 49.01, 46.80, 29.87, 29.26, 28.82, 28.40, 28.20, 25.68, 25.14, 21.57, 20.63, 18.06.

According to the obtained spectral data, product Gh-4602 was identified to be a known compound having the following chemical structure, i.e., morellic acid:

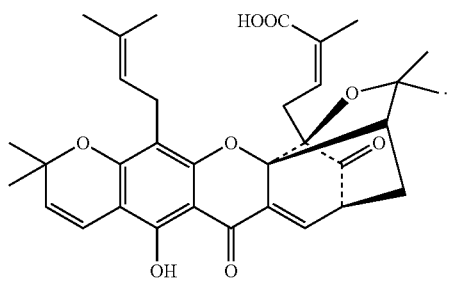

5. Product Gh-2301:

Product Gh-2301, which was purified from eluate 34 of fraction 3, was determined to have the following properties:

Orange needle crystals, mp 109~110° C.

EIMS m/z (relative intensity): 530 [M]$^+$ (100), 515 (22), 502 (92), 488 (30), 487 (83), 459 (11), 433 (20), 405 (49), 391 (15), 363 (24), 349 (16), 307 (13), 287 (27), 231 (13), 215 (37), 189 (6).

$^1$H-NMR (400 MHz, CDCl$_3$): δ 12.89 (1H, s), 7.45 (1H, d, J=7.2 Hz), 7.27 (1H, s), 6.65 (1H, d, J=10.4 Hz), 5.53 (1H, d, J=9.6 Hz), 5.30 (1H, br d, J=6.0 Hz), 4.43 (1H, br s), 3.49 (1H, m), 3.32 (2H, m), 2.50 (2H, m), 2.34 (1H, m), 1.78, 1.71, 1.68, 1.59, 1.33, 1.03 (each 3H, s), 1.45 (6H, s).

According to the obtained spectral data, product Gh-2301 was identified to be a known compound having the following chemical structure, i.e., desoxymorellin:

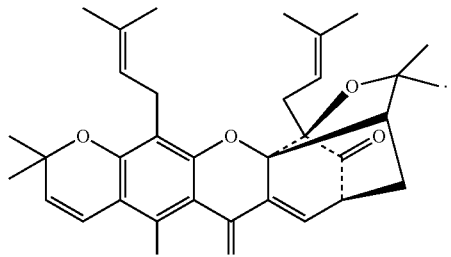

6. Product Gh-4301:

Product Gh-4301, which was purified from eluate 35 of fraction 3, was determined to have the following properties:

Yellow gummy solid; mp 85~88° C.

EIMS m/z (relative intensity): 600 [M]$^+$ (100), 572 (77), 557 (21), 531 (10), 503 (60), 475 (26), 449 (33), 393 (9), 357 (12), 351 (26), 323 (9), 309 (16), 295 (45), 281 (12), 253 (53), 231 (18), 215 (40), 189 (10), 177 (18), 173 (12), 69 (65).

$^1$H-NMR (600 MHz, CDCl$_3$): δ 12.92 (1H, s), 7.41 (1H, d, J=7.0 Hz), 6.45 (1H, s), 5.19 (2H, m), 5.03 (1H, m), 4.39

(1H, m), 3.45 (1H, dd, J=6.9, 4.5 Hz), 3.36 (4H, m), 2.52 (2H, m), 2.43 (1H, d, J=9.4 Hz), 2.30 (1H, dd, J=13.5, 4.7 Hz), 2.05 (4H, m), 1.78 (3H, s), 1.74 (3H, s), 1.69 (3H, s), 1.654 (3H, s), 1.645 (3H, s), 1.56 (3H, s), 1.33 (3H, s), 1.30 (1H, m), 1.25 (3H, s), 0.98 (3H, s).

$^{13}$C-NMR (150 MHz, CDCl$_3$): δ 203.55, 179.65, 162.98, 160.12, 156.29, 139.04, 134.91, 133.88, 133.80, 133.75, 131.88, 123.74, 121.86, 121.33, 117.76, 107.13, 106.39, 100.70, 90.12, 84.50, 83.11, 49.06, 46.90, 39.66, 30.03, 29.02, 28.78, 26.32, 25.70, 25.63, 25.49, 25.40, 22.05, 21.11, 18.01, 17.63, 16.68, 16.19.

According the obtained spectral data, product Gh-4301 was identified to be a known compound having the following chemical structure, i.e., desoxygambogenin:

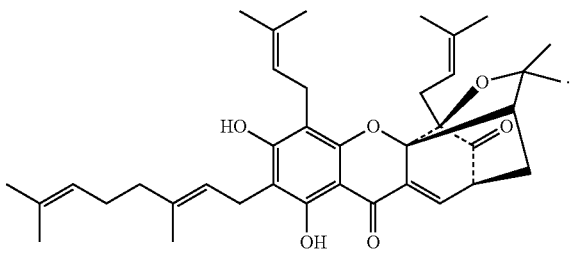

7. Product Gh-2605:

Product Gh-2605, which was purified from eluate 30 of fraction 3, was determined to have the following properties:

Yellow powder; mp 205~208° C.

EIMS m/z (relative intensity): 628 [M]$^+$ (22), 600 (15), 545 (100), 517 (23), 473 (17), 431 (7), 389 (9), 355 (10), 295 (5), 271 (7), 245 (14), 215 (23), 189 (11), 69 (9).

$^1$H-NMR (600 MHz, CDCl$_3$): δ 12.73 (1H, s), 7.52 (1H, d, J=6.9 Hz), 6.57 (1H, d, J=10.2 Hz), 6.08 (1H, dt, J=7.5, 1.3 Hz), 5.35 (1H, d, J=10.2 Hz), 5.01 (2H, m), 3.46 (1H, dd, J=6.8, 4.6 Hz), 3.27 (1H, dd, J=14.7, 8.1 Hz), 3.12 (1H, br dd, J=14.7, 5.3 Hz), 2.93 (2H, t, J=7.3 Hz), 2.49 (1H, d, J=9.3 Hz), 2.29 (1H, dd, J=13.4, 4.7 Hz), 1.98 (2H, m), 1.72 (3H, d, J=1.3 Hz), 1.71 (1H, m), 1.70 (3H, s), 1.67 (3H, s), 1.62 (3H, s), 1.60 (3H, s), 1.56 (1H, m), 1.52 (3H, s), 1.35 (3H, s), 1.34 (1H, m), 1.27 (3H, s).

$^{13}$C-NMR (150 MHz, CDCl$_3$): δ 203.28, 178.85, 170.88, 161.49, 157.55, 157.35, 137.90, 135.31, 133.34, 131.77, 131.49, 127.70, 124.49, 123.83, 122.25, 115.87, 107.60, 102.73, 100.44, 90.91, 83.92, 83.78, 81.28, 49.00, 46.81, 41.97, 29.85, 29.26, 28.84, 27.69, 25.64, 25.62, 25.16, 22.73, 21.60, 20.73, 18.06, 17.60.

According the obtained spectral data, product Gh-2605 was identified to be a known compound having the following chemical structure, i.e., gambogic acid:

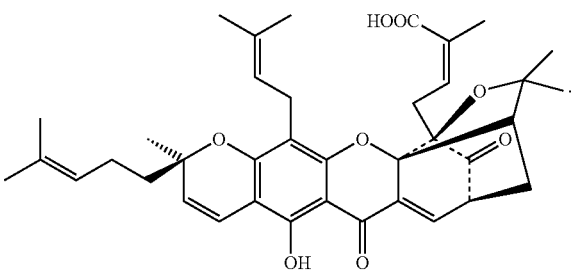

8. Product Gh-2606:

Product Gh-2606, which was purified from eluate 31 of fraction 3, was determined to have the following properties:

Yellow powder; mp 88-92° C.

EIMS m/z (relative intensity): 628 [M]$^+$ (24), 600 (11), 545 (100), 517 (21), 473 (12), 431 (4), 389 (8), 347 (6), 245 (7), 215 (14), 189 (5), 69 (4).

$^1$H-NMR (600 MHz, CDCl$_3$): δ 12.74 (1H, s), 7.53 (1H, d, J=6.9 Hz), 6.56 (1H, d, J=10.0 Hz), 6.10 (1H, dt, J=7.4, 1.2 Hz), 5.38 (1H, d, J=10.0 Hz), 5.07 (1H, br t, J=7.1 Hz), 5.01 (1H, br t, J=6.3 Hz), 3.45 (1H, dd, J=6.5, 4.9 Hz), 3.29 (1H, dd, J=14.6, 8.3 Hz), 3.13 (1H, br dd, J=14.6, 4.3 Hz), 2.94 (1H, dd, J=16.1, 7.7 Hz), 2.87 (1H, dd, J=16.3, 6.3 Hz), 2.49 (1H, d, J=9.3 Hz), 2.28 (1H, dd, J=13.4, 4.7 Hz), 2.05 (2H, m), 1.75 (1H, m), 1.72 (3H, s), 1.71 (3H, s), 1.68 (3H, s), 1.64 (3H, s), 1.62 (1H, m), 1.61 (3H, s), 1.55 (3H, s), 1.35 (1H, m), 1.31 (3H, s), 1.26 (3H, s).

$^{13}$C-NMR (150 MHz, CDCl$_3$): δ 203.25, 178.92, 170.68, 161.33, 157.59, 157.33, 137.73, 135.51, 133.21, 131.99, 131.39, 127.76, 124.76, 123.82, 122.24, 115.88, 107.79, 102.88, 100.51, 90.98, 83.86, 83.67, 81.10, 49.00, 46.82, 41.69, 29.91, 29.26, 28.78, 26.91, 25.67, 25.60, 25.20, 22.73, 21.61, 20.71, 18.12, 17.58.

According to the obtained spectral data, product Gh-2606 was identified to be a known compound having the following chemical structure, i.e., epigambogic acid:

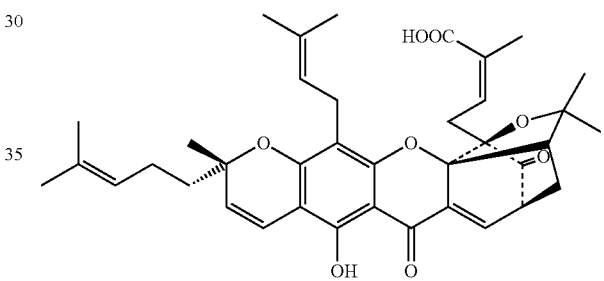

9. Product Gh-1641:

Product Gh-1641, which was purified from eluate 28 of fraction 3, was determined to have the following properties:

Yellow powder; mp 53~56° C.

EIMS m/z (relative intensity): 628 [M]$^+$ (32), 600 (6), 545 (100), 517 (12), 473 (6), 431 (2), 389 (4), 355 (5), 245 (8), 215 (11), 189 (3), 69 (5).

$^1$H-NMR (600 MHz, CDCl$_3$): δ 12.75 (1H, s), 7.53 (1H, d, J=6.9 Hz), 6.65 (1H, d, J=10.1 Hz), 6.61 (1H, t, J=7.5 Hz), 5.41 (1H, d, J=10.1 Hz), 5.09 (1H, t, J=6.9 Hz), 5.04 (1H, t, J=7.8 Hz), 3.49 (1H, dd, J=6.7, 4.6 Hz), 3.24 (2H, m), 2.63 (1H, dd, J=15.6, 8.2 Hz), 2.53 (1H, m), 2.51 (1H, d, J=9.3 Hz), 2.32 (1H, dd, J=13.5, 4.7 Hz), 2.02 (2H, dd, J=15.8, 7.7 Hz), 1.76 (1H, m), 1.70 (3H, s), 1.69 (3H, s), 1.63 (3H, s), 1.62 (3H, s), 1.59 (1H, m), 1.53 (3H, s), 1.38 (3H, s), 1.37 (1H, m), 1.34 (3H, s), 1.28 (3H, s).

$^{13}$C-NMR (150 MHz, CDCl$_3$): δ 202.97, 178.81, 171.55, 161.41, 157.61, 157.35, 136.98, 135.31, 133.36, 131.81, 131.75, 128.56, 124.77, 123.82, 122.18, 115.93, 107.92, 102.82, 100.40, 90.71, 83.73, 83.65, 81.33, 49.05, 46.87, 41.92, 29.93, 29.05, 28.95, 27.49, 25.67, 25.61, 25.33, 22.75, 21.61, 18.08, 17.59, 11.39.

According to the obtained spectral data, product Gh-1641 was identified to be a known compound having the following chemical structure, i.e., isogambogic acid:

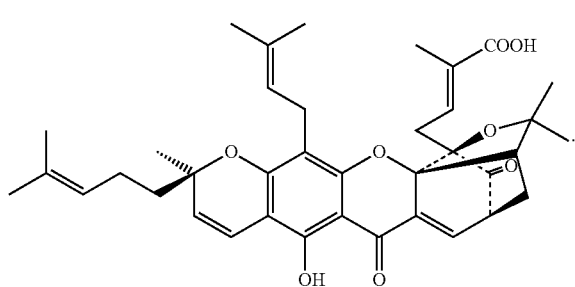

10. Product Gh-1642:

Product Gh-1642, which was purified from eluate 29 of fraction 3, was determined to have the following properties:

Yellow powder; mp 55~60° C.

EIMS m/z (relative intensity): 628 [M]$^+$ (63), 600 (13), 545 (100), 517 (17), 473 (17), 431 (8), 389 (7), 355 (7), 245 (8), 215 (10), 189 (3), 69 (18).

$^1$H-NMR (600 MHz, CDCl$_3$): δ 12.74 (1H, s), 7.52 (1H, d, J=7.1 Hz), 6.66 (1H, d, J=10.2 Hz), 6.50 (1H, t, J=7.9 Hz), 5.44 (1H, d, J=10.2 Hz), 5.12 (1H, t, J=6.9 Hz), 5.06 (1H, t, J=7.8 Hz), 3.49 (1H, dd, J=6.8, 4.5 Hz), 3.25 (2H, m), 2.61 (2H, m), 2.49 (1H, d, J=9.5 Hz), 2.32 (1H, dd, J=13.3, 4.7 Hz), 2.06 (2H, m), 1.78 (1H, m), 1.73 (3H, s), 1.70 (3H, s), 1.64 (3H, s), 1.63 (3H, s), 1.62 (1H, m), 1.55 (3H, s), 1.36 (3H, s), 1.34 (1H, m), 1.28 (3H, s), 1.23 (3H, s).

$^{13}$C-NMR (150 MHz, CDCl$_3$): δ 202.92, 178.88, 170.95, 161.32, 157.63, 157.36, 136.75, 135.31, 133.33, 131.97, 131.74, 128.81, 124.81, 123.76, 122.14, 115.96, 107.92, 102.93, 100.49, 90.64, 83.67, 83.62, 81.29, 49.07, 46.95, 41.88, 30.03, 29.06, 28.98, 27.32, 25.71, 25.64, 25.48, 22.75, 21.65, 18.16, 17.62, 11.43.

According to the obtained spectral data, product Gh-1642 was identified to be a known compound having the following chemical structure, i.e., epiisogambogic acid:

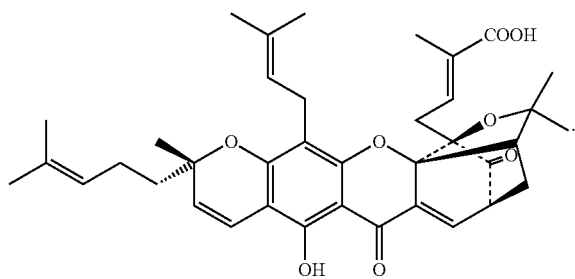

11. Product Gh-2603-2:

Product Gh-2603-2, which was purified from eluate 27 of fraction 3, was determined to have the following properties:

Yellow powder; mp 131~135° C.

EIMS m/z (relative intensity): 628 [M]$^+$ (92), 600 (91), 545 (54), 517 (46), 474 (100), 473 (88), 459 (18), 431 (29), 417 (15), 391 (33), 355 (37), 349 (25), 295 (18), 253 (21), 245 (25), 215 (30), 189 (18), 69 (20).

$^1$H-NMR (600 MHz, CDCl$_3$): δ 12.62 (1H, s, OH-6), 7.47 (1H, d, J=6.9 Hz, H-10), 6.00 (1H, dd, J=7.6, 1.3 Hz, H-27), 5.04 (1H, t, J=6.9 Hz, H-32), 4.53 (1H, s, H$_1$-40), 4.19 (1H, s, H$_2$-40), 3.43 (1H, dd, J=13.4, 4.6 Hz, H-11), 3.40 (1H, br s, H-4), 3.23 (1H, dd, J=14.5, 8.1 Hz, H$_1$-31), 3.10 (1H, dd, J=14.5, 5.6 Hz, H$_2$-31), 2.94 (2H, d, J=7.5 Hz, H-26), 2.51 (1H, d, J=9.3 Hz, H-22), 2.28 (1H, dd, J=13.4, 4.7 Hz, H$_1$-21), 2.08 (1H, br d, J=12.6 Hz, H-37), 1.88 (1H, br d, J=13.6 Hz, H$_1$-20), 1.82 (3H, s, H-39), 1.77 (1H, dd, J=13.1, 2.8 Hz, H$_1$-3), 1.71 (1H, m, H$_2$-3), 1.70 (3H, s, H-34), 1.69 (3H, s, H-25), 1.68 (3H, s, H-29), 1.62 (3H, s, H-35), 1.52 (1H, dt, J=13.4, 4.9 Hz, H$_2$-20), 1.36 (1H, m, H$_1$-36), 1.33 (1H, m, H$_2$-21), 1.30 (3H, s, H-19), 1.29 (1H, m, H$_2$-36), 1.27 (3H, s, H-24).

$^{13}$C-NMR (150 MHz, CDCl$_3$): δ 203.68 (C-12), 178.47 (C-8), 171.33 (C-30), 164.44 (C-18), 160.77 (C-6), 155.27 (C-16), 148.87 (C-38), 138.06 (C-27), 134.30 (C-10), 133.93 (C-9), 131.07 (C-33), 127.77 (C-28), 122.44 (C-32), 108.60 (C-40), 106.26 (C-17), 104.14 (C-5), 99.57 (C-7), 90.42 (C-14), 84.20 (C-23), 83.93 (C-13), 77.05 (C-2), 48.91 (C-22), 48.10 (C-37), 46.73 (C-11), 39.27 (C-20), 36.52 (C-3), 29.90 (C-25), 29.18 (C-26), 28.85 (C-4), 28.85 (C-24), 28.37 (C-19), 25.74 (C-35), 25.18 (C-21), 22.96 (C-39), 22.78 (C-36), 21.84 (C-31), 20.71 (C-29), 18.14 (C-34).

The EIMS data of Product Gh-2603-2 show a molecular ion peak [M]$^+$ at m/z 628, which is identical to that observed in gambogic acid. In addition, the recorded $^1$H-NMR and $^{13}$C-NMR data of Product Gh-2603-2 were found to be identical to those of a known compound, i.e., gambogellic acid, as further confirmed by the $^1$H-$^1$H COSY, HMQC (J=150 Hz) and HMBC (J=8 Hz) spectral analyses (data not shown).

The NOESY data of Product Gh-2603-2 also reveal that δ 7.47 (H-10) was correlated with δ 3.43 (H-11); δ 3.43 (H-11) was correlated with δ 2.28 (H$_1$-21); δ 1.33 (H$_2$-21) was correlated with δ 2.51 (H-22); δ 2.28 (H$_1$-21) was correlated with δ 2.51 (H-22) and δ 1.27 (H-24); and δ 6.00 (H-27) was correlated with δ 1.68 (H-29), evidencing that the stereostructure of Product Gh-2603-2 in this part is identical to that of gambogic acid. Namely, the stereostructure of Product Gh-2603-2 in this part has a 11S,13R,14S,22S configuration, which includes H-27 and carboxyl group (C-30) in a trans relationship, and a double bond Δ$^{27,28}$ in a Z configuration.

In the monoterpene moiety of Product Gh-2603-2, the signal of the methine proton attached to the isopropenyl group (i.e., δ 2.08 (1H, br d, J=12.6 Hz, H-37)) reveals that the methine proton attached to the isopropenyl group and a vicinal proton have a relatively high vicinal coupling constant (J=12.6 Hz) and, hence, they are in axial-axial coupling. As such, H-37 is in an axial orientation.

It was further found from the NOESY data of Product Gh-2603-2 that: δ 3.40 (144) was correlated not only with δ 2.08 (H-37), but also with δ 1.77 (H$_1$-3) and δ 1.71 (H$_2$-3); δ 1.77 (H$_1$-3) was correlated with δ 1.30 (H-19); δ 2.08 (H-37) was correlated with δ 1.77 (H$_1$-3) and δ 1.52 (H$_2$-20); and δ 3.40 (H-4) was correlated with δ 1.68 (H-29). Since δ 3.40 (H-4) was correlated with δ 1.68 (H-29), C-2 was in a R configuration. The monoterpene moiety of Product Gh-2603-2 was determined to have a rigid chair conformation, in which an 1,3-diaxial interaction exists amongst H-37, H-3, and H-20; the methyl proton (H-19) attached to C-2 and the isopropenyl group attached to C-37 were in an equatorial orientation, so that the stereostructure of Product Gh-2603-2 in this part has a 2R,4R,37S configuration.

Based on the above information, Product Gh-2603-2 was identified to be a known compound having the following chemical structure, i.e., gambogellic acid:

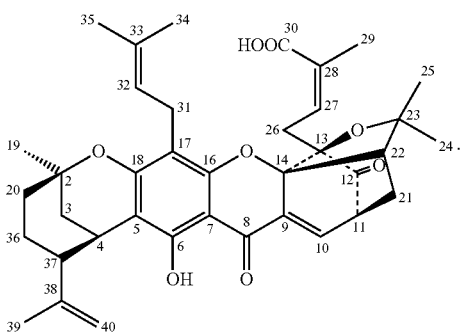

12. Product Gh-2603-1:

Product Gh-2603-1, which was purified from eluate 26 of fraction 3, was determined to have the following properties:

Yellow powder; mp 115~120° C.

EIMS m/z (relative intensity): 628 [M]$^+$ (92), 600 (100), 545 (68), 517 (49), 474 (98), 473 (80), 459 (17), 431 (25), 417 (13), 391 (28), 355 (24), 349 (18), 295 (11), 253 (12), 245 (13), 215 (16), 189 (7), 69 (15).

$^1$H-NMR (600 MHz, CDCl$_3$): δ 12.68 (1H, s, OH-6), 7.48 (1H, d, J=6.9 Hz, H-10), 5.99 (1H, dt, J=8.0, 1.3 Hz, H-27), 5.00 (1H, br t, J=6.7 Hz, H-32), 4.52 (1H, s, H$_1$-40), 4.26 (1H, s, H$_2$-40), 3.50 (1H, br s, H-4), 3.44 (1H, dd, J=6.8, 4.5 Hz, H-11), 3.31 (1H, dd, J=14.6, 8.2 Hz, H$_1$-31), 3.20 (1H, br dd, J=14.5, 3.8 Hz, H$_2$-31), 3.01 (1H, dd, J=16.5, 7.6 Hz, H$_1$-26), 2.84 (1H, ddd, J=16.6, 7.1, 1.4 Hz, H$_2$-26), 2.46 (1H, d, J=9.4 Hz, H-22), 2.29 (1H, dd, J=13.5, 4.6 Hz, H$_1$-21), 2.13 (1H, br d, J=12.4 Hz, H-37), 1.92 (1H, br dd, J=13.8, 2.0 Hz, H$_1$-20), 1.86 (1H, dd, J=6.6, 2.7 Hz, H$_1$-3), 1.84 (3H, s, H-39), 1.70 (1H, m, H$_2$-3), 1.695 (3H, s, H-34), 1.69 (6H, s, H-25, H-29), 1.61 (3H, s, H-35), 1.54 (1H, dt, J=13.5, 5.2 Hz, H$_2$-20), 1.36 (2H, m, H-36), 1.34 (1H, m, H$_2$-21), 1.33 (3H, s, H-19), 1.27 (3H, s, H-24).

$^{13}$C-NMR (150 MHz, CDCl$_3$): δ 203.23 (C-12), 178.53 (C-8), 170.69 (C-30), 164.50 (C-18), 160.92 (C-6), 155.39 (C-16), 147.30 (C-38), 137.10 (C-27), 134.59 (C-10), 133.70 (C-9), 131.11 (C-33), 128.00 (C-28), 122.59 (C-32), 109.28 (C-40), 106.34 (C-17), 104.24 (C-5), 99.48 (C-7), 90.48 (C-14), 83.90 (C-23), 83.61 (C-13), 77.09 (C-2), 49.13 (C-22), 48.32 (C-37), 46.74 (C-11), 39.33 (C-20), 37.13 (C-3), 29.89 (C-25), 29.50 (C-26), 29.09 (C-4), 28.95 (C-24), 28.52 (C-19), 25.69 (C-35), 25.41 (C-21), 22.93 (C-39), 22.69 (C-36), 21.90 (C-31), 20.56 (C-29), 18.16 (C-34).

The EIMS data of product Gh-2603-1 show a molecular ion peak [M]$^+$ at m/z 628, which reveals that the fragmentation pattern of Product Gh-2603-1 is identical to that of Product Gh-2603-2 gambogellic acid). Besides, the $^1$H-NMR and $^{13}$C-NMR data of Product Gh-2603-1 are generally similar to those of Product Gh-2603-2.

The $^1$H-NMR data of Product Gh-2603-1 show that the side chain connected to C-13 has a proton signal different from that observed in a corresponding site of Product Gh-2603-2. That is, in Product Gh-2603-2 the methylene proton in the 2-methyl-2-butenoic acid has a simple doublet signal of δ 2.94 (2H, d, J=7.5 Hz, H-26), whereas in Product Gh-2603-1 the methylene proton in the 2-methyl-2-butenoic acid has signals of δ 3.01 (1H, dd, J=16.5, 7.6 Hz, H$_1$-26) and 2.84 (1H, ddd, J=16.6, 7.1, 1.4 Hz, H$_2$-26). In the structure of gambogellic acid (Product Gh-2603-2) wherein C-2 is in a R configuration, the methylene group (C-26) is capable of free rotation. If C-2 is in a S configuration, the monoterpene p-menthene ring and the isopropenyl group containing C-2 form a steric hindrance to free rotation, thereby resulting in a nonequivalence of the two protons in the methylene group, as well as an anisotropic effect to relevant protons. Besides, the methine proton attached to the isopropenyl group, which has a signal of δ 2.13 (1H, br d, J=12.4 Hz, H-37), has a high coupling constant (J=12.4 Hz), indicating that the methine proton attached to the isopropenyl group is in an axial orientation.

The structure of Product Gh-2603-1 was further confirmed by the $^1$H-$^1$H COSY, HMQC and HMBC analyses, in which the HMBC data of the p-menthene monoterpene show that the exo-methylene protons (δ 4.52 (H$_1$-40) and δ 4.26 (H$_2$-40)) are correlated with δ 22.93 (C-39) and δ 48.32 (C-37); the C-3 methylene proton (δ 1.86 (H$_1$-3)) is correlated with δ 104.24 (C-5), δ 29.09 (C-4), δ 48.32 (C-37) and δ 147.30 (C-38); and the C-20 methylene proton (δ 1.92 (H$_1$-20)) is correlated with δ 48.32 (C-37) and δ 29.09 (C-4). Moreover, the methyl proton (δ 1.33 (H-19)) attached to C-2 are correlated with two adjacent methylene carbons (δ 37.13 (C-3) and δ 39.33 (C-20)).

The HMBC data of Product Gh-2603-1 also show that: H-3 is correlated with C-5 in the aromatic ring, and both the isopropenyl group attached to C-37 and the methyl proton (H-19) attached to C-2 are in an equatorial orientation. Therefore, the monoterpene moiety has a rigid chair conformation.

It is further found from the NOESY data of Product Gh-2603-1 that: δ 2.13 (H-37) is correlated with δ 1.36 (H-36) and δ 1.54 (H$_2$-20). This indicates that a 1,3-diaxial interaction exists amongst the axial H-37 and the two axial protons (H-3 and H-20) in the methylene group adjacent to C-2. Therefore, in contrast to Product Gh-2603-2, the p-menthene in Product Gh-2603-1 is in a 2S,4S,37R configuration. In addition, the NOESY data of Product Gh-2603-1 also shows that: δ 7.48 (H-10) is correlated with δ 3.44 (H-11); δ 3.44 (H-11) is correlated with δ 2.29 (H$_1$-21); δ 1.34 (H$_2$-21) is correlated with δ 2.46 (H-22); both δ 2.29 (H$_1$-21) and δ 2.46 (H-22) are correlated with δ 1.27 (H-24); and δ 5.99 (H-27) is correlated with δ 1.69 (H-29). These data evidence that the stereostructure of Product Gh-2603-1 at the right-side of the r-pyrone thereof is identical to that of gambogic acid or gambogellic acid, i.e., having a 11S,13R,14S,22S configuration, which includes H-27 and carboxyl group (C-30) in a trans relationship, and a double bond Δ$^{27,28}$ in a Z configuration.

Based on the above information, Product Gh-2603-1 was identified to be a known compound having the following chemical structure, i.e., "epigambogellic acid" {IUPAC nomenclature: [2-butenoic acid, 2-methyl-4-[(1R,3aS,5S, 9S,10R,13S,16aS)-3a,4,5,7,10,11,12,13-octahydro-8-hydroxy-3,3,13-trimethyl-15-(3-methyl-2-butenyl)-10-(1-methylethenyl)-7,18-dioxo-1,5:9,13-dimethano-1H,3H,9H-furo[3.4-g]oxocino[3.2-b]xanthen-1-yl]-,(2Z)-]}:

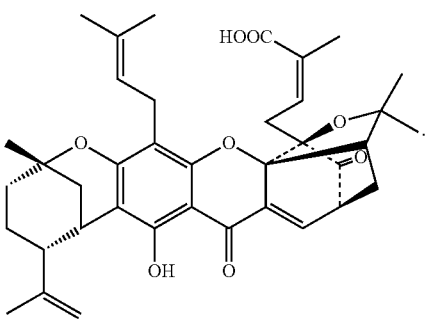

13. Product Gh-2607-B:

Product Gh-2607-B, which was purified from eluate 32 of fraction 3, was determined to have the following properties:

Yellow powder; mp 120-125° C.

EIMS m/z (relative intensity): 628 [M]$^+$ (33), 600 (17), 545 (100), 517 (23), 499 (4), 474 (14), 431 (5), 389 (8), 355 (7), 347 (6), 245 (5), 215 (9), 189 (3), 69 (4); HREIMS [M]$^+$ m/z: 628.3034; calculated for $C_{38}H_{44}O_8$, 628.3036.

$^1$H-NMR (600 MHz, CDCl$_3$): δ 12.57 (1H, s, OH-6), 7.50 (1H, d, J=6.9 Hz, H-10), 5.86 (1H, dt, J=7.6, 1.2 Hz, H-27), 5.10 (1H, br t, J=7.0 Hz, H-32), 3.46 (1H, dd, J=6.8, 4.5 Hz, H-11), 3.28 (1H, dd, J=14.7, 8.5 Hz, H$_1$-31), 3.15 (1H, m, H$_1$-26), 3.12 (1H, m, H$_2$-31), 2.95 (1H, d, J=9.6 Hz, H-3), 2.91 (1H, ddd, J=15.9, 6.9, 1.4 Hz, H$_2$-26), 2.50 (1H, d, J=9.3 Hz, H-22), 2.42 (1H, dd, J=9.5, 7.4 Hz, H-4), 2.31 (1H, m, H-37), 2.29 (1H, m, H$_1$-21), 1.74 (1H, m, H$_1$-20), 1.71 (3H, s, H-34), 1.69 (3H, s, H-25), 1.67 (3H, s, H-29), 1.60 (3H, s, H-35), 1.60 (1H, m, H$_1$-36), 1.53 (1H, m, H$_2$-20), 1.49 (1H, m, H$_2$-36), 1.36 (1H, m, H$_2$-21), 1.30 (3H, s, H-40), 1.28 (3H, s, H-19), 1.27 (3H, s, H-24), 0.71 (3H, s, H-39).

$^{13}$C-NMR (150 MHz, CDCl$_3$): δ 203.71 (C-12), 178.89 (C-8), 171.22 (C-30), 161.53 (C-18), 161.17 (C-6), 155.04 (C-16), 137.79 (C-27), 134.63 (C-10), 133.88 (C-9), 130.85 (C-33), 128.20 (C-28), 122.37 (C-32), 108.88 (C-17), 105.32 (C-5), 100.38 (C-7), 90.33 (C-14), 85.18 (C-2), 84.18 (C-23), 83.86 (C-13), 48.94 (C-22), 46.81 (C-11), 46.23 (C-37), 38.81 (C-38), 38.58 (C-20), 36.93 (C-4), 35.01 (C-3), 33.45 (C-40), 29.91 (C-25), 29.25 (C-26), 28.93 (C-24), 27.35 (C-19), 25.74 (C-35), 25.61 (C-36), 25.32 (C-21), 21.83 (C-31), 20.78 (C-29), 18.19 (C-34), 17.68 (C-39).

The EIMS data of Product Gh-2607-B show a molecular ion peak [M]$^+$ at m/z 628 and the HREIMS data of Product Gh-2607-B show a molecular ion peak [M]$^+$ at m/z 628.3034, indicating that Product Gh-2607-B has a molecular formula identical to those of the above-described compounds gambogic acid and gambogellic acid as well as their epimers, i.e., $C_{38}H_{44}O_8$.

The $^1$H-NMR and $^{13}$C-NMR data of Product Gh-2607-B show that Product Gh-2607-B does not have a disubstituted double bond in the pyran ring thereof, nor does it have an isopropenyl group having a terminal double bond.

As further confirmed by the $^1$H-$^1$H COSY, HMQC and HMBC analyses, Product Gh-2607-B is structurally similar to gambogellic acid except for at the monoterpene moiety. As compared to gambogellic acid, Product Gh-2607-B was found to have one less double bond. Product Gh-2607-B was therefore presumed to have one more ring than gambogellic acid.

The $^1$H-$^1$H COSY data of Product Gh-2607-B shows that: a methine proton having a doublet signal (δ 2.95 (1H, d, J=9.6 Hz, H-3)) is coupled to only another methine proton (δ 2.42 (1H, dd, J=9.5, 7.4 Hz, H-4)), which is further coupled to a further methine proton (δ 2.31 (1H, m, H-37)); the methine proton (δ 2.31 (1H, m, H-37)) is coupled to two methylene protons of C-36 (δ 1.60 (1H, m, H$_1$-36) and δ 1.49 (1H, m, H$_2$-36)); and a further methylene proton (δ 1.74 (1H, m, H$_1$-20)) is coupled to the two methylene protons of C-36 (δ 1.60 (1H, m, H$_1$-36) and δ 1.49 (1H, m, H$_2$-36)), evidencing that the monoterpene moiety of Product Gh-2607-B still has two adjacent methylene groups (C-36 (δ 25.61) and C-20 (δ 38.58)) and three adjacent methine groups (C-3 (δ 35.01), C-4 (δ 36.93), and C-37 (δ 46.23)]). The methine group (C-3) of Product Gh-2607-B is a transformation of the methylene group (C-3) of gambogellic acid, and said transformation is presumed to be caused by forming a bond between C-3 and C-38 to replace a terminal double bond between C-38 and C-40, thereby resulting in the formation of a pinane-type monoterpene structure, which includes a cyclobutane, a gem-dimethyl group (C-39 (δ 17.68) and C-40 (δ 33.45)), an oxygen-bearing quaternary carbon (C-2 (δ 85.18)), and a tertiary methyl group (C-19 (δ 27.35)) attached to the oxygen-bearing quaternary carbon.

The HMBC data of Product Gh-2607-B show that: in addition to being correlated with an aromatic carbon δ 105.32 (C-5), δ 161.17 (C-6) and δ 161.53 (C-18), δ 2.95 (H-3) is correlated with δ 85.18 (C-2), δ 46.23 (C-37), δ 38.81 (C-38), δ 38.58 (C-20), δ 36.93 (C-4), δ 33.45 (C-40), and δ 17.68 (C-39); δ 2.42 (H-4) is correlated with δ 105.32 (C-5), δ 85.18 (C-2), δ 38.81 (C-38), δ 35.01 (C-3), δ 27.35 (C-19) and δ 25.61 (C-36); and δ 2.31 (H-37) is correlated with δ 85.18 (C-2), δ 38.81 (C-38), δ 35.01 (C-3), δ 36.93 (C-4), and δ 33.45 (C-40). It can be known from the above HMBC data that: in the pinane-type monoterpene structure of Product Gh-2607-B, C-2 is connected to C-18 of an aromatic ring via an ether bond; C-4 is connected to C-5; and the methyl group (C-19) attached to C-2 is in an equatorial orientation.

It is further found from the NOESY data of Product Gh-2607-B that: δ 2.95 (H-3) is correlated with δ 2.42 (H-4), δ 1.28 (H-19) and δ 1.30 (H-40); δ 2.42 (H-4) is correlated with δ 2.31 (H-37) and δ 1.30 (H-40); δ 2.31 (H-37) is correlated with δ 1.30 (H-40); δ 0.71 (1439) is correlated with δ 1.30 (H-40), δ 1.28 (H-19), δ 1.74 (H$_1$-20) and δ 1.53 (H$_2$-20); and δ 1.67 (H-29) is correlated with δ 5.86 (H-27), but there is no cross peak between δ 1.67 (H-29), δ 2.42 (H-4) and δ 2.31 (H-37), indicating that C-2 is in an R configuration; the methyl group (C-19) is in a α-equatorial orientation; and in the pinane structure, the three methine protons H-3, H-4 and H-37 in the cyclobutane ring are in cis-relationship such that the cyclobutane ring is in a 3S,4S, 37R configuration.

The NOESY data of Product Gh-2607-B also reveal that: δ 7.50 (H-10) is correlated with δ 3.46 (H-11); δ 3.46 (H-11) is correlated with δ 2.29 (H$_1$-21); δ 1.36 (H$_2$-21) is correlated with δ 2.50 (H-22); and δ 2.50 (H-22) is correlated with δ 1.69 (H-25), evidencing that the stereostructure of Product Gh-2607-B in this part has a 11S,13R,14S,22S configuration, which includes H-27 and a carboxyl group (C-30) in a trans-relationship inasmuch as δ 1.67 (H-29) is correlated with δ 5.86 (H-27), and a double bond Δ$^{27,28}$ in a Z configuration.

Based on the above information, Product Gh-2607-B is identified to be a new compound having the following chemical structure:

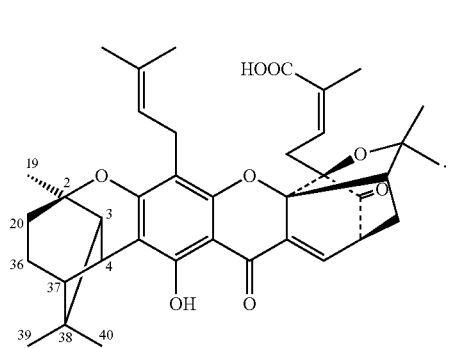

Product Gh-2607-B is identified by the name "formoxanthone B" {IUPAC nomenclature: [2-butenoic acid, 2-methyl-4-[(1R,3aS,5S,9S,10S,12R,15R,18aS)-3a,4,5,7, 12,13,14,15-octahydro-8-hydroxy-3,3,11,11,15-pentamethyl-[7-(3-methyl-2-butenyl)-7,19-dioxo-1,5-methano-1H,3H,9H-furo[3.4-g]-16-oxa-tricyclo[4.4.0.0$^{9,12}$]decano[3.2-b]xanthen-1-yl]-,(2Z)-]}.

14. Product Gh-2607-1A:

Product Gh-2607-1A, which was purified from eluate 14 of fraction 3, was determined to have the following properties:

Yellow powder; mp 146~151° C.

EIMS m/z (relative intensity): 628 [M]$^+$ (27), 601 (13), 545 (100), 517 (20), 473 (12), 389 (8), 355 (7), 347 (7), 245 (10), 215 (18), 189 (8), 69 (11); HREIMS [M$^+$] m/z: 628.3046; calculated for $C_{38}H_{44}O_8$, 628.3036.

$^1$H-NMR (600 MHz, CDCl$_3$): δ 12.55 (1H, s, OH-6), 7.49 (1H, d, J=6.9 Hz, H-10), 5.87 (1H, t, J=7.3 Hz, H-27), 5.00 (1H, br t, J=6.3 Hz, H-32), 3.46 (1H, t, J=5.6 Hz, H-11), 3.27 (1H, dd, J=14.3, 8.6 Hz, H$_1$-31), 3.17 (1H, dd, J=15.9, 8.4 Hz, H$_1$-26), 3.10 (1H, br dd, J=13.9, 4.4 Hz, H$_2$-31), 2.93 (1H, m, H-3), 2.92 (1H, m, H$_2$-26), 2.49 (1H, d, J=9.3 Hz, H-22), 2.40 (1H, t, J=8.4 Hz, H-4), 2.30 (1H, m, H-37), 2.28 (1H, m, H$_1$-21), 1.72 (1H, m, H$_1$-20), 1.70 (3H, s, H-34), 1.68 (3H, s, H-25), 1.66 (3H, s, H-29), 1.60 (3H, s, H-35), 1.58 (1H, m, H$_1$-36), 1.52 (1H, m, H$_2$-20), 1.50 (1H, m, H$_2$-36), 1.35 (1H, dd, J=13.3, 9.6 Hz, H$_2$-21), 1.28 (3H, s, H-19), 1.27 (6H, s, H-24, H-40), 0.69 (3H, s, H-39).

$^{13}$C-NMR (150 MHz, CDCl$_3$): δ 203.75 (C-12), 178.86 (C-8), 171.59 (C-30), 161.51 (C-18), 161.15 (C-6), 155.01 (C-16), 138.12 (C-27), 134.58 (C-10), 133.85 (C-9), 130.79 (C-33), 128.07 (C-28), 122.35 (C-32), 108.85 (C-17), 105.28 (C-5), 100.34 (C-7), 90.32 (C-14), 85.12 (C-2), 84.20 (C-23), 83.80 (C-13), 48.93 (C-22), 46.79 (C-11), 46.19 (C-37), 38.77 (C-38), 38.53 (C-20), 36.90 (C-4), 34.97 (C-3), 33.41 (C-40), 29.90 (C-25), 29.19 (C-26), 28.91 (C-24), 27.31 (C-19), 25.73 (C-35), 25.59 (C-36), 25.29 (C-21), 21.80 (C-31), 20.77 (C-29), 18.16 (C-34), 17.65 (C-39).

The EIMS data of Product Gh-2607-1A show a molecular ion peak [M]$^+$ at m/z 628 and the HREIMS data of Product Gh-2607-1A show a molecular ion peak [M]$^+$ at m/z 628.3046, indicating that Product Gh-2607-1A has a molecular formula identical to those of the above-described compounds gambogic acid and gambogellic acid as well as their epimers, $C_{38}H_{44}O_8$.

The $^1$H-NMR and $^{13}$C-NMR data of Product Gh-2607-1A show that Product Gh-2607-1A does not have a cis disubstituted double bond in the pyran ring thereof, nor does it have an isopropenyl group having a terminal double bond.

As further confirmed by the $^1$H-$^1$H COSY, HMQC and HMBC analyses, Product Gh-2607-1A is structurally similar to gambogellic acid except for at the monoterpene moiety. As compared to gambogellic acid, Product Gh-2607-1A was found to have one less double bond. Product Gh-2607-1A was therefore presumed to have one more ring than gambogellic acid.

The $^1$H-$^1$H COSY data of product Gh-2607-1A show that: a methine proton (δ 2.93 (1H, m, H-3)) is coupled to another methine proton (δ 2.40 (1H, t, J=8.4 Hz, H-4)); the methine proton δ 2.40 is coupled to a further methine proton (δ 2.30 (1H, m, H-37)); the methine proton δ 2.30 is coupled to one methylene proton (δ 1.50 (1H, m, H$_2$-36)) of C-36; and the other methylene proton (δ 1.58 (1H, m, H$_1$-36)) of C-36 is coupled to another methylene proton (δ 1.72 (1H, m, H$_1$-20)), evidencing that the monoterpene moiety of Product Gh-2607-1A has two adjacent methylene groups (C-20 (δ 38.53) and C-36 (δ 25.59)) and three adjacent methine groups (C-37 (δ 46.19), C-4 (δ 36.90) and C-3 (δ 34.97)). The methine group (C-3) of Product Gh-2607-1A is a transformation of the methylene group (C-3) of gambogellic acid, and said transformation is presumed to be caused by forming a bond between C-3 and C-38 to replace a terminal double bond between C-38 and C-40, thereby resulting in the formation of a pinane-type monoterpene structure, which includes a cyclobutane, a gem-dimethyl group (C-39 (δ 17.65) and C-40 (δ 33.41)), an oxygen-bearing quaternary carbon (C-2 (δ 85.12)), and a tertiary methyl group (C-19 (δ 27.31)) attached to the oxygen-bearing quaternary carbon.

The HMBC data of Product Gh-2607-1A show that: in addition to being correlated with aromatic ring carbons δ 105.28 (C-5), δ 161.15 (C-6) and δ 161.51 (C-18), δ 2.93 (H-3) is correlated with δ 85.12 (C-2), δ 46.19 (C-37), δ 38.77 (C-38), δ 38.53 (C-20), δ 36.90 (C-4), δ 33.41 (C-40) and δ 17.65 (C-39); δ 2.40 (H-4) is correlated with δ 105.28 (C-5), δ 38.77 (C-38), δ 34.97 (C-3), δ 46.19 (C-37), δ 25.59 (C-36), δ 38.53 (C-20) and δ 27.31 (C-19); and δ 2.30 (H-37) is correlated with δ 105.28 (C-5), δ 85.12 (C-2), δ 38.77 (C-38), δ 34.97 (C-3), δ 36.90 (C-4), δ 38.53 (C-20), δ 25.59 (C-36) and δ 33.41 (C-40). It can be known from the above HMBC data that in the pinane-type monoterpene structure of Product Gh-2607-1A, C-2 is connected to C-18 of an aromatic ring via an ether bond; C-4 is connected to C-5; and the methyl group (C-19) attached to C-2 is in an equatorial orientation.

The NOESY data of Product Gh-2607-1A show that: δ 7.49 (H-10) is correlated with δ 3.46 (H-11); δ 3.46 (H-11) is correlated with δ 2.28 (H$_1$-21); δ 1.35 (H$_2$-21) is correlated with δ 2.49 (H-22); δ 2.49 (H-22) is correlated with δ 1.68 (H-25); and δ 5.87 (H-27) is correlated with δ 1.66 (H-29), evidencing that the stereostructure of Product Gh-2607-1A in this part has a 11S,13R,14S,22S configuration, which includes H-27 and a carboxyl group (C-30) in a trans-relationship, and a double bond Δ$^{27,28}$ in a Z configuration. In addition, δ 2.93 (H-3) is correlated with δ 2.40 (H-4), δ 1.28 (H-19) and δ 1.27 (H-40); δ 2.40 (H-4) is correlated with δ 2.30 (H-37), δ 1.27 (H-40) and δ 1.66 (H-29); δ 2.30 (H-37) is correlated with δ 1.66 (H-29) and δ 1.70 (H-34); and δ 1.50 (H$_2$-36) is correlated with δ 1.66 (H-29). It can therefore be known that C-2 is in a S configuration; and in the pinane structure, the three methine protons H-3, H-4 and H-37 in the cyclobutane ring are in cis-relationship such that the cyclobutane ring is in a 3S,4S, 37R configuration. The NOESY data also reveal that: both δ 3.27 (H$_1$-31) and δ 3.10 (H$_2$-31) are correlated with δ 1.66 (H-29); both δ 3.17 (H$_1$-26) and δ 2.92 (H$_2$-26) are correlated with δ 1.70 (H-34); and δ 0.69 (H-39) is correlated with δ 1.72 (H$_1$-20), δ 1.28 (H-19) and δ 1.27 (H-40).

Based on the above information, Product Gh-2607-1A is identified to be a new compound having the following chemical structure:

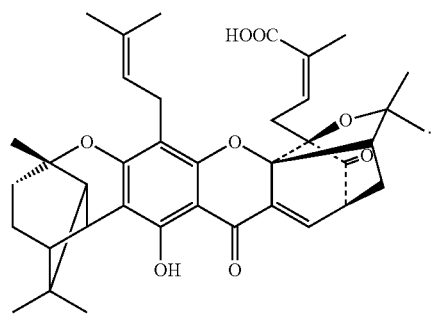

Product Gh-2607-1A is identified by the name "epiformoxanthone B" {IUPAC nomenclature: [2-butenoic acid, 2-methyl-4-[1R,3aS,5S,9R,10R,12S,15S,18aS)-3a,4,5,7,12,13,14,15-octahydro-8-hydroxy-3,3,11,11,15-pentamethyl-17-(3-methyl-2-butenyl)-7,19-dioxo-1,5-methano-1H,3H,9H-furo[3.4-g]-16-oxa-tricyclo[4.4.0.0$^{9,12}$]decano[3.2-b]xanthen-1-yl]-,(2Z)-]}.

15. Product Gh-2508:

Product Gh-2508, which was purified from eluate 25 of fraction 3, was determined to have the following properties:

Yellow powder; mp 113~118° C.

EIMS m/z (relative intensity): 628 [M]$^+$ (71), 600 (100), 575 (14), 545 (52), 517 (68), 501 (12), 473 (96), 459 (12), 431 (26), 417 (18), 389 (29), 355 (64), 349 (26), 307 (12), 295 (22), 253 (24), 245 (29), 214.9 (26), 189 (17), 105 (15), 91 (18), 69 (35).

$^1$H-NMR (600 MHz, CDCl$_3$): δ 12.57 (1H, s, OH-6), 7.50 (1H, d, J=6.9 Hz, H-10), 5.79 (1H, dd, J=16.0, 7.2 Hz, H-27), 5.30 (1H, d, J=16.0 Hz, H-26), 5.14 (1H, br t, J=6.9 Hz, H-32), 4.57 (1H, s, H$_1$-40), 4.23 (1H, s, H$_2$-40), 3.50 (1H, br d, J=2.8 Hz, H-4), 3.43 (1H, dd, J=6.8, 4.4 Hz, H-11), 3.23 (2H, m, H-31), 2.90 (1H, dq, J=7.2, 7.1 Hz, H-28), 2.56 (1H, d, J=9.3 Hz, H-22), 2.29 (1H, dd, J=13.4, 4.6 Hz, H$_1$-21), 2.16 (1H, br d, J=12.5 Hz, H-37), 1.94 (1H, br d, J=12.9 Hz, H$_1$-20), 1.89 (1H, m, H$_1$-3), 1.86 (3H, s, H-39), 1.75 (1H, m, H$_2$-3), 1.73 (6H, s, H-25, H-34), 1.65 (3H, s, H-35), 1.56 (1H, dt, J=13.4, 5.0 Hz, H$_2$-20), 1.42 (1H, m, H$_2$-21), 1.38 (3H, s, H-19), 1.36 (2H, m, H-36), 1.27 (3H, s, H-24), 0.90 (3H, d, J=7.1 Hz, H-29).

$^{13}$C-NMR (150 MHz, CDCl$_3$): δ 203.38 (C-12), 179.21 (C-8), 177.35 (C-30), 164.29 (C-18), 160.61 (C-6), 155.79 (C-16), 147.66 (C-38), 134.54 (C-9, C-10), 134.33 (C-27), 131.17 (C-33), 123.80 (C-26), 122.45 (C-32), 108.83 (C-40), 106.65 (C-17), 104.18 (C-5), 100.11 (C-7), 91.46 (C-14), 84.76 (C-13), 84.13 (C-23), 77.07 (C-2), 48.27 (C-22), 48.13 (C-37), 47.06 (C-11), 41.74 (C-28), 39.31 (C-20), 36.92 (C-3), 30.03 (C-25), 28.94 (C-4), 28.73 (C-24), 28.50 (C-19), 25.74 (C-35), 25.51 (C-21), 22.98 (C-39), 22.74 (C-36), 21.94 (C-31), 18.18 (C-34), 15.80 (C-29).

The EIMS data of Product Gh-2508 show a molecular ion peak [M]$^+$ at m/z 628, which reveals that the fragmentation pattern of Product Gh-2508 is identical to that of Product Gh-2603-2 gambogellic acid). Besides, the $^1$H-NMR and $^{13}$C-NMR data of Product Gh-2508 are generally similar to those of Product Gh-2603-2.

The $^1$H-NMR and $^{13}$C-NMR data of Product Gh-2508 show that the side chain connected to C-13 and containing a carboxyl group is different from that of Product Gh-2603-2; the disubstituted double bond $\Delta^{26,27}$ (δ 5.79 (1H, dd, J=16.0, 7.2 Hz, H-27) and δ 134.33 (C-27), and δ 5.30 (1H, d, J=16.0 Hz, H-26) and δ 123.80 (C-26)) exists instead of the trisubstituted double bond $\Delta^{27,28}$ and the methylene group (C-26) in Product Gh-2603-2. Besides, since two coupled olefinic protons (H-26 and H-27) have a coupling constant (J) of 16.0 Hz, the double bond $\Delta^{26,27}$ is a trans double bond (namely, in an E-configuration). It can be known from a doublet signal of δ 0.90 (3H, d, J=7.1 Hz, H-29) that C-29 represents a secondary methyl group and H-29 is coupled to a methine proton (δ 2.90 (1H, dq, J=7.2, 7.1 Hz, H-28)). Besides, a methine group (δ 2.90 (H-28) and δ 41.74 (C-28)) is adjacent to a carboxyl carbon (δ 177.35 (C-30)), indicating that the carboxyl carbon is not an α,β-unsaturated carbonyl carbon.

The HMBC data of Product Gh-2508 show that: δ 5.79 (H-27) is correlated with δ 177.35 (C-30), δ 15.80 (C-29), δ 41.74 (C-28) and δ 84.76 (C-13); δ 5.30 (H-26) is correlated with δ 177.35 (C-30), δ 41.74 (C-28), δ 134.33 (C-27) and δ 84.76 (C-13); δ 2.90 (H-28) is correlated with δ 177.35 (C-30), δ 15.80 (C-29), δ 134.33 (C-27) and δ 123.80 (C-26); and δ 0.90 (H-29) is correlated with δ 177.35 (C-30) and δ 134.33 (C-27), evidencing that the side chain connected to C-13 is (E)-2-methyl-3-butenoic acid.

The NOESY data of Product Gh-2508 show that δ 7.50 (H-10) is correlated with δ 3.43 (H-11); δ 3.43 (H-11) is correlated with δ 2.29 (H$_1$-21); and δ 2.56 (H-22) is correlated with δ 1.42 (H$_2$-21) and δ 1.27 (H-24), evidencing that the stereostructure of Product Gh-2508 in this part is identical to that of gambogic acid or gambogellic acid, i.e., in a 11S,13R,14S,22S configuration. Besides, δ 0.90 (H-29) is correlated with not only δ 5.79 (H-27) and δ 5.30 (H-26) but also the adjacent δ 2.90 (H-28).

As further confirmed by the $^1$H-$^1$H COSY, HMQC and HMBC analyses, the monoterpene moiety of Product Gh-2508 is identical to that of Product Gh-2603-2. The signal of the methine proton (δ 2.16 (1H, br d, J=12.5 Hz, H-37)) attached to the isopropenyl group reveals that the methine proton attached to the isopropenyl group and a vicinal proton have a relatively high vicinal coupling constant (J=12.5 Hz) and, hence, they are in an axial-axial coupling relationship. As such, H-37 is in an axial orientation, and C-37 is in an S-configuration.

The NOESY data of Product Gh-2508 show that: δ 3.50 (H-4) is correlated with not only δ 2.16 (H-37) but also δ 1.89 (H$_1$-3) and δ 1.75 (H$_2$-3); δ 1.89 (H$_1$-3) is correlated with δ 1.38 (H-19); and an axial hydrogen δ 2.16 (H-37) is correlated with δ 1.89 (H$_1$-3) and δ 1.56 (H$_2$-20), evidencing that the monoterpene ring has a chair conformation with 1,3-diaxial interaction, and both the methyl proton (H-19) connected to C-2 and the isopropenyl group connected to C-37 are in an equatorial orientation. Inasmuch as no nuclear Overhauser effect (NOE) is present amongst the methyl proton (δ 0.90 (H-29)) on the side chain attached to C-13 and the exo-methylene protons (δ 4.57 (H$_1$-40) and δ 4.23 (H$_2$-40)) of the isopropenyl group in the monoterpene moiety, C-2 is presumed to be in an R configuration. As such, the monoterpene moiety is determined to be in a 2R,4R,37S configuration.

Based on the above information, Product Gh-2508 is identified to be a new compound having the following chemical structure:

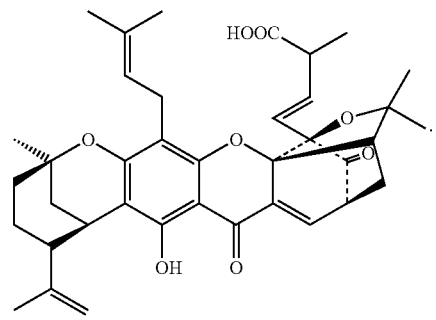

Product Gh-2508 is identified by the name "β-gambogellic acid" {IUPAC nomenclature: [3-butenoic acid, 2-methyl-4-[(1R,3aS,5S,9R,10S,13R,16aS)-3a,4,5,7,10,11,12,13-octahydro-8-hydroxy-3,3,13-trimethyl-15-(3-methyl-2-butenyl)-10-(1-methylethenyl)-7,18-dioxo-1,5:9,13-dimethano-1H,3H,9H-furo[3.4-g]oxocino[3.2-b]xanthen-1-yl]-,(3E)-]}.

16. Product Gh-2507:

Product Gh-2507, which was purified from eluate 23 of fraction 2, was determined to have the following properties:

Yellow needles; mp 148~152° C.

EIMS m/z (relative intensity): 628 [M]$^+$ (48), 600 (100), 585 (9), 545 (41), 517 (69), 510 (12), 473 (93), 431 (24), 417 (18), 389 (28), 355 (68), 347 (25), 307 (11), 299 (24), 295 (20), 253 (22), 245 (28), 214.9 (22), 199 (18), 189 (15), 105 (12), 91 (17), 69 (25).

$^1$H-NMR (600 MHz, CDCl$_3$): δ 12.61 (1H, s, OH-6), 7.48 (1H, d, J=6.9 Hz, H-10), 6.06 (1H, dd, J=15.7, 7.2 Hz, H-27), 5.15 (1H, d, J=15.7 Hz, H-26), 5.11 (1H, br t, J=6.9 Hz, H-32), 4.56 (1H, s, H$_1$-40), 4.20 (1H, s, H$_2$-40), 3.54 (1H, br d, J=2.7 Hz, H-4), 3.44 (1H, dd, J=6.8, 4.5 Hz, H-11), 3.25 (1H, dd, J=14.4, 8.1 Hz, H$_1$-31), 3.17 (1H, dd, J=14.4, 5.6 Hz, H$_2$-31), 2.90 (1H, dq, J=7.2, 7.1 Hz, H-28), 2.56 (1H, d, J=9.3 Hz, H-22), 2.30 (1H, dd, J=13.5, 4.7 Hz, H$_1$-21), 2.16 (1H, br d, J=12.4 Hz, H-37), 1.97 (1H, br d, J=12.8 Hz, H$_1$-20), 1.88 (1H, m, H$_1$-3), 1.87 (3H, s, H-39), 1.74 (1H, m, H$_2$-3), 1.72 (3H, s, H-25), 1.71 (3H, s, H-34), 1.64 (3H, s, H-35), 1.55 (1H, dt, J=13.5, 4.9 Hz, H$_2$-20), 1.44 (1H, m, H$_2$-21), 1.43 (1H, m, H$_1$-36), 1.36 (3H, s, H-19), 1.32 (1H, m, H$_2$-36), 1.27 (3H, s, H-24), 0.92 (3H, d, J=7.0 Hz, H-29).

$^{13}$C-NMR (150 MHz, CDCl$_3$): δ 203.53 (C-12), 179.16 (C-8), 177.27 (C-30), 164.37 (C-18), 160.73 (C-6), 156.10 (C-16), 148.04 (C-38), 134.80 (C-10), 134.65 (C-27), 134.52 (C-9), 131.20 (C-33), 122.91 (C-26), 122.39 (C-32), 108.71 (C-40), 106.53 (C-17), 104.14 (C-5), 99.93 (C-7), 90.92 (C-14), 84.66 (C-13), 84.10 (C-23), 77.16 (C-2), 48.49 (C-22), 48.15 (C-37), 47.03 (C-11), 42.00 (C-28), 39.21 (C-20), 37.04 (C-3), 29.96 (C-25), 28.93 (C-4), 28.76 (C-24), 28.53 (C-19), 25.77 (C-35), 25.35 (C-21), 22.94 (C-39), 22.59 (C-36), 22.01 (C-31), 18.15 (C-34), 15.92 (C-29).

The EIMS data of Product Gh-2507 show a molecular ion peak [M]$^+$ at m/z 628, which is identical to those of Products Gh-2603-1 (i.e., epigambogellic acid) and Gh-2603-2 (i.e., gambogellic acid). Besides, the $^1$H-NMR and $^{13}$C-NMR data of Product Gh-2507 are generally similar to those of Product Gh-2603-1.

The $^1$H-NMR and $^{13}$C-NMR data of Product Gh-2507 show that a side chain connected to C-13 and having a carboxyl group differs from that of Product Gh-2603-1; a disubstituted double bond Δ$^{26,27}$ (δ 5.15 (1H, d, J=15.7 Hz, H-26) and δ 122.91 (C-26), and δ 6.06 (1H, dd, J=15.7, 7.2 Hz, H-27) and δ 134.65 (C-27)] exists instead of the trisubstituted double bond Δ$^{27,28}$ and the methylene group (C-26) in Product Gh-2603-1; and two coupled olefinic protons (H-26 and H-27) have a coupling constant (J) of 15.7 Hz. As such, the disubstituted double bond Δ$^{26,27}$ is a trans double bond (namely, in an E-configuration). It can be known from a doublet signal of δ 0.92 (3H, d, J=7.0 Hz, H-29) that C-29 represents a secondary methyl group, and the proton (H-29) of the secondary methyl group is coupled to a methine proton (δ 2.90 (1H, dq, J=7.2, 7.1 Hz, H-28)). In addition, since the methine group (δ 2.90 (H-28) and δ 42.00 (C-28)) is adjacent to a carboxyl carbon (δ 177.27 (C-30)), the carboxyl carbon is not an α,β-unsaturated carbonyl carbon.

The HMBC data of Product Gh-2507 show that: δ 6.06 (H-27) is correlated with δ 177.27 (C-30), δ 15.92 (C-29), δ 42.00 (C-28) and δ 84.66 (C-13); δ 5.15 (H-26) is correlated with δ 42.00 (C-28), δ 134.65 (C-27), δ 84.66 (C-13) and δ 203.53 (C-12); δ 2.90 (H-28) is correlated with δ 177.27 (C-30), δ 15.92 (C-29), δ 134.65 (C-27) and δ 122.91 (C-26); and δ 0.92 (H-29) is correlated with δ 177.27 (C-30), δ 42.00 (C-28) and δ 134.65 (C-27), evidencing that the side chain attached to C-13 is (E)-2-methyl-3-butenoic acid.

The NOESY data of Product Gh-2507 show that: δ 7.48 (H-10) is correlated with δ 3.44 (H-11); δ 3.44 (H-11) is correlated with δ 2.30 (H$_1$-21) and δ 1.44 (H$_2$-21); δ 1.44 (H$_2$-21) is correlated with δ 2.56 (H-22); and δ 2.56 (H-22) is correlated with δ 1.72 (H-25), evidencing that the stereostructure of Product Gh-2507 in this part is identical to that of gambogic acid, gambogellic acid and epigambogellic acid, i.e., in a 11S,13R,14S,22S configuration. Besides, δ 0.92 (H-29) is correlated with δ 2.90 (H-28), δ 6.06 (H-27), δ 5.15 (H-26), and δ 4.20 (H$_2$-40). The methyl proton (H-29) is correlated with the exo-methylene protons (δ 4.56 (H$_1$-40) and δ 4.20 (H$_2$-40)] of the isopropenyl group in the monoterpene moiety. As such, C-2 is presumed to be in a S-configuration. If C-2 is in a R configuration, no cross peaks would appear.

As further confirmed by the $^1$H-$^1$H COSY, HMQC and HMBC analyses, the monoterpene moiety of Product Gh-2507 is identical to that of Product Gh-2603-1. The signal of the methine proton (δ 2.16 (1H, br d, J=12.4 Hz, H-37)) attached to the isopropenyl group reveals that the methine proton attached to the isopropenyl group and a vicinal proton have a relatively high vicinal coupling constant (J=12.4 Hz) and, hence, they are in an axial-axial coupling relationship. As such, H-37 is in an axial orientation, and C-37 is in an R configuration.

The NOESY data of Product Gh-2507 also reveal that: δ 3.54 (H-4) is correlated with not only δ 2.16 (H-37) but also δ 1.88 (H$_1$-3) and δ 1.74 (H$_2$-3); the methylene protons (H$_1$-3 and H$_2$-3) both are correlated with δ 1.36 (H-19); and the axial hydrogen δ 2.16 (H-37) is correlated with not only δ 1.87 (H-39) but also δ 1.88 (H$_1$-3), δ 1.55 (H$_2$-20) and δ 1.43 (H$_1$-36), evidencing that the monoterpene ring has a chair conformation with 1,3-diaxial interaction, in which both the methyl group (C-19) connected to C-2 and the isopropenyl group connected to C-37 are in an equatorial orientation. As such, the stereostructure of the p-menthene monoterpene is in a 2S,4S,37R configuration.

Based on the above information, Product Gh-2507 is identified to be a new compound having the following chemical structure:

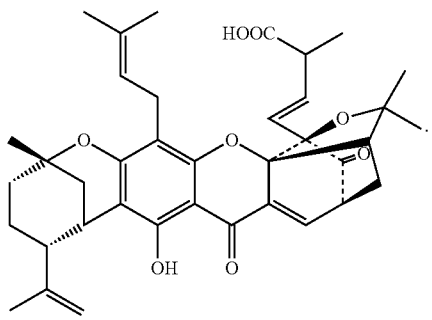

Product Gh-2507 is identified by the name "β-epigambogellic acid" {IUPAC nomenclature: [3-butenoic acid, 2-methyl-4-[(1R,3aS,5S,9S,10R,13S,16aS)-3a,4,5,7,10,11,12,13-octahydro-8-hydroxy-3,3,13-trimethyl-15-(3-methyl-2-butenyl)-10-(1-methylethenyl)-7,18-dioxo-1,5:9,13-dimethano-1H,3H,9H-furo[3.4-g]oxocino[3.2-b]xanthen-1-yl],(3E)-]}.

17. Product Gh-2501:

Product Gh-2501, which was purified from eluate 21 of fraction 2, was determined to have the following properties:

Yellow powder; mp 100~103° C.

EIMS m/z (relative intensity): 544 [M]$^+$ (100), 529 (67), 516 (16), 501 (56), 473 (13), 435 (11), 405 (59), 389 (25), 363 (43), 349 (37), 337 (12), 307 (34), 287 (58), 259 (29), 229 (69), 215 (59), 189 (35), 147 (23), 135 (30), 105 (42), 91 (27), 83 (29), 69 (36), 55 (34).

$^1$H-NMR (600 MHz, CDCl$_3$): δ 12.70 (1H, s), 9.21 (1H, s), 7.54 (1H, d, J=7.0 Hz), 6.59 (1H, d, J=10.0 Hz), 6.37 (1H, t, J=8.5 Hz), 5.50 (1H, d, J=10.0 Hz), 5.07 (1H, t, J=8.4 Hz), 3.51 (1H, dd, J=6.9, 4.5 Hz), 3.25 (1H, dd, J=14.4, 8.1 Hz), 3.17 (1H, br dd, J=13.9, 5.9 Hz), 2.71 (1H, ddd, J=16.0, 7.5, 0.8 Hz), 2.62 (1H, ddd, J=16.0, 7.0, 0.9 Hz), 2.56 (1H, d, J=9.4 Hz), 2.34 (1H, dd, J=13.6, 4.7 Hz), 1.73 (3H, s), 1.71 (3H, s), 1.62 (3H, s), 1.43 (3H, s), 1.41 (3H, s), 1.39 (1H, m), 1.29 (3H, s), 1.28 (3H, d, J=1.2 Hz).

$^{13}$C-NMR (150 MHz, CDCl$_3$): δ 203.02, 194.46, 178.84, 161.34, 157.68, 157.15, 146.51, 140.11, 135.62, 133.34, 131.98, 126.39, 121.82, 115.28, 108.07, 103.27, 100.36, 90.79, 83.98, 83.39, 78.87, 48.99, 46.85, 29.96, 28.96, 28.93, 28.39 (2C), 25.75, 25.26, 21.67, 18.16, 8.58.

According to the obtained spectral data, Product Gh-2501 was identified to be a known compound having the following chemical structure, i.e., isomorellin:

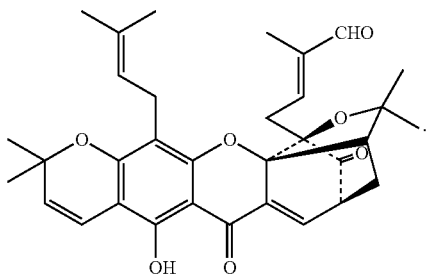

18. Product Gh-2505:

Product Gh-2505, which was purified from eluate 24 of fraction 2, was determined to have the following properties:

Yellow powder; mp 67~70° C.

EIMS m/z (relative intensity): 630 [M]$^+$ (100), 602 (19), 545 (14), 507 (36), 479 (22), 475 (18), 433 (8), 351 (27), 309 (17), 295 (38), 253 (45), 245 (16), 231 (16), 213 (13), 177 (15), 147 (8), 69 (29).

$^1$H-NMR (600 MHz, CDCl$_3$): δ 12.81 (1H, s), 7.52 (1H, d, J=6.9 Hz), 6.48 (1H, s), 5.83 (1H, t, J=7.2 Hz), 5.17 (1H, t, J=6.9 Hz), 5.06 (1H, br t, J=6.6 Hz), 5.02 (1H br t, J=6.7 Hz), 3.48 (1H, dd, J=6.6, 4.8 Hz), 3.30 (1H, m), 3.28 (2H, m), 3.24 (1H, dd, J=16.1, 7.1 Hz), 3.10 (1H, dd, J=15.7, 8.7 Hz), 2.86 (1H, ddd, J=15.9, 6.7, 1.1 Hz), 2.49 (1H, d, J=9.4 Hz), 2.30 (1H, dd, J=13.5, 4.7 Hz), 2.06 (2H, m), 2.00 (2H, m), 1.74 (3H, s), 1.71 (3H, s), 1.70 (3H, s), 1.66 (3H, s), 1.65 (3H, s), 1.64 (3H, s), 1.56 (3H, s), 1.36 (1H, dd, J=13.5, 9.5 Hz), 1.27 (3H, s).

$^{13}$C-NMR (150 MHz, CDCl$_3$): δ 203.38, 179.12, 170.39, 163.62, 160.34, 155.85, 139.06, 136.95, 135.15, 133.91, 133.52, 131.88, 128.50, 123.83, 121.91, 121.35, 107.50, 106.43, 100.64, 90.41, 83.94, 83.87, 48.90, 46.88, 39.68, 29.79, 29.46, 28.92, 26.33, 25.71, 25.67, 25.21, 22.03, 21.09, 20.74, 17.98, 17.68, 16.16.

According to the obtained spectral data, Product Gh-2505 was identified to be a known compound having the following chemical structure, i.e., gambogenic acid:

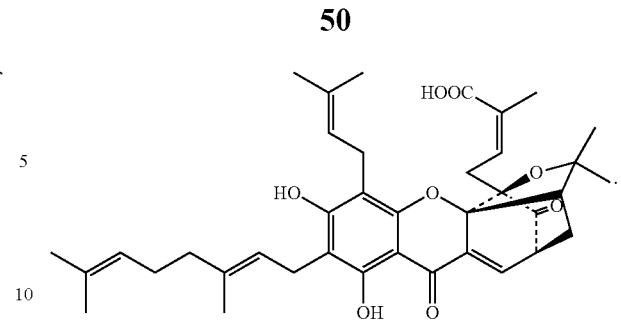

19. Product Gh-2642:

Product Gh-2642, which was purified from eluate 22 of fraction 2, was determined to have the following properties:

Yellow powder; mp 157~159° C.

EIMS m/z (relative intensity): 630 [M]$^+$ (100), 602 (11), 545 (11), 533 (16), 507 (46), 479 (21), 475 (15), 433 (7), 419 (8), 381 (9), 357 (13), 351 (20), 309 (14), 295 (27), 253 (34), 245 (15), 231 (16), 213 (11), 177 (15), 147 (8), 135 (8), 105 (11), 69 (44).

$^1$H-NMR (600 MHz, CDCl$_3$): δ 12.76 (1H, s), 7.52 (1H, d, J=7.0 Hz), 6.70 (1H, br s), 6.59 (1H, t, J=7.5 Hz), 5.19 (1H, t, J=7.0 Hz), 5.10 (1H, br t, J=6.0 Hz), 5.02 (1H, br t, J=6.1 Hz), 3.47 (1H, t, J=5.6 Hz), 3.34 (2H, m), 3.31 (2H, m), 2.60 (1H, dd, J=15.7, 7.9 Hz), 2.50 (1H, m), 2.49 (1H, d, J=9.5 Hz), 2.30 (1H, dd, J=13.3, 4.4 Hz), 2.06 (2H, m), 2.02 (2H, m), 1.76 (3H, s), 1.70 (3H, s), 1.66 (6H, s), 1.62 (3H, s), 1.54 (3H, s), 1.35 (1H, dd, J=13.3, 9.5 Hz), 1.30 (3H, s), 1.25 (3H, s).

$^{13}$C-NMR (150 MHz, CDCl$_3$): δ 203.15, 179.02, 172.20, 163.51, 160.27, 155.87, 138.98, 136.90, 135.50, 133.72, 133.33, 131.75, 128.64, 123.81, 121.88, 121.15, 107.51, 106.63, 100.55, 90.37, 83.65, 83.49, 48.89, 46.82, 39.61, 29.80, 28.85 (2C), 26.27, 25.65, 25.60, 25.19, 21.98, 21.10, 17.93, 17.59, 16.16, 11.34.

According to the obtained spectral data, Product Gh-2642 was identified to be a known compound having the following chemical structure, i.e., isogambogenic acid:

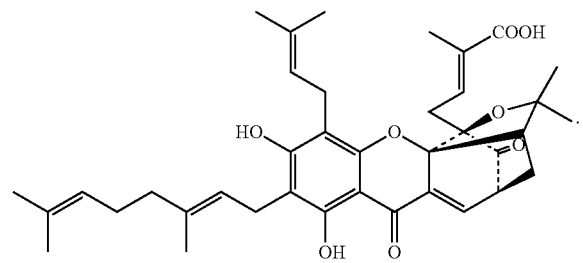

20. Product Gh-1601-A:

Product Gh-1601-A, which was purified from eluate 20 of fraction 2, was determined to have the following properties:

Yellow powder; mp 143~145° C.

EIMS m/z (relative intensity): 644 [M]$^+$ (72), 598 (18), 561 (100), 515 (23), 474 (35), 431 (9), 391 (10), 355 (14), 349 (7), 347 (6), 253 (6), 248 (11), 215 (11), 189 (6), 125 (4), 69 (18).

$^1$H-NMR (600 MHz, CDCl$_3$): δ 12.76 (1H, s), 7.54 (1H, d, J=6.9 Hz), 6.61 (1H, d, J=10.2 Hz), 6.31 (1H, t, J=7.2 Hz), 5.41 (1H, d, J=10.1 Hz), 5.02 (2H, br s), 4.09 (1H, d, J=13.3 Hz), 4.01 (1H, d, J=13.3 Hz), 3.49 (1H, br t, J=5.6 Hz), 3.27 (1H, dd, J=14.2, 8.0 Hz), 3.13 (1H, br dd, J=14.3, 5.2 Hz), 2.96 (2H, d, J=7.5 Hz), 2.51 (1H, d, J=9.6 Hz), 2.31 (1H, dd,

J=13.4, 4.7 Hz), 2.00 (2H, m), 1.72 (1H, m), 1.70 (3H, s), 1.67 (3H, s), 1.62 (3H, s), 1.60 (3H, s), 1.58 (1H, m), 1.52 (3H, s), 1.38 (1H, m), 1.37 (3H, s), 1.26 (3H, s).

$^{13}$C-NMR (150 MHz, CDCl$_3$): δ 203.04, 179.01, 169.43, 161.66, 157.50, 157.27, 139.33, 135.66, 133.20, 131.90, 131.87, 131.24, 124.80, 123.69, 121.96, 115.76, 107.75, 102.82, 100.47, 90.76, 84.25, 83.67, 81.47, 64.80, 48.92, 46.82, 41.93, 29.82, 29.14, 28.82, 27.76, 25.68, 25.65, 25.12, 22.70, 21.60, 18.13, 17.61.

According to the obtained spectral data, Product Gh-1601-A was identified to be a known compound having the following chemical structure, i.e., 30-hydroxygambogic acid:

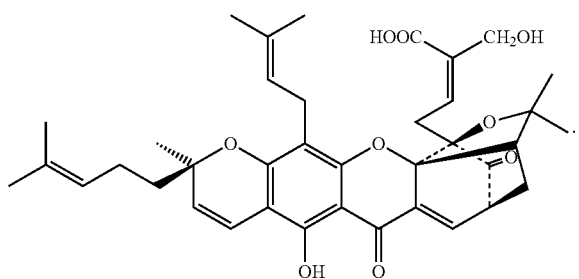

21. Product Gh-1602:

Product Gh-1602, which was purified from eluate 18 of fraction 2, was determined to have the following properties:
Yellow powder; mp 98~100° C.

EIMS m/z (relative intensity): 644 [M]$^+$ (28), 598 (5), 561 (100), 515 (15), 474 (9), 431 (3), 389 (5), 355 (5), 347 (5), 253 (3), 245 (6), 215 (10), 189 (5), 125 (3), 69 (8).

$^1$H-NMR (600 MHz, CDCl$_3$): δ 12.73 (1H, s), 7.54 (1H, d, J=6.9 Hz), 6.60 (1H, d, J=10.1 Hz), 6.40 (1H, t, J=7.4 Hz), 5.39 (1H, d, J=10.2 Hz), 5.07 (1H, t, J=7.0 Hz), 5.01 (1H, br t, J=6.8 Hz), 4.09 (1H, d, J=13.1 Hz), 4.02 (1H, d, J=13.2 Hz), 3.46 (1H, t, J=5.6 Hz), 3.27 (1H, dd, J=14.6, 8.2 Hz), 3.12 (1H, dd, J=14.6, 5.0 Hz), 2.96 (2H, d, J=7.5 Hz), 2.50 (1H, d, J=9.3 Hz), 2.29 (1H, dd, J=13.5, 4.7 Hz), 2.04 (2H, m), 1.73 (1H, m), 1.71 (3H, s), 1.67 (3H, s), 1.64 (3H, s), 1.62 (1H, m), 1.61 (3H, s), 1.56 (3H, s), 1.36 (1H, m), 1.32 (3H, s), 1.26 (3H, s).

$^{13}$C-NMR (150 MHz, CDCl$_3$): δ 203.08, 179.02, 169.57, 161.46, 157.50, 157.24, 140.20, 135.91, 133.02, 132.20, 131.62, 131.15, 124.94, 123.74, 122.04, 115.81, 107.89, 102.95, 100.50, 90.89, 84.02, 83.56, 81.21, 64.64, 48.91, 46.82, 41.67, 29.90, 29.14, 28.77, 26.91, 25.69, 25.61, 25.19, 22.73, 21.58, 18.15, 17.60.

According to the obtained spectral data, Product Gh-1602 was identified to be a known compound having the following chemical structure, i.e., 30-hydroxyepigambogic acid:

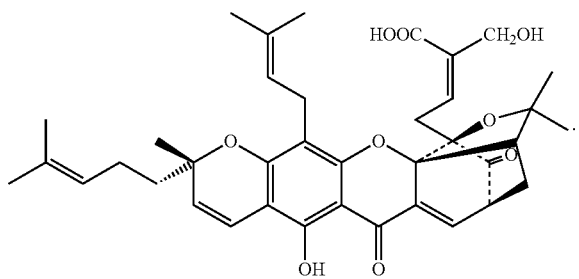

22. Product Gh-2641-1:

Product Gh-2641-1, which was purified from eluate 20 of fraction 2, was determined to have the following properties:
Yellow powder; mp 94~98° C.

EIMS m/z (relative intensity): 646 [M]$^+$ (100), 545 (18), 523 (80), 495 (28), 477 (17), 449 (16), 367 (44), 349 (20), 325 (37), 295 (41), 252.9 (49), 245 (27), 213 (32), 147 (16).

$^1$H-NMR (600 MHz, CDCl$_3$): δ 12.84 (1H, s, OH-6), 7.46 (1H, d, J=7.0 Hz, H-10), 5.30 (1H, ddd, J=12.1, 4.0, 1.4 Hz, H-27), 5.19 (1H, dt, J=7.1, 1.2 Hz, H-32), 5.04 (1H, tt, J=6.9, 1.3 Hz, H-37), 4.68 (1H, dd, J=9.8, 6.5 Hz, H-4), 3.76 (1H, dd, J=14.5, 12.1 Hz, H$_1$-26), 3.48 (1H, d, J=7.0, 4.2 Hz, H-11), 3.16 (2H, m, H-31), 3.13 (1H, dd, J=15.3, 6.5 Hz, H$_1$-3), 3.03 (1H, dd, J=15.3, 9.8 Hz, H$_2$-3), 2.76 (1H, ddd, J=14.5, 4.0, 2.2 Hz, H$_2$-26), 2.39 (1H, d, J=9.6 Hz, H-22), 2.32 (1H, dd, J=13.5, 4.5 Hz, H$_1$-21), 2.02 (2H, m, H-36), 1.91 (2H, m, H-20), 1.70 (3H, s, H-35), 1.64 (3H, s, H-25), 1.61 (3H, s, H-39), 1.53 (3H, s, H-40), 1.51 (3H, s, H-29), 1.43 (3H, s, H-19), 1.33 (1H, m, H$_2$-21), 1.28 (3H, s, H-24), 1.25 (3H, s, H-34).

$^{13}$C-NMR (150 MHz, CDCl$_3$): δ 202.10 (C-12), 178.09 (C-8), 168.66 (C-30), 167.88 (C-18), 163.12 (C-16), 152.96 (C-6), 135.41 (C-33), 135.12 (C-27), 134.13 (C-10), 133.72 (C-9), 131.18 (C-38), 129.76 (C-28), 124.36 (C-37), 121.53 (C-32), 104.85 (C-5), 103.47 (C-17), 100.53 (C-7), 90.43 (C-4), 90.21 (C-14), 84.37 (C-13), 83.66 (C-23), 73.26 (C-2), 48.88 (C-22), 46.61 (C-11), 39.67 (C-20), 30.13 (C-26), 29.92 (C-25), 29.15 (C-24), 26.65 (C-36, C-3), 26.60 (C-19), 25.60 (C-39), 25.19 (C-21), 24.65 (C-35), 21.25 (C-31), 20.47 (C-29), 17.58 (C-40), 16.04 (C-34).

The EIMS data of Product Gh-2641-1 show a molecular ion peak [M]$^+$ at m/z 646, which corresponds to xanthones having a molecular formula of $C_{38}H_{46}O_9$.

The $^1$H-NMR data of product Gh-2641-1 show that Product Gh-2641-1 has a chelated hydroxy group (δ 12.84), four olefinic protons (δ 7.46, δ 5.30, δ 5.19, and δ 5.04), and a secondary hydroxy group (δ 4.68). As compared to gambogic acid, the $^1$H-NMR spectra of product Gh-2641-1 has one less signal of a coupled cis-disubstituted double bond and one more proton signal of AX$_2$ spin system (δ 4.68 (1H, dd, J=9.8, 6.5 Hz, H-4), δ 3.13 (1H, dd, J=15.3, 6.5 Hz, H$_1$-3), and δ 3.03 (1H, dd, J=15.3, 9.8 Hz, H$_2$-3)), which indicates that Product Gh-2641-1 may be a known compound neogambogic acid.

The HMBC data of Product Gh-2641-1 show that: in addition to being correlated with two quaternary carbons (δ 103.47 (C-17) and δ 167.88 (C-18)), the hydroxymethine proton (δ 4.68 (1H, dd, J=9.8, 6.5 Hz, H-4)) is correlated with an oxygen-bearing quaternary carbon (δ 73.26 (C-2)) of a pyran ring and a tertiary methyl group (δ 26.60 (C-19)), evidencing that the hydroxyl group is attached to C-4. It can be known from the coupling constant of H-4 (J=9.8, 6.5 Hz) that the quasi-axial proton on C-4 is coupled to the quasi-axial H$_2$-3 (J=9.8 Hz) and the quasi-equatorial H$_1$-3 (J=6.5 Hz), respectively. As such, the hydroxy group is in β-orientation.

The NOESY data of Product Gh-2641-1 show that: δ 7.46 (H-10) is correlated with δ 3.48 (H-11); δ 3.48 (H-11) is correlated with δ 2.32 (H$_1$-21); δ 2.32 (H$_1$-21) is correlated with δ 2.39 (H-22); δ 2.39 (H-22) is correlated with δ 1.28 (H-24); and δ 5.30 (H-27) is correlated with δ 1.51 (H-29), evidencing that the stereostructure of product Gh-2641-1 in this part is identical to that of gambogic acid, i.e., in a 11S,13R,14S,22S configuration, which includes H-27 and carboxyl group (C-30) in a trans relationship, and a double bond $\Delta^{27,28}$ in a Z configuration. In addition, δ 4.68 (H-4) is correlated with δ 1.43 (H-19), which indicates that the methyl proton connected to C-2 is in an axial orientation (or α-orientation). As such, C-2 of Product Gh-2641-1 has a configuration identical to that of gambogic acid, i.e., in an R configuration.

According to the obtained spectral data, Product Gh-2641-1 is identified to be a known compound having the following chemical structure, i.e., neogambogic acid:

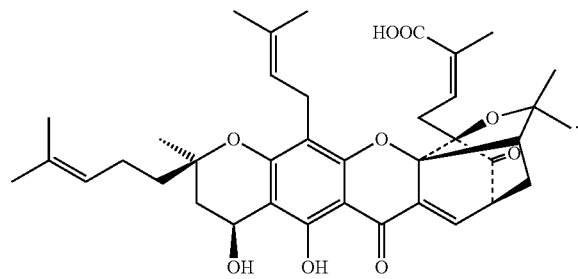

23. Product Gh-1631:

Product Gh-1631, which was purified from eluate 19 of fraction 2, was determined to have the following properties:

Yellow needles; mp 95~97° C.

EIMS m/z (relative intensity): 646 [M]$^+$ (54), 618 (75), 573 (12), 545 (8), 520 (13), 492 (75), 491 (100), 477 (18), 449 (38), 373 (19), 349 (11), 321 (15), 295 (27), 267 (10), 252.9 (37), 245 (18), 213 (11), 188.9 (15), 176.9 (11), 109 (24), 99 (20), 69 (83); HREIMS [M]$^+$ m/z: 646.3146; calculated for $C_{38}H_{46}O_9$, 646.3142.

$^1$H-NMR (600 MHz, $CDCl_3$): δ 12.45 (1H, s, OH-6), 7.42 (1H, d, J=6.9 Hz, H-10), 5.32 (1H, br d, J=9.9 Hz, H-27), 5.18 (1H, t, J=6.8 Hz, H-32), 5.08 (1H, t, J=7.1 Hz, H-37), 4.75 (1H, t, J=8.1 Hz, H-3), 3.53 (1H, dd, J=15.7, 11.0 Hz, $H_1$-26), 3.48 (1H, dd, J=6.6, 4.8 Hz, H-11), 3.29 (1H, dd, J=15.1, 7.3 Hz, $H_1$-31), 3.24 (1H, dd, J=15.2, 6.3 Hz, $H_2$-31), 3.07 (2H, d, J=8.1 Hz, H-4), 2.69 (1H, ddd, J=15.8, 4.0, 2.3 Hz, $H_2$-26), 2.53 (1H, d, J=9.4 Hz, H-22), 2.30 (1H, dd, J=13.5, 4.8 Hz, $H_1$-21), 2.09 (1H, m, $H_1$-36), 2.02 (1H, m, $H_2$-36), 1.72 (3H, s, H-34), 1.67 (3H, s, H-35), 1.66 (3H, s, H-39), 1.65 (3H, s, H-25), 1.601 (3H, s, H-40), 1.597 (3H, sh, H-29), 1.57 (1H, m, $H_1$-20), 1.47 (1H, m, $H_2$-20), 1.42 (1H, m, $H_2$-21), 1.42 (3H, s, H-19), 1.23 (3H, s, H-24).

$^{13}$C-NMR (150 MHz, $CDCl_3$): δ 204.15 (C-12), 179.64 (C-8), 168.08 (C-30), 168.02 (C-18), 158.45 (C-16), 157.32 (C-6), 136.74 (C-27, C-33), 134.37 (C-10), 132.40 (C-38), 132.12 (C-9), 128.40 (C-28), 123.56 (C-37), 121.83 (C-32), 105.90 (C-5), 103.96 (C-17), 101.72 (C-7), 90.28 (C-14), 90.00 (C-3), 84.40 (C-13), 83.45 (C-23), 75.77 (C-2), 75.70 (C-2), 48.78 (C-22), 47.71 (C-11), 36.93 (C-20), 29.87 (C-25), 29.32 (C-26), 28.87 (C-24), 25.93 (C-4), 25.71 (C-35), 25.64 (C-39), 25.14 (C-21), 23.54 (C-19), 22.51 (C-31), 22.06 (C-36), 20.91 (C-29), 17.94 (C-34), 17.66 (C-40).

The EIMS data of Product Gh-1631 show a molecular ion peak [M]$^+$ at m/z 646 (54) and a base peak at m/z 491 (100), and the HREIMS data of Product Gh-1631 show [M]$^+$ at m/z 646.3146, indicating that Product Gh-1631 has a molecular formula identical to that of Product Gh-2641-1 (i.e., neogambogic acid), namely, $C_{38}H_{46}O_9$.

The $^1$H-NMR data of Product Gh-1631 show that: Product Gh-1631 has a chelated hydroxy group (δ 12.45), four olefinic protons (δ 7.42, δ 5.32, δ 5.18, and δ 5.08), and a secondary hydroxy group having a hydroxymethine proton (δ 4.75 (1H, t, J=8.1 Hz)) coupled with a methylene proton (δ 3.07 (2H, d, J=8.1 Hz)). The $^1$H-NMR data of Product Gh-1631 are generally similar to those of Product Gh-2641-1.

The HMQC data of Product Gh-1631 reveal that: δ 90.00 (—OCH—) and δ 25.93 (—$CH_2$—) are signals that correspond to a hydroxymethine carbon and a methylene carbon adjacent to the hydroxymethine carbon, respectively. As such, it is presumed that Product Gh-1631 and Product Gh-2641-1 are isomers that differ from each other at the site of the hydroxy group, and Product Gh-1631 may have the hydroxy group connected to C-3.

The HMBC data of Product Gh-1631 show that: δ 4.75 is correlated with δ 168.02 (C-18), δ 105.90 (C-5), δ 75.77 (C-2), δ 75.70 (C-2), δ 25.93 (C-4) and δ 23.54 (C-19); and δ 3.07 is correlated with δ 90.00 (C-3), δ 105.90 (C-5), δ 75.77 (C-2), δ 75.70 (C-2), δ 157.32 (C-6), δ 168.02 (C-18), δ 103.96 (C-17), δ 101.72 (C-7) and δ 158.45 (C-16), evidencing that the hydroxyl group is connected to C-3. In addition, since no conjugated double bond is present therein, the conformation of the pyran ring is in a flexible form, which renders the two protons of the C-4 methylene group to be in equivalence and have identical chemical shift (δ 3.07 (2H, d, J=8.1 Hz, H-4)), in which δ 3.07 is correlated with δ 4.75 (1H, t, J=8.1 Hz, H-3). As such, the hydroxy group on C-3 is in an axial orientation (or β-orientation), and C-3 is in an R configuration.

The NOESY data of Product Gh-1631 reveal that: δ 7.42 (H-10) is correlated with δ 3.48 (H-11); δ 3.48 (H-11) is correlated with δ 2.30 ($H_1$-21); δ 2.53 (H-22) is correlated with δ 1.42 ($H_2$-21); δ 2.30 ($H_1$-21) is correlated with δ 1.23 (H-24); and δ 5.32 (H-27) is correlated with δ 1.597 (H-29), evidencing that the stereostructure of product Gh-1631 in this part is identical to that of gambogic acid, i.e., in a 11S,13R,14S,22S configuration, which includes H-27 and carboxyl group (C-30) in a trans relationship, and a double bond $\Delta^{27,28}$ in a Z configuration. In addition, δ 4.75 (H-3) is correlated with δ 3.07 (H-4), δ 1.42 (H-19), δ 1.47 ($H_2$-20) and δ 2.02 ($H_2$-36), which indicates that the C-3 proton is in an equatorial orientation (α-orientation), and the methyl group attached to C-2 is in an axial orientation (α-orientation). As such, C-2 is in an R configuration.

Based on the above information, Product Gh-1631 is identified to be a new compound having the following chemical structure:

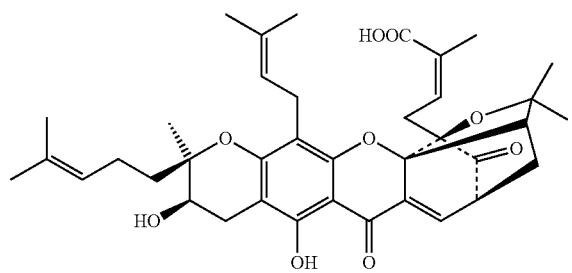

Product Gh-1631 is identified by the name "formoxanthone C" {IUPAC nomenclature [2-butenoic acid, 2-methyl-4-[(1R,3aS,5S,10R,11R,14aS)-3a,4,5,7,10,11-hexahydro-8,10-dihydroxy-3,3,11-trimethyl-13-(3-methyl-2-butenyl)-11-(4-methyl-3-pentenyl)-7,15-dioxo-1,5-methano-1H,3H,9H-furo[3.4-g]pyrano[3.2-b]xanthen-1-yl]-,(2Z)-]}.

24. Product Gh-1050:

Product Gh-1050, which was purified from eluate 17 of fraction 2, was determined to have the following properties:

Yellow powder; mp 55~57° C.

EIMS m/z (relative intensity): 644 [M]+ (82), 616 (98), 601 (9), 598 (8), 571 (16), 533 (17), 517 (12), 490 (100), 489 (96), 475 (19), 447 (30), 433 (13), 405 (18), 371 (33), 363 (17), 309 (10), 295 (21), 253 (25), 230 (19), 213 (15), 189 (9), 173 (10), 147 (11), 105 (17), 99 (25), 69 (42); HREIMS [M]+ m/z: 644.2983; calculated for $C_{38}H_{44}O_9$, 644.2985.

$^1$H-NMR (600 MHz, CDCl$_3$): δ 12.69 (1H, s, OH-6), 7.47 (1H, d, J=6.8 Hz, H-10), 5.57 (1H, t, J=7.5 Hz, H-27), 5.19 (1H, t, J=6.8 Hz, H-32), 4.63 (1H, s, H$_1$-40), 4.29 (1H, s, H$_2$-40), 3.86 (1H, d, J=3.4 Hz, H-3), 3.65 (1H, t, J=2.6 Hz, H-4), 3.49 (1H, t, J=5.7 Hz, H-11), 3.31 (1H, m, H$_1$-31), 3.28 (1H, m, H$_1$-26), 3.23 (1H, dd, J=14.6, 6.2 Hz, H$_2$-31), 2.82 (1H, dd, J=14.9, 5.6 Hz, H$_2$-26), 2.55 (1H, d, J=9.4 Hz, H-22), 2.31 (1H, m, H$_1$-21), 2.29 (1H, m, H-37), 2.03 (1H, br d, J=13.3 Hz, H$_1$-20), 1.92 (3H, s, H-39), 1.76 (3H, s, H-34), 1.70 (3H, s, H-25), 1.69 (3H, s, H-35), 1.62 (3H, s, H-29), 1.60 (1H, m, H$_2$-20), 1.49 (3H, s, H-19), 1.39 (1H, m, H$_2$-21), 1.31 (2H, m, H-36), 1.29 (3H, s, H-24).

$^{13}$C-NMR (150 MHz, CDCl$_3$): δ 204.09 (C-12), 178.99 (C-8), 168.63 (C-30), 163.38 (C-18), 162.82 (C-6), 155.99 (C-16), 146.45 (C-38), 136.18 (C-27), 134.28 (C-10, C-9), 131.50 (C-33), 128.27 (C-28), 122.31 (C-32), 109.58 (C-40), 106.42 (C-17), 100.23 (C-5), 100.12 (C-7), 90.17 (C-14), 84.66 (C-23), 83.64 (C-13), 79.48 (C-2), 71.37 (C-3), 48.90 (C-22), 48.27 (C-37), 47.01 (C-11), 38.29 (C-20), 36.69 (C-4), 29.93 (C-25), 29.47 (C-26), 28.85 (C-24), 25.73 (C-35), 25.14 (C-21), 23.66 (C-19), 22.95 (C-39), 21.98 (C-36), 21.92 (C-31), 20.93 (C-29), 18.15 (C-34).

The EIMS data of Product Gh-1050 show a molecular ion peak [M]+ at m/z 644 and a base peak at m/z 490 (100), and the HREIMS data of Product Gh-1050 show [M]+ at m/z 644.2983, indicating that the fragmentation pattern of Product Gh-1050 is similar to that of Product Gh-2603-2 (namely, gambogellic acid), except for having sixteen more mass units than gambogellic acid. Besides, the $^1$H-NMR and $^{13}$C-NMR data of Product Gh-1050 are generally similar to those of Product Gh-2603-2.

The $^1$H-NMR, $^{13}$C-NMR and $^1$H-$^1$H COSY data of Product Gh-1050 show that: the structure of Product Gh-1050 includes a monoterpene moiety having exo-methylene protons (δ 4.63 (H$_1$-40), δ 4.29 (H$_2$-40), and δ 109.58 (C-40)) in an isopropenyl group, two adjacent methylene groups (δ 2.03 (1H, br d, J=13.3 Hz, H$_1$-20), δ 1.60 (1H, m, H$_2$-20), δ 38.29 (C-20), δ 1.31 (2H, m, H-36), and δ 21.98 (C-36)), a secondary hydroxy group (δ 3.86 (1H, d, J=3.4 Hz, H-3) and δ 71.37 (C-3)), and a methine group (δ 3.65 (1H, t, J=2.6 Hz, H-4) and δ 36.69 (C-4)). Besides, the hydroxymethine proton (δ 3.86 (1H, d, J=3.4 Hz, H-3)) and the methine proton (δ 3.65 (1H, t, J=2.6 Hz, H-4)) are adjacent and are coupled to each other.

The HMBC data of Product Gh-1050 show that: the hydroxymethine proton (δ 3.86 (1H, d, J=3.1 Hz, H-3)) is correlated with not only two quaternary carbons (δ 79.48 (C-2) and δ 100.23 (C-5)) but also two methine groups (δ 36.69 (C-4) and δ 48.27 (C-37)); and δ 3.65 (H-4) is correlated not only with δ 21.98 (C-38), δ 48.27 (C-37), δ 79.48 (C-2), δ 100.23 (C-5), δ 162.82 (C-6) and δ 100.12 (C-7), but also with δ 71.37 (C-3). In addition, the methylene protons (δ 2.03 (H$_1$-20) and δ 1.60 (H$_2$-20)) are correlated with δ 79.48 (C-2), δ 48.27 (C-37), δ 23.66 (C-19) and δ 71.37 (C-3); and δ 1.49 (H-19) is correlated with δ 79.48 (C-2), δ 71.37 (C-3), δ 21.98 (C-36) and an aromatic carbon (δ 163.38 (C-18)). Accordingly, it can be known that the hydroxyl group is connected to C-3; C-2 is connected to C-18 of an aromatic ring via an ether bond; and C-4 is connected to C-5 of the aromatic ring.

The NOESY data of Product Gh-1050 show that: δ 7.47 (H-10) is correlated with δ 3.49 (H-11); δ 3.49 (H-11) is correlated with δ 2.31 (H$_1$-21); δ 1.39 (H$_2$-21) is correlated with δ 2.55 (H-22); both δ 2.31 (H$_1$-21) and δ 2.55 (H-22) are correlated with δ 1.29 (H-24); and δ 5.57 (H-27) is correlated with δ 1.62 (H-29), evidencing that: the stereostructure of Product Gh-1050 in this part is identical to that of gambogic acid or gambogellic acid, i.e., in a 11S,13R, 14S,22S configuration, which includes H-27 and carboxyl group (C-30) in a trans relationship, and a double bond $\Delta^{27,28}$ in a Z configuration. The NOESY data of Product Gh-1050 also reveal that in addition to being correlated with δ 3.65 (H-4) and δ 1.31 (H-36), δ 2.29 (H-37) is correlated with δ 3.86 (H-3) and δ 1.60 (H$_2$-20), evidencing that the monoterpene ring has a chair conformation with 1,3-diaxial interaction, in which H-37 and H-3 are in an axial orientation, and both the methyl group (C-19) and the isopropenyl group are in an equatorial orientation. Since the hydroxymethine proton (H-3) is in an axial orientation, the C-3 hydroxyl group is in an equatorial orientation (an α-orientation), and C-3 is in a S configuration. In addition, since δ 1.62 (H-29) is not correlated with δ 4.63 (H$_1$-40) and δ 4.29 (H$_2$-40), C-2 is in an R configuration. In view of the aforesaid, it can be known that the monoterpene moiety is in a 2R,3S,4R,37S configuration.

Based on the above information, Product Gh-1050 is identified to be a new compound having the following chemical structure:

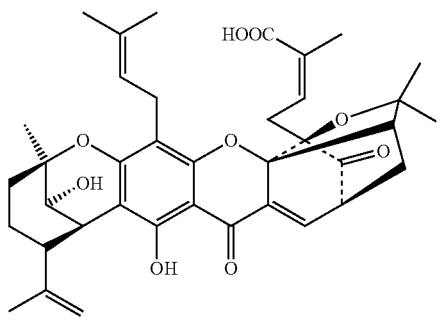

Product Gh-1050 is identified by the name "3α-hydroxygambogellic acid" {IUPAC nomenclature: [2-butenoic acid, 2-methyl-4-[(1R,3aS,5S,9R,10S,13R,16aS,17S)-3a,4,5,7,10,11,12,13-octahydro-8,17-dihydroxy-3,3,13-trimethyl-15-(3-methyl-2-butenyl)-10-(1-methylethenyl)-7,18-dioxo-1,5:9,13-dimethano-1H,3H,9H-furo[3.4-g]oxocino[3.2-b]xanthen-1-yl]-,(2Z)-]}.

25. Product Gh-3291:

Product Gh-3291, which was purified from eluate 7 of fraction 1, was determined to have the following properties:

Yellow powder; mp 103~106° C.

EIMS m/z (relative intensity): 644 [M]+ (10), 626 (10), 616 (12), 545 (67), 517 (19), 471 (15), 459 (6), 419 (10), 389 (21), 349 (11), 347 (20), 309 (9), 295 (17), 271 (13), 253 (20), 245 (26), 227 (21), 215 (56), 189 (23), 171 (11), 147 (16), 129 (28), 105 (35), 99 (50), 84 (43), 69 (84), 55 (100); HREIMS [M]+ m/z: 644.2991; calculated for $C_{38}H_{44}O_9$, 644.2985.

¹H-NMR (600 MHz, CDCl₃): δ 12.76 (1H, s, OH-6), 7.53 (1H, d, J=7.0 Hz, H-10), 6.60 (1H, d, J=10.2 Hz, H-4), 6.06 (1H, t, J=7.6 Hz, H-27), 5.36 (1H, d, J=10.3 Hz, H-3), 5.00 (1H, br t, J=6.3 Hz, H-32), 4.89 (1H, s, H₁-40), 4.81 (1H, d, J=1.0 Hz, H₂-40), 4.00 (1H, t, J=6.2 Hz, H-37), 3.46 (1H, dd, J=6.4, 5.1 Hz, H-11), 3.28 (1H, dd, J=14.9, 8.1 Hz, H₁-31), 3.13 (1H, br dd, J=14.6, 4.7 Hz, H₂-31), 2.93 (1H, dd, J=16.3, 7.9 Hz, H₁-26), 2.87 (1H, dd, J=16.0, 7.6 Hz, H₂-26), 2.51 (1H, d, J=9.3 Hz, H-22), 2.30 (1H, dd, J=13.5, 4.7 Hz, H₁-21), 1.80 (1H, m, H₁-20), 1.73 (3H, s, H-29), 1.71 (3H, s, H-25), 1.68 (3H, s, H-34), 1.67 (1H, m, H₁-36), 1.66 (3H, m, H-39), 1.62 (3H, s, H-35), 1.61 (1H, m, H₂-36), 1.54 (1H, m, H₂-20), 1.39 (3H, s, H-19), 1.38 (1H, m, H₂-21), 1.27 (3H, s, H-24).

¹³C-NMR (150 MHz, CDCl₃): δ 203.19 (C-12), 178.90 (C-8), 169.81 (C-30), 161.29 (C-18), 157.61 (C-16), 157.42 (C-6), 147.09 (C-38), 137.26 (C-27), 135.40 (C-10), 133.31 (C-9), 131.65 (C-33), 127.90 (C-28), 124.41 (C-3), 122.27 (C-32), 116.10 (C-4), 111.34 (C-40), 107.64 (C-17), 102.63 (C-5), 100.50 (C-7), 90.91 (C-14), 84.03 (C-23), 83.73 (C-13), 81.07 (C-2), 75.80 (C-37), 49.00 (C-22), 46.83 (C-11), 37.71 (C-20), 29.82 (C-25), 29.29 (C-36), 29.05 (C-26), 28.83 (C-24), 27.73 (C-19), 25.63 (C-35), 25.15 (C-21), 21.58 (C-31), 20.76 (C-29), 18.11 (C-34), 17.45 (C-39).

The EIMS data of Product Gh-3291 show a molecular ion peak [M]⁺ at m/z 644, and the HREIMS data of Product Gh-3291 show [M]⁺ at m/z 644.2991, indicating that Product Gh-3291 has a molecular formula of $C_{38}H_{44}O_9$, which has 16 more mass units than the molecular formula of gambogic acid.

The ¹H-NMR, ¹³C-NMR and HMQC data of Product Gh-3291 show that Product Gh-3291 has a C-2 side chain different from that of gambogic acid, namely, a 3-hydroxy-4-methyl-4-pentenyl group in lieu of the 4-methyl-3-pentenyl group in gambogic acid. The ¹H-NMR and ¹³C-NMR data of Product Gh-3291 also reveal that Product Gh-3291 has a secondary hydroxy group (δ 4.00 (1H, t, J=6.2 Hz) and δ 75.80) and an exo-methylene group (δ 4.89 (1H, s), δ 4.81 (1H, d), and δ 111.34).

The HMBC data of Product Gh-3291 show that: in addition to being correlated with δ 111.34 (C-40) and δ 147.09 (C-38), the hydroxymethine proton (δ 4.00) is correlated with δ 17.45 (C-39), δ 29.29 (C-36) and δ 37.71 (C-20); in addition to being correlated with δ 37.71 (C-20), the methyl proton (δ 1.39 (H-19)) is correlated with δ 81.07 (C-2) and δ 124.41 (C-3); and δ 5.36 (H-3) is correlated with δ 81.07 (C-2), δ 27.73 (C-19) and δ 37.71 (C-20).

The ¹H-¹H COSY data of Product Gh-3291 show that: δ 4.00 (1H, t, J=6.2 Hz, H-37) is coupled to the methylene protons (δ 1.67 (H₁-36) and 61.61 (H₂-36)), evidencing that the hydroxy group is attached to C-37.

The NOESY data of Product Gh-3291 show that: δ 7.53 (H-10) is correlated with δ 3.46 (H-11); δ 3.46 (H-11) is correlated with δ 2.30 (H₁-21); δ 1.38 (H₂-21) is correlated with δ 2.51 (H-22) and δ 1.27 (H-24); and δ 6.06 (H-27) is correlated with 661.73 (H-29), evidencing that the stereostructure of Product Gh-3291 in this part is identical to that of gambogic acid, i.e., in a 11S,13R,14S,22S configuration, which includes H-27 and carboxyl group (C-30) in a trans relationship, and a double bond $\Delta^{27,28}$ in a Z configuration.

The NOESY data of Product Gh-3291 also reveal that: the hydroxymethine proton (δ 4.00 (H-37)) is correlated not only with δ 4.89 (H₁-40) and δ 1.66 (H-39), but also with the protons of two methylene groups (δ 1.80 (H₁-20), δ 1.54 (H₂-20), δ 1.67 (H₁-36) and δ 1.61 (H₂-36)); and δ 5.36 (H-3) is correlated with δ 1.39 (H-19), δ 1.80 (H₁-20) and δ 1.54 (H₂-20), δ 1.67 (H₁-36), and δ 1.61 (H₂-36). Besides, since δ 1.39 (H-19) is correlated with δ 1.73 (H-29), C-2 is in an R configuration.

Based on the above information, Product Gh-3291 is identified to be a new compound having the following chemical structure:

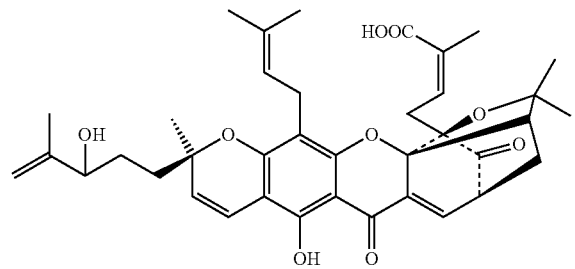

Product Gh-3291 is identified by the name "formoxanthone D" {IUPAC nomenclature: [2-butenoic acid, 2-methyl-4-[(1R,3aS,5S,11R,14aS)-3a,4,5,7-tetrahydro-8-hydroxy-3,3,11-trimethyl-13-(3-methyl-2-butenyl)-11-(3-hydroxy-4-methyl-4-pentenyl)-7,15-dioxo-1,5-methano-1H,3H,11H-furo[3.4-g]pyrano[3.2-b]xanthen-1-yl]-,(2Z)-]}.

26. Product Gh-3352:

Product Gh-3352, which was purified from eluate 12 of fraction 1, was determined to have the following properties:

Yellow powder; mp 194~197° C.

FABMS m/z (relative intensity): 645 [M+H]⁺ (11), 634 (10), 591 (11), 575 (13), 574 (22), 573 (45), 559 (12), 545 (16), 544 (11), 487 (15), 417 (16), 405 (11), 391 (13), 375 (10), 371 (10), 349 (11), 338 (12), 321 (12), 307 (27), 299 (17), 295 (17), 289 (23), 259 (19), 255 (21), 219 (24), 215 (20), 213 (27), 189 (18), 176 (21), 165 (24), 154 (100), 136 (92), 121 (30), 107 (56), 91 (55), 89 (50), 77 (59), 69 (69), 57 (69), 55 (66); HRFABMS [M+H]⁺ m/z: 645.3066; calculated for $C_{38}H_{45}O_9$, 645.3064.

¹H-NMR (600 MHz, CDCl₃): δ 12.92 (1H, s, OH-6), 7.52 (1H, d, J=6.9 Hz, H-10), 6.66 (1H, d, J=10.1 Hz, H-4), 5.58 (1H, br t, J=6.5 Hz, H-27), 5.45 (1H, d, J=10.2 Hz, H-3), 5.03 (1H, t, J=7.0 Hz, H-37), 3.79 (1H, dd, J=9.2, 3.1 Hz, H-32), 3.50 (1H, dd, J=6.8, 4.7 Hz, H-11), 3.30 (1H, dd, J=14.8, 10.1 Hz, H₁-26), 2.90 (1H, ddd, J=15.3, 5.6, 1.3 Hz, H₂-26), 2.85 (1H, dd, J=13.9, 9.7 Hz, H₁-31), 2.71 (1H, dd, J=13.8, 3.4 Hz, H₂-31), 2.49 (1H, d, J=9.3 Hz, H-22), 2.33 (1H, dd, J=13.5, 4.7 Hz, H₁-21), 2.05 (2H, m, H-36), 1.74 (3H, s, H-25), 1.73 (1H, m, H₁-20), 1.69 (3H, s, H-29), 1.66 (1H, m, H₂-20), 1.63 (3H, s, H-39), 1.53 (3H, s, H-40), 1.45 (3H, s, H-19), 1.33 (1H, m, H₂-21), 1.29 (3H, s, H-34), 1.27 (3H, s, H-35), 1.25 (3H, s, H-24).

¹³C-NMR (150 MHz, CDCl₃): δ 202.89 (C-12), 179.05 (C-8), 168.89 (C-30), 161.34 (C-18), 158.49 (C-6), 158.28 (C-16), 136.09 (C-27), 135.01 (C-10), 133.19 (C-9), 132.17 (C-38), 129.31 (C-28), 124.75 (C-3), 123.46 (C-37), 115.93 (C-4), 104.83 (C-17), 102.92 (C-5), 100.67 (C-7), 90.77 (C-14), 84.28 (C-13), 83.86 (C-23), 81.81 (C-2), 77.20 (C-32), 73.24 (C-33), 49.12 (C-22), 47.04 (C-11), 41.72 (C-20), 30.56 (C-25), 29.65 (C-26), 28.89 (C-24), 27.18 (C-19), 25.89 (C-31), 25.69 (C-39), 25.63 (C-35), 25.36 (C-21), 23.75 (C-34), 22.66 (C-36), 20.73 (C-29), 17.59 (C-40).

The HRFABMS data of Product Gh-3352 show a pseudomolecular ion peak [M+H]⁺ at m/z 645.3066, suggesting that Product Gh-3352 has a molecular formula of $C_{38}H_{44}O_9$, which has sixteen more mass units than the molecular formula of gambogic acid.

The $^1$H-NMR, $^{13}$C-NMR and HMQC data of Product Gh-3352 show that Product Gh-3352 has a C-17 side chain different from that of gambogic acid, namely, a 2,3-epoxy-3-methylbutyl group in lieu of the 3-methyl-2-butenyl group in gambogic acid. As compared to gambogic acid, the unsaturation number of Product Gh-3352 remains unchanged.

The $^1$H-$^1$H COSY, HMQC and HMBC data of Product Gh-3352 show that: an oxymethine proton (δ 3.79 (1H, dd, J=9.2, 3.1 Hz)) is coupled to a methylene proton (δ 2.85 (1H, dd, J=13.9, 9.7 Hz, $H_1$-31)); and δ 2.85 is coupled to another methylene proton (δ 2.71 (1H, dd, J=13.8, 3.4 Hz, $H_2$-31)). Besides, Product Gh-3352 has two tertiary methyl groups (δ 1.29 (3H, s, H-34) and δ 1.27 (3H, s, H-35)) attached to an oxygen-bearing quaternary carbon. It can be known from the signals of the oxygen-bearing quaternary carbon (δ 73.24 (C-33)), the oxymethine carbon (δ 77.20 (CH)) and the methylene carbon (δ 25.89 ($CH_2$), C-31) that an epoxy group is located at C-32 and C-33.

The HMBC data of Product Gh-3352 show that δ 2.85 ($H_1$-31) is correlated with δ 77.20 (C-32) and δ 104.83 (C-17), evidencing that the side attached to C-17 is a 2,3-epoxy-3-methylbutyl group.

The NOESY data of Product Gh-3352 show that: δ 7.52 (H-10) is correlated with δ 3.50 (H-11); δ 3.50 (H-11) is correlated with δ 2.33 ($H_1$-21) and δ 1.33 ($H_2$-21); δ 1.33 ($H_2$-21) and δ 2.49 (H-22) are correlated; δ 2.49 (H-22) is correlated with δ 1.74 (H-25); and δ 5.58 (H-27) is correlated with δ 1.69 (H-29), evidencing that the stereostructure of Product Gh-3352 in this part is identical to that of gambogic acid, i.e., in a 11S,13R,14S,22S configuration, which includes H-27 and carboxyl group (C-30) in a trans relationship, and a double bond $\Delta^{27,28}$ in a Z configuration. In addition, since δ 1.69 (H-29) is correlated with δ 1.45 (H-19), C-2 is in an R configuration.

Based on the above information, Product Gh-3352 is identified to be a new compound having the following chemical structure:

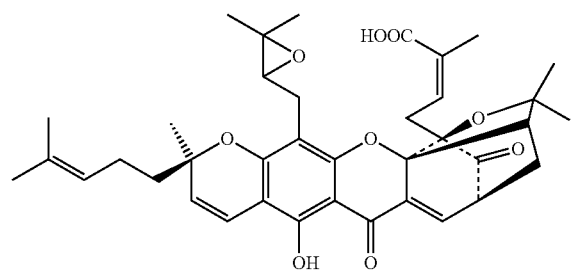

Product Gh-3352 is identified by the name "formoxanthone E" {IUPAC nomenclature: [2-butenoic acid, 2-methyl-4-[(1R,3aS,5S,11R,14aS)-3a,4,5,7-tetrahydro-8-hydroxy-3,3,11-trimethyl-13-(2,3-epoxy-3-methyl butyl)-11-(4-methyl-3-pentenyl)-7,15-dioxo-1,5-methano-1H,3H,11H-furo[3.4-g]pyrano[3.2-b]xanthen-1-yl]-,(2Z)-]}.

27. Product Gh-3351:

Product Gh-3351, which was purified from eluate 10 of fraction 1, was determined to have the following properties:

Yellow powder; mp 168~171° C.

EIMS m/z (relative intensity): 621 (6), 603 (17), 589 (100), 577 (23), 561 (19), 503 (47), 467 (6), 423 (8), 381 (5), 339 (4), 315 (15), 231 (7), 213 (9), 135 (4), 69 (15); HRFABMS [M+H]$^+$ m/z: 645.3070; calculated for $C_{38}H_{45}O_9$, 645.3064.

$^1$H-NMR (600 MHz, CDCl$_3$): δ 12.91 (1H, s, OH-6), 7.51 (1H, d, J=6.9 Hz, H-10), 6.49 (1H, d, J=10.1 Hz, H-4), 5.56 (1H, br t, J=7.3 Hz, H-27), 5.43 (1H, d, J=10.2 Hz, H-3), 5.03 (1H, t, J=7.0 Hz, H-37), 3.76 (1H, br d, J=7.0 Hz, H-32), 3.50 (1H, dd, J=6.6, 4.9 Hz, H-11), 3.29 (1H, dd, J=15.2, 10.1 Hz, $H_1$-26), 2.89 (1H, ddd, J=15.3, 5.5, 1.5 Hz, $H_2$-26), 2.82 (1H, dd, J=13.9, 9.9 Hz, $H_1$-31), 2.69 (1H, br d, J=12.7 Hz, $H_2$-31), 2.48 (1H, d, J=9.3 Hz, H-22), 2.32 (1H, dd, J=13.5, 4.0 Hz, $H_1$-21), 2.03 (2H, m, H-36), 1.73 (3H, s, H-25), 1.68 (3H, s, H-29), 1.67 (2H, m, H-20), 1.62 (3H, s, H-39), 1.53 (3H, s, H-40), 1.43 (3H, s, H-19), 1.30 (1H, m, $H_2$-21), 1.28 (3H, s, H-34), 1.26 (3H, s, H-35), 1.24 (3H, s, H-24).

$^{13}$C-NMR (150 MHz, CDCl$_3$): δ 202.99 (C-12), 179.03 (C-8), 169.60 (C-30), 161.37 (C-18), 158.46 (C-6), 158.25 (C-16), 135.76 (C-27), 134.92 (C-10), 133.21 (C-9), 132.14 (C-38), 129.58 (C-28), 124.72 (C-3), 123.47 (C-37), 115.90 (C-4), 104.81 (C-17), 102.88 (C-5), 100.63 (C-7), 90.74 (C-14), 84.26 (C-13), 83.79 (C-23), 81.75 (C-2), 77.15 (C-32), 73.25 (C-33), 49.11 (C-22), 47.04 (C-11), 41.71 (C-20), 30.56 (C-25), 29.69 (C-26), 28.88 (C-24), 27.13 (C-19), 25.92 (C-31), 25.89 (C-39), 25.63 (C-35), 25.36 (C-21), 23.44 (C-34), 22.65 (C-36), 20.74 (C-29), 17.59 (C-40).

The EIMS data of Product Gh-3351 show a base peak at m/z 589 (100), and the HRFABMS data of Product Gh-3351 show a pseudomolecular ion peak [M+H]$^+$ at m/z 645.3070, indicating that Product Gh-3351 has a molecular formula of $C_{38}H_{44}O_9$, which has sixteen more mass units than the molecular formula of gambogic acid.

The $^1$H-NMR, $^{13}$C-NMR and HMQC data of Product Gh-3351 show that Product Gh-3351 has a C-17 side chain different from that of gambogic acid, namely a 2,3-epoxy-3-methylbutyl group in lieu of the 3-methyl-2-butenyl group in gambogic acid. As compared to gambogic acid, the unsaturation number of Product Gh-3351 remains unchanged.

The $^1$H-$^1$H COSY, HMQC and HMBC data of Product Gh-3351 show that: an oxymethine proton (δ 3.76 (1H, br d, J=7.0 Hz)) is coupled to a methylene proton (δ 2.82 (1H, dd, J=13.9, 9.9 Hz, $H_1$-31)); and δ 2.82 is coupled to another methylene proton (δ 2.69 (1H, br d, J=12.7 Hz, $H_2$-31)). Besides, Product Gh-3351 has two oxygen-bearing tertiary methyl protons (δ 1.28 (3H, s, H-34) and δ 1.26 (3H, s, H-35)]. Based on the signals of the oxygen-bearing quaternary carbon (δ 73.25 (C-33)), the oxymethine group (δ 77.15 (C-32)) and the methylene group (δ 25.92 (C-31)), it can be known that an epoxy group is located at C-32 and C-33.

The HMBC data of Product Gh-3351 show that: δ 2.82 ($H_1$-31) is correlated with δ 77.15 (C-32), δ 102.88 (C-5), δ 104.81 (C-17), δ 158.25 (C-16) and δ 161.37 (C-18), evidencing that the side chain attached to C-17 is a 2,3-epoxy-3-methylbutyl group.

The NOESY data of Product Gh-3351 show that: δ 7.51 (H-10) is correlated with δ 3.50 (H-11); δ 3.50 (H-11) is correlated with δ 2.32 ($H_1$-21) and δ 1.30 ($H_2$-21); δ 1.30 ($H_2$-21) is correlated with δ 2.48 (H-22); δ 2.48 (H-22) is correlated with δ 1.73 (H-25); and δ 5.56 (H-27) is correlated with δ 1.68 (H-29), evidencing that the stereostructure of Product Gh-3351 in this part is identical to that of gambogic acid, i.e., in a 11S,13R,14S,22S configuration, which includes H-27 and carboxyl group (C-30) in a trans relationship, and a double bond $\Delta^{27,28}$ in a Z configuration.

In addition, since δ 1.68 (H-29) is correlated with δ 2.03 (H-36), C-2 is in an S configuration.

Based on the above information, product Gh-3351 is identified to be a new compound having the following chemical structure:

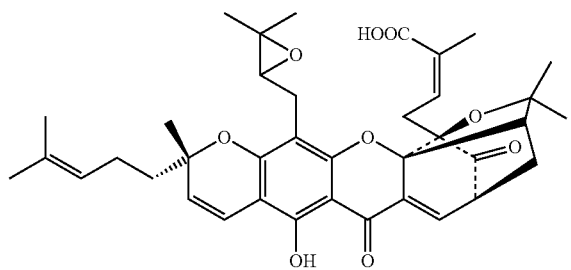

Product Gh-3351 is identified by the name "epiformoxanthone E" {IUPAC nomenclature: [2-butenoic acid, 2-methyl-4-[(1R,3aS,5S,11S,14aS)-3a,4,5,7-tetrahydro-8-hydroxy-3,3,11-trimethyl-13-(2,3-epoxy-3-methylbutyl)-11-(4-methyl-3-pentenyl)-7,15-dioxo-1,5-methano-1H,3H,11H-furo[3.4-g]pyrano[3.2-b]xanthen-1-yl]-,(2Z)-]}.

28. Product Gh-1052:

Product Gh-1052, which was purified from eluate 9 of fraction 1, was determined to have the following properties:

Yellow powder; mp 83~85° C.

EIMS m/z (relative intensity): 662 [M]$^+$ (6), 634 (8), 579 (100), 551 (16), 545 (9), 507 (14), 489 (6), 417 (12), 389 (4), 349 (4), 295 (5), 245 (8), 214.9 (14), 189 (8), 147 (4), 99 (7), 69 (29); HREIMS [M]$^+$ m/z: 662.3096; calculated for $C_{38}H_{46}O_{10}$, 662.3091.

$^1$H-NMR (600 MHz, CDCl$_3$): δ 12.92 (1H, s, OH-6), 7.52 (1H, d, J=7.0 Hz, H-10), 6.65 (1H, d, J=10.2 Hz, H-4), 5.63 (1H, t, J=7.4 Hz, H-27), 5.46 (1H, d, J=10.3 Hz, H-3), 5.07 (1H, t, J=7.1 Hz, H-37), 3.74 (1H, dd, J=10.0, 3.4 Hz, H-32), 3.49 (1H, dd, J=6.7, 4.7 Hz, H-11), 3.25 (1H, dd, J=15.2, 9.9 Hz, H$_1$-26), 2.89 (1H, ddd, J=15.3, 5.9, 1.7 Hz, H$_2$-26), 2.84 (1H, dd, J=13.9, 10.1 Hz, H$_1$-31), 2.72 (1H, dd, J=13.9, 3.4 Hz, H$_2$-31), 2.49 (1H, d, J=9.3 Hz, H-22), 2.32 (1H, dd, J=13.5, 4.7 Hz, H$_1$-21), 2.07 (2H, m, H-36), 1.79 (1H, m, H$_1$-20), 1.73 (3H, s, H-25), 1.69 (3H, s, H-29), 1.67 (1H, m, H$_2$-20), 1.65 (3H, s, H-39), 1.57 (3H, s, H-40), 1.37 (3H, s, H-19), 1.33 (1H, dd, J=13.5, 9.6 Hz, H$_2$-21), 1.27 (3H, s, H-35), 1.26 (3H, s, H-24), 1.24 (3H, s, H-34).

$^{13}$C-NMR (150 MHz, CDCl$_3$): δ 202.93 (C-12), 179.10 (C-8), 169.18 (C-30), 161.47 (C-18), 158.49 (C-6), 158.22 (C-16), 136.45 (C-27), 135.16 (C-10), 133.12 (C-9), 132.66 (C-38), 129.08 (C-28), 124.56 (C-3), 123.36 (C-37), 116.12 (C-4), 104.92 (C-17), 102.95 (C-5), 100.63 (C-7), 90.82 (C-14), 84.18 (C-13), 83.82 (C-23), 81.76 (C-2), 77.11 (C-32), 73.09 (C-33), 49.08 (C-22), 47.03 (C-11), 41.74 (C-20), 30.62 (C-25), 29.54 (C-26), 28.83 (C-24), 27.21 (C-19), 25.87 (C-35), 25.68 (C-31), 25.65 (C-39), 25.33 (C-21), 23.65 (C-34), 22.91 (C-36), 20.74 (C-29), 17.71 (C-40).

The EIMS data of Product Gh-1052 show a molecular ion peak [M]$^+$ at m/z 662 and a base peak at m/z 579 (100), and the HREIMS data of Product Gh-1052 show [M]$^+$ at m/z 662.3096, indicating that Product Gh-1052 has a molecular formula of $C_{38}H_{46}O_{10}$, which has thirty-four more mass units than the molecular formula of gambogic acid.

The $^1$H-NMR, $^{13}$C-NMR and HMQC data of Product Gh-1052 show that Product Gh-1052 has a C-17 side chain different from that of gambogic acid, namely, a 2,3-dihydroxy-3-methylbutyl group in lieu of the 3-methyl-2-butenyl group in gambogic acid.

The $^1$H-NMR and $^{13}$C-NMR data of Product Gh-1052 show that Product Gh-1052 has a secondary hydroxy group (δ 3.74 (1H, dd, J=10.0, 3.4 Hz) and δ 77.11] and an oxygen-bearing quaternary carbon (δ 73.09). In addition, the $^1$H-$^1$H COSY data of Product Gh-1052 show that a hydroxymethine proton (δ 3.74 (1H, dd, J=10.0, 3.4 Hz)) is coupled to two methylene protons (δ 2.84 (1H, dd, J=13.9, 10.1 Hz, H$_1$-31) and δ 2.72 (1H, dd, J=13.9, 3.4 Hz, H$_2$-31)).

The HMQC data of Product Gh-1052 show that: C-31 (δ 25.68) is a methylene group; the secondary hydroxy group is connected to C-32 (δ 77.11); a tertiary hydroxy group is connected to C-33 (δ 73.09); and C-35 (δ 25.87) and C-34 (δ 23.65) are tertiary methyl groups.

The HMBC data of Product Gh-1052 show that: δ 3.74 (H-32) is correlated with δ 73.09 (C-33) and δ 23.65 (C-34); both δ 2.84 (H$_1$-31) and δ 2.72 (H$_2$-31) are correlated with δ 104.92 (C-17), δ 161.47 (C-18), δ 158.22 (C-16) and δ 77.11 (C-32); H$_1$-31 is also correlated with δ 73.09 (C-33); δ 1.24 (H-34) and δ 1.27 (H-35) are both correlated with δ 77.11 (C-32) and δ 73.09 (C-33); H-34 is also correlated with δ 25.87 (C-35); and H-35 is correlated with δ 23.65 (C-34), evidencing that the side chain attached to C-17 is a 2,3-dihydroxy-3-methylbutyl group.

The NOESY data of Product Gh-1052 show that: δ 7.52 (H-10) is correlated with δ 3.49 (H-11); δ 3.49 (H-11) is correlated with δ 2.32 (H$_1$-21) and δ 1.33 (H$_2$-21); δ 1.33 (H$_2$-21) is correlated with δ 2.49 (H-22); δ 2.49 (H-22) is correlated with δ 1.73 (H-25); and δ 5.63 (H-27) is correlated with δ 1.69 (H-29), evidencing that the stereostructure of Product Gh-1052 in this part is identical to that of gambogic acid, i.e., in a 11S,13R,14S,22S configuration, which includes H-27 and carboxyl group (C-30) in a trans relationship, and a double bond $\Delta^{27,28}$ in a Z configuration. In addition, since δ 1.37 (H-19) is correlated with δ 1.69 (H-29), C-2 is in an R configuration.

Based on the above information, Product Gh-1052 is identified to be a new compound having the following chemical structure:

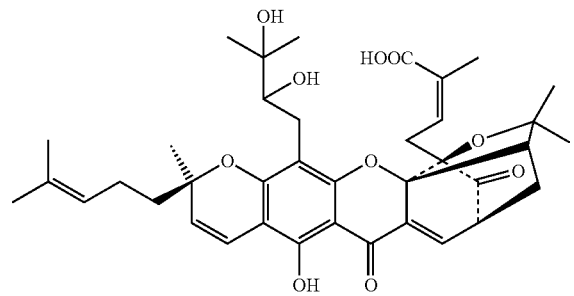

Product Gh-1052 is identified by the name "formoxanthone F" {IUPAC nomenclature: [2-butenoic acid, 2-methyl-4-[(1R,3aS,5S,11R,14aS)-3a,4,5,7-tetrahydro-8-hydroxy-3,3,11-trimethyl-13-(2,3-dihydroxy-3-methylbutyl)-11-(4-methyl-3-pentenyl)-7,15-dioxo-1,5-methano-1H,3H,11H-furo[3.4-g]pyrano[3.2-b]xanthen-1-yl]-,(2Z)-]}.

29. Product Gh-1036:

Product Gh-1036, which was purified from eluate 6 of fraction 1, was determined to have the following properties:

Yellow powder; mp 76~78° C.

EIMS m/z (relative intensity): 662 [M]$^+$ (13), 634 (7), 579 (100), 551 (13), 545 (10), 507 (12), 489 (5), 417 (9), 375 (3), 349 (3), 295 (4), 245 (8), 215 (8), 213 (7), 147 (4), 105 (5), 69 (19); HREIMS [M]$^+$ m/z 662.3098; calculated for $C_{38}H_{46}O_{10}$, 662.3091.

$^1$H-NMR (600 MHz, CDCl$_3$): δ 12.91 (1H, s, OH-6), 7.52 (1H, d, J=6.9 Hz, H-10), 6.66 (1H, d, J=10.0 Hz, H-4), 5.53 (1H, br t, J=5.2 Hz, H-27), 5.47 (1H, d, J=10.1 Hz, H-3), 5.08 (1H, t, J=6.9 Hz, H-37), 3.74 (1H, dd, J=11.2, 2.6 Hz, H-32), 3.49 (1H, t, J=5.6 Hz, H-11), 3.27 (1H, dd, J=15.0, 10.4 Hz, H$_1$-26), 2.87 (1H, dd, J=13.6, 11.7 Hz, H$_1$-31), 2.82 (1H, br dd, J=15.3, 3.8 Hz, H$_2$-26), 2.72 (1H, dd, J=13.7, 2.8 Hz, H$_2$-31), 2.48 (1H, d, J=9.2 Hz, H-22), 2.32 (1H, dd, J=13.5, 4.5 Hz, H$_1$-21), 2.10 (2H, m, H-36), 1.78 (1H, m, H$_1$-20), 1.702 (3H, s, H-25), 1.697 (1H, m, H$_2$-20), 1.653 (3H, s, H-29), 1.648 (3H, s, H-39), 1.58 (3H, s, H-40), 1.35 (3H, s, H-19), 1.33 (1H, m, H$_2$-21), 1.28 (3H, s, H-35), 1.25 (3H, s, H-24), 1.24 (3H, s, H-34).

$^{13}$C-NMR (150 MHz, CDCl$_3$): δ 202.96 (C-12), 179.04 (C-8), 168.66 (C-30), 161.45 (C-18), 158.35 (C-6), 158.28 (C-16), 135.28 (C-27), 134.98 (C-10), 133.19 (C-9), 132.39 (C-38), 129.46 (C-28), 124.77 (C-3), 123.52 (C-37), 116.07 (C-4), 104.54 (C-17), 103.19 (C-5), 100.64 (C-7), 90.87 (C-14), 84.28 (C-13), 83.60 (C-23), 81.71 (C-2), 76.57 (C-32), 73.06 (C-33), 49.07 (C-22), 46.99 (C-11), 41.68 (C-20), 30.76 (C-25), 29.96 (C-26), 28.86 (C-24), 26.79 (C-19), 26.29 (C-35), 25.63 (C-39), 25.42 (C-21), 24.62 (C-31), 23.56 (C-34), 22.82 (C-36), 20.52 (C-29), 17.62 (C-40).

The EIMS data of Product Gh-1036 show a molecular ion peak [M]$^+$ at m/z 662 and a base peak at m/z 579 (100), and the HREIMS data of Product Gh-1036 show [M]$^+$ at m/z 662.3098, indicating that Product Gh-1036 has a molecular formula of $C_{38}H_{46}O_{10}$, which has thirty-four more mass units than the molecular formula of gambogic acid.

The $^1$H-NMR, $^{13}$C-NMR and HMQC data of Product Gh-1036 show that Product Gh-1036 has a C-17 side chain different from that of gambogic acid, namely, a 2,3-dihydroxy-3-methylbutyl group in lieu of the 3-methyl-2-butenyl group in gambogic acid.

The $^1$H-NMR and $^{13}$C-NMR data of Product Gh-1036 show that Product Gh-1036 has a secondary hydroxy group (δ 3.74 (1H, dd, J=11.2, 2.6 Hz) and δ 76.57) and an oxygen-bearing quaternary carbon (δ 73.06).

In addition, the $^1$H-$^1$H COSY data of Product Gh-1036 show that a hydroxymethine proton (δ 3.74 (1H, dd, J=11.2, 2.6 Hz)) is coupled to two methylene protons (δ 2.87 (1H, dd, J=13.6, 11.7 Hz, H$_1$-31) and δ 2.72 (1H, dd, J=13.7, 2.8 Hz, H$_2$-31)).

The HMQC data of product Gh-1036 show that: C-31 (δ 24.62) is a methylene group; a secondary hydroxy group is connected to C-32 (δ 76.57); a tertiary hydroxy group is connected to C-33 (δ 73.06); and C-34 (δ 23.56) and C-35 (δ 26.29) are tertiary methyl groups.

The HMBC data of Product Gh-1036 show that: in addition to being correlated with δ 24.62 (C-31), δ 73.06 (C-33) and δ 23.56 (C-34), δ 3.74 (H-32) is correlated with δ 104.54 (C-17); and both δ 2.87 (H$_1$-31) and δ 2.72 (H$_2$-31) are correlated with δ 76.57 (C-32), δ 73.06 (C-33), δ 104.54 (C-17), δ 161.45 (C-18) and δ 158.28 (C-16), evidencing that the side chain attached to C-17 is a 2,3-dihydroxy-3-methylbutyl group.

The NOESY data of Product Gh-1036 show that: δ 7.52 (H-10) is correlated with δ 3.49 (H-11); δ 3.49 (H-11) is correlated with δ 2.32 (H$_1$-21) and δ 1.33 (H$_2$-21); δ 1.33 (H$_2$-21) is correlated with δ 2.48 (H-22); δ 2.48 (H-22) is correlated with δ 1.702 (H-25); and δ 5.53 (H-27) is correlated with δ 1.653 (H-29), evidencing that the stereostructure of Product Gh-1036 in this part is identical to that of gambogic acid, i.e., in a 11S,13R,14S,22S configuration, which includes H-27 and carboxyl group (C-30) in a trans relationship, and a double bond $\Delta^{27,28}$ in a Z configuration. In addition, since δ 1.653 (H-29) is correlated with δ 1.78 (H$_1$-20) and δ 2.10 (H-36), C-2 is in an S configuration.

Based on the above information, Product Gh-1036 is identified to be a new compound having the following chemical structure:

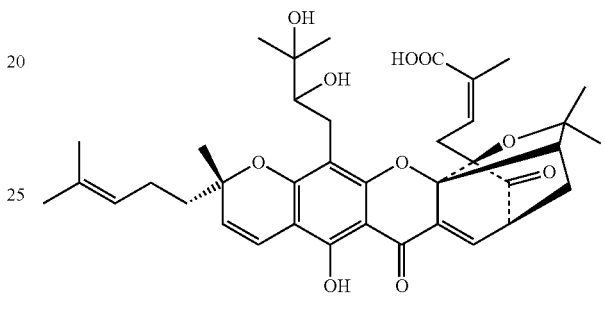

Product Gh-1036 is identified by the name "epiformoxanthone F" {IUPAC nomenclature: [2-butenoic acid, 2-methyl-4-[(1R,3aS,5S,11S,14aS)-3a,4,5,7-tetrahydro-8-hydroxy-3,3,11-trimethyl-13-(2,3-dihydroxy-3-methylbutyl)-11-(4-methyl-3-pentenyl)-7,15-dioxo-1,5-methano-1H,3H,11H-furo[3.4-g]pyrano[3.2-b]xanthen-1-yl]-,(2Z)-]}.

30. Product Gh-3353:

Product Gh-3353, which was purified from eluate 11 of fraction 1, was determined to have the following properties:

Yellow powder; mp 158~162° C.

EIMS m/z (relative intensity): 590 (32), 589 (100), 577 (24), 561 (19), 503 (44), 467 (6), 423 (8), 381 (5), 339 (4), 315 (8), 311 (3), 285 (2), 247 (4), 231 (6), 205 (2), 135 (4), 81 (3), 69 (14); HRFABMS [M+H]$^+$ m/z: 661.3019; calculated for $C_{38}H_{45}O_{10}$, 661.3013.

$^1$H-NMR (600 MHz, CDCl$_3$): δ 13.13 (1H, s, OH-6), 7.56 (1H, d, J=7.1 Hz, H-10), 6.62 (1H, d, J=10.1 Hz, H-4), 5.44 (1H, d, J=10.3 Hz, H-3), 5.15 (1H, d, J=8.9 Hz, H-31), 5.04 (1H, br t, J=3.5 Hz, H-37), 5.01 (1H, m, H-27), 4.70 (1H, d, J=8.9 Hz, H-32), 3.55 (1H, dd, J=6.6, 4.9 Hz, H-11), 3.42 (1H, t, J=13.4 Hz, H$_1$-26), 2.73 (1H, br d, J=13.9 Hz, H$_2$-26), 2.52 (1H, d, J=9.3 Hz, H-22), 2.36 (1H, dd, J=13.5, 7.7 Hz, H$_1$-21), 2.05 (2H, m, H-36), 1.82 (3H, s, H-25), 1.76 (1H, m, H$_1$-20), 1.64 (3H, s, H-35), 1.63 (1H, m, H$_2$-20), 1.62 (3H, s, H-39), 1.54 (3H, s, H-40), 1.49 (3H, s, H-29), 1.44 (6H, s, H-19, H-34), 1.27 (1H, m, H$_2$-21), 1.26 (3H, s, H-24).

$^{13}$C-NMR (150 MHz, CDCl$_3$): δ 202.26 (C-12), 179.10 (C-8), 166.33 (C-30), 161.08 (C-18), 159.90 (C-16), 158.73 (C-6), 134.79 (C-10), 132.77 (C-9), 132.73 (C-28), 132.09 (C-38), 128.48 (C-27), 124.60 (C-3), 123.55 (C-37), 115.48 (C-4), 105.98 (C-17), 101.92 (C-5), 99.90 (C-7), 91.89 (C-14), 84.63 (C-13), 83.75 (C-33), 83.70 (C-23), 82.16 (C-2), 76.83 (C-32), 67.26 (C-31), 49.47 (C-22), 46.71 (C-11), 41.97 (C-20), 31.14 (C-26), 30.13 (C-25), 29.42 (C-24), 27.60 (C-19), 26.05 (C-21), 25.63 (C-39), 23.89 (C-35), 22.43 (C-36), 19.98 (C-29), 18.80 (C-34), 17.66 (C-40).

The EIMS data of Product Gh-3353 show a base peak at m/z 589 (100), and the HRFABMS data of product Gh-3353 show a pseudomolecular ion peak [M+H]$^+$ at m/z 661.3019, indicating that Product Gh-3353 has a molecular formula of $C_{38}H_{44}O_{10}$, which has thirty-two more mass units than the molecular formula of gambogic acid.

The $^1$H-NMR, $^{13}$C-NMR and HMQC data of Product Gh-3353 show that Product Gh-3353 has a C-17 side chain different from that of gambogic acid, namely, a 1-hydroxy-2,3-epoxy-3-methylbutyl group in lieu of the 3-methyl-2-butenyl group in gambogic acid.

The $^1$H-NMR, $^{13}$C-NMR and $^1$H-$^1$H COSY data of Product Gh-3353 show that a hydroxymethine proton (δ 5.15 (1H, d, J=8.9 Hz)) is coupled to an oxymethine proton (δ 4.70 (1H, d, J=8.9 Hz)) on an epoxy group. Since the two vicinal oxymethine protons on an epoxy ring have a coupling constant (J) normally less than 5 Hz, the coupling constant of J=8.9 Hz should not represent the coupling of the two vicinal oxymethine protons on the epoxy ring.

The HMBC data of Product Gh-3353 show that: δ 5.15 is correlated with δ 161.08 (C-18), δ 159.90 (C-16), δ 105.98 (C-17) and δ 76.83 (C-32); and δ 4.70 is correlated with δ 83.75 (C-33), δ 18.80 (C-34), δ 23.89 (C-35) and δ 67.26 (C-31), evidencing that a hydroxy group is connected to C-31; an epoxy group is located at C-32 and C-33; and the side chain attached to C-17 is a 1-hydroxy-2,3-epoxy-3-methylbutyl group.

The NOESY data of Product Gh-3353 show that: δ 7.56 (H-10) is correlated with δ 3.55 (H-11); δ 3.55 (H-11) is correlated with δ 2.36 (H$_1$-21) and δ 1.27 (H$_2$-21); both δ 2.36 (H$_1$-21) and δ 1.27 (H$_2$-21) are correlated with δ 2.52 (H-22); δ 2.52 (H-22) is correlated with δ 1.82 (H-25) and δ 1.26 (H-24); δ 5.01 (H-27) is correlated with δ 1.49 (H-29); and δ 1.49 (H-29) is not correlated with δ 2.05 (H-36) or δ 1.76 (H$_1$-20), evidencing that the stereostructure of Product Gh-3353 in this part is identical to that of gambogic acid, i.e., in a 11S,13R,14S,22S configuration, which includes H-27 and carboxyl group (C-30) in a trans relationship, and a double bond $\Delta^{27,28}$ in a Z configuration. In addition, δ 5.04 (H-37) is correlated with δ 1.62 (H-39) and δ 1.54 (H-40), and δ 2.05 (H-36) is correlated with δ 1.76 (H$_1$-20). Since δ 1.49 (H-29) is not correlated with δ 2.05 (H-36) or δ 1.76 (H$_1$-20), C-2 has an R configuration.

Based on the above information, Product Gh-3353 is identified to be a new compound having the following chemical structure:

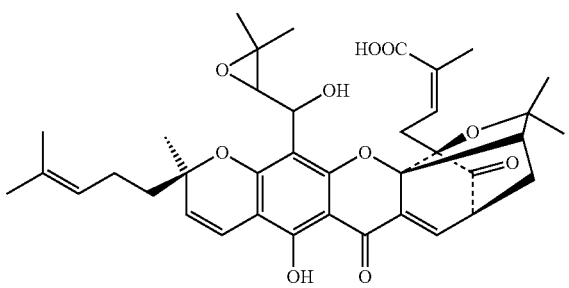

Product Gh-3353 is identified by the name "formoxanthone G" {IUPAC nomenclature: [2-butenoic acid, 2-methyl-4-[(1R,3aS,5S,11R,14aS)-3a,4,5,7-tetrahydro-8-hydroxy-3,3,11-trimethyl-13-(1-hydroxy-2,3-epoxy-3-methylbutyl)-11-(4-methyl-3-pentenyl)-7,15-dioxo-1,5-methano-1H,3H,11H-furo[3.4-g]pyrano[3.2-b]xanthen-1-yl]-,(2Z)-]}.

31. Product Gh-3311:

Product Gh-3311, which was purified from eluate 4 of fraction 1, was determined to have the following properties:

Yellow powder; mp 144~148° C.

EIMS m/z (relative intensity): 590 (7), 589 (18), 577 (5), 561 (9), 503 (11), 467 (2), 423 (2), 347 (5), 315 (3), 285 (3), 247 (6), 233 (13), 231 (22), 230 (16), 215 (8), 202 (4), 131 (6), 117 (100), 115 (19), 91 (12), 69 (14); HRFABMS [M+H]$^+$ m/z: 661.3010; calculated for $C_{38}H_{45}O_{10}$, 661.3013.

$^1$H-NMR (600 MHz, CDCl$_3$): δ 13.12 (1H, s, OH-6), 7.56 (1H, d, J=7.1 Hz, H-10), 6.65 (1H, d, J=10.0 Hz, H-4), 5.52 (1H, d, J=10.2 Hz, H-3), 5.17 (1H, d, J=9.0 Hz, H-31), 5.05 (1H, m, H-37), 5.03 (1H, m, H-27), 4.71 (1H, d, J=9.0 Hz, H-32), 3.56 (1H, dd, J=6.8, 4.8 Hz, H-11), 3.42 (1H, t, J=13.5 Hz, H$_1$-26), 2.74 (1H, br d, J=13.7 Hz, H$_2$-26), 2.54 (1H, d, J=9.3 Hz, H-22), 2.37 (1H, dd, J=13.5, 4.8 Hz, H$_1$-21), 2.05 (2H, m, H-36), 1.86 (1H, m, H$_1$-20), 1.83 (3H, s, H-25), 1.69 (1H, m, H$_2$-20), 1.66 (3H, s, H-39), 1.64 (3H, s, H-35), 1.56 (3H, s, H-40), 1.49 (3H, s, H-29), 1.45 (3H, s, H-34), 1.35 (3H, s, H-19), 1.28 (1H, m, H$_2$-21), 1.26 (3H, s, H-24).

$^{13}$C-NMR (150 MHz, CDCl$_3$): δ 202.22 (C-12), 179.25 (C-8), 166.30 (C-30), 160.99 (C-18), 159.85 (C-16), 158.80 (C-6), 134.86 (C-10), 132.81 (C-9), 132.75 (C-28), 132.17 (C-38), 128.54 (C-27), 125.25 (C-3), 123.50 (C-37), 116.08 (C-4), 106.57 (C-17), 102.68 (C-5), 100.01 (C-7), 91.92 (C-14), 84.65 (C-13), 83.80 (C-33), 83.66 (C-23), 81.92 (C-2), 76.98 (C-32), 67.16 (C-31), 49.47 (C-22), 46.75 (C-11), 41.64 (C-20), 31.16 (C-26), 30.15 (C-25), 29.43 (C-24), 26.90 (C-19), 26.08 (C-21), 25.67 (C-39), 23.83 (C-35), 23.21 (C-36), 19.89 (C-29), 18.91 (C-34), 17.72 (C-40).

The EIMS data of Product Gh-3311 show a base peak at m/z 117 (100) but no molecular ion peak [M]$^+$, and the HRFABMS data of Product Gh-3311 show a pseudomolecular ion peak [M+H]$^+$ at m/z 661.3010, indicating that Product Gh-3311 has a molecular formula of $C_{38}H_{44}O_{10}$, which has thirty-two more mass units compared to the molecular formula of gambogic acid. As compared to gambogic acid, the unsaturation number of Product Gh-3331 remains unchanged.

The $^1$H-NMR and $^{13}$C-NMR data of Product Gh-3311 show that Product Gh-3311 has a secondary hydroxy group (δ 5.17 (1H, d, J=9.0 Hz) and δ 67.16) and an epoxy group (δ 4.71 (1H, d, J=9.0 Hz) and δ 76.98). These $^1$H-NMR and $^{13}$C-NMR data of Product Gh-3311 are very similar to those of Product Gh-3353.

The $^1$H-$^1$H COSY data of Product Gh-3311 show that the hydroxymethine proton (δ 5.17 (1H, d, J=9.0 Hz)) is coupled to the oxymethine proton (δ 4.71 (1H, d, J=9.0 Hz)) of the epoxy group, with a coupling constant (J) of 9.0 Hz. Since the two vicinal oxymethine protons on an epoxy ring have a coupling constant (J) normally less than 5 Hz, the coupling constant of J=8.9 Hz should not represent the coupling of the two vicinal oxymethine protons on the epoxy ring.

The HMBC data of Product Gh-3311 show that: δ 5.17 is correlated with δ 160.99 (C-18), δ 159.85 (C-16), δ 106.57 (C-17) and δ 76.98 (C-32); and δ 4.71 is correlated with δ 83.80 (C-33), δ 18.91 (C-34) and δ 67.16 (C-31), evidencing that the hydroxy group is connected to C-31, the epoxy group is located at C-32 and C-33, and the side chain attached to C-17 is a 1-hydroxy-2,3-epoxy-3-methylbutyl group.

The NOESY data of Product Gh-3311 show that: δ 7.56 (H-10) is correlated with δ 3.56 (H-11); δ 3.56 (H-11) is correlated with δ 2.37 (H$_1$-21) and δ 1.28 (H$_2$-21); both δ

2.37 (H₁-21) and δ 1.28 (H₂-21) are correlated with δ 2.54 (H-22); δ 2.54 (H-22) is correlated with δ 1.83 (H-25) and δ 1.26 (H-24); and δ 5.03 (H-27) is correlated with δ 1.49 (H-29), evidencing that the stereostructure of Product Gh-3311 in this part is identical to that of gambogic acid, i.e., in a 11S,13R,14S,22S configuration, which includes H-27 and carboxyl group (C-30) in a trans relationship, and a double bond $\Delta^{27,28}$ in a Z configuration. In addition, since δ 1.49 (H-29) is correlated with δ 1.86 (H₁-20) and δ 1.69 (H₂-20), C-2 is in an S configuration.

Based on the above information, product Gh-3311 is identified to be a new compound having the following chemical structure:

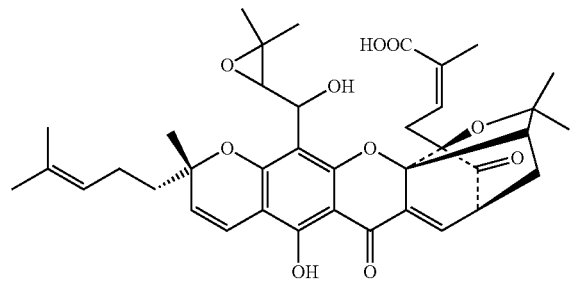

Product Gh-3311 is identified by the name "epiformoxanthone G" {IUPAC nomenclature: [2-butenoic acid, 2-methyl-4-[(1R,3aS,5S,11S,14aS)-3a,4,5,7-tetrahydro-8-hydroxy-3,3,11-trimethyl-13-(1-hydroxy-2,3-epoxy-3-methylbutyl)-11-(4-methyl-3-pentenyl)-7,15-dioxo-1,5-methano-1H,3H,11H-furo[3.4-g]pyrano[3.2-b]xanthen-1-yl]-,(2Z)-]}.

32. Product Gh-3272:

Product Gh-3272, which was purified from eluate 3 of fraction 1, was determined to have the following properties:

Yellow powder; mp 190-193° C.

EIMS m/z (relative intensity): 626 [M–H₂O]⁺ (2), 598 (2), 545 (100), 517 (3), 499 (2), 389 (3), 347 (3), 271 (2), 245 (4), 215 (11), 189 (4), 147 (1), 105 (2), 69 (2); HRFABMS [M–H₂O+H]⁺ m/z: 627.2961; calculated for C₃₈H₄₃O₈, 627.2958.

¹H-NMR (600 MHz, CDCl₃): δ 12.71 (1H, s, OH-6), 7.52 (1H, d, J=6.9 Hz, H-10), 6.57 (1H, d, J=10.1 Hz, H-4), 6.03 (1H, dt, J=7.5, 1.3 Hz, H-27), 5.59 (1H, d, J=15.7 Hz, H-37), 5.53 (1H, dt, J=15.6, 6.9 Hz, H-36), 5.34 (1H, d, J=10.1 Hz, H-3), 5.02 (1H, dt, J=6.2, 1.2 Hz, H-32), 3.46 (1H, dd, J=6.7, 4.6 Hz, H-11), 3.27 (1H, dd, J=14.7, 8.2 Hz, H₁-31), 3.11 (1H, br dd, J=14.6, 5.2 Hz, H₂-31), 2.94 (2H, br t, J=5.6 Hz, H-26), 2.49 (1H, d, J=9.3 Hz, H-22), 2.36 (1H, dd, J=13.9, 7.2 Hz, H₁-20), 2.29 (1H, dd, J=13.6, 4.8 Hz, H₁-21), 2.25 (1H, dd, J=14.0, 6.5 Hz, H₂-20), 1.72 (3H, s, H-34), 1.70 (3H, d, J=1.1 Hz, H-29), 1.67 (3H, s, H-25), 1.63 (3H, g, H-35), 1.38 (3H, s, H-19), 1.37 (1H, m, H₂-21), 1.27 (3H, s, H-24), 1.16 (6H, s, H-39, H-40).

¹³C-NMR (150 MHz, CDCl₃): δ 203.30 (C-12), 178.89 (C-8), 170.80 (C-30), 161.41 (C-18), 157.41 (C-16), 157.37 (C-6), 142.05 (C-37), 137.79 (C-27), 135.37 (C-10), 133.30 (C-9), 131.51 (C-33), 127.80 (C-28), 123.91 (C-3), 122.23 (C-32), 120.93 (C-36), 116.30 (C-4), 107.41 (C-17), 102.97 (C-5), 100.39 (C-7), 90.90 (C-14), 83.90 (C-23), 83.78 (C-13), 80.84 (C-2), 70.61 (C-38), 48.95 (C-22), 46.81 (C-11), 44.67 (C-20), 29.83 (C-25), 29.44 (C-39), 29.43 (C-40), 29.27 (C-26), 28.83 (C-24), 27.39 (C-19), 25.73 (C-35), 25.14 (C-21), 21.58 (C-31), 20.72 (C-29), 18.14 (C-34).

The EIMS data of Product Gh-3272 show [M–H₂O]⁺ (2) at m/z 626 and a base peak at m/z 545 (100), and the HRFABMS data of Product Gh-3272 show a pseudomolecular ion peak [M–H₂O+H]⁺ at m/z 627.2961, indicating that Product Gh-3272 has a molecular formula of C₃₈H₄₄O₉, which has sixteen more mass units than the molecular formula of gambogic acid. As compared to gambogic acid, the unsaturation number of Product Gh-3272 remains unchanged.

The ¹H-NMR and ¹³C-NMR data of Product Gh-3272 show that: Product Gh-3272 has a C-2 side chain attached different from that of gambogic acid, namely, a 4-hydroxy-4-methyl-2-pentenyl group in lieu of the 4-methyl-3-pentenyl group in gambogic acid.

The ¹H-NMR and ¹³C-NMR data of Product Gh-3272 also reveal that Product Gh-3272 has an oxygen-bearing quaternary carbon (δ 70.61) and two coupled olefinic protons (δ 5.59 (1H, d, J=15.7 Hz) and δ 5.53 (1H, dt, J=15.6, 6.9 Hz)). In view of the coupling constant (J) of 15.7 Hz, the olefinic group is a trans double bond (i.e., in an E configuration).

The ¹H-¹H COSY data of Product Gh-3272 show that: δ 5.53 (1H, dt, J=15.6, 6.9 Hz) is coupled not only to δ 5.59 (1H, d, J=15.7 Hz), but also to two methylene protons (δ 2.36 (H₁-20) and δ 2.25 (H₂-20)), evidencing that a trans-disubstituted double bond is located at C-36 and C-37.

The HMBC data of Product Gh-3272 show that: the methylene protons (δ 2.25 (H₂-20) and δ 2.36 (H₁-20)) are correlated with δ 27.39 (C-19), δ 80.84 (C-2), δ 120.93 (C-36) and δ 142.05 (C-37), as well as an olefinic carbon (δ 123.91 (C-3)) in a pyran ring; δ 5.53 (H-36) is correlated with δ 44.67 (C-20), δ 70.61 (C-38) and δ 142.05 (C-37); and δ 5.59 (H-37) is correlated with δ 44.67 (C-20), δ 70.61 (C-38), δ 120.93 (C-36), δ 29.44 (C-39) and δ 29.43 (C-40), evidencing that the side chain attached to C-2 is a 4-hydroxy-4-methyl-2-pentenyl group.

The NOESY data of Product Gh-3272 show that: δ 7.52 (H-10) is correlated with δ 3.46 (H-11); δ 3.46 (H-11) is correlated with δ 2.29 (H₁-21) and δ 1.37 (H₂-21); δ 1.37 (H₂-21) is correlated with δ 2.49 (H-22); δ 2.49 (H-22) is correlated with a gem-dimethyl group (δ 1.67 (H-25) and δ 1.27 (H-24)); and δ 6.03 (H-27) is correlated with δ 1.70 (H-29), evidencing that the stereostructure of Product Gh-3272 in this part is identical to that of gambogic acid, i.e., in a 11S,13R,14S,22S configuration, which includes H-27 and carboxyl group (C-30) in a trans relationship, and a double bond $\Delta^{27,28}$ in a Z configuration. Besides, the olefinic proton (δ 5.53 (H-36)) is correlated not only with δ 5.59 (H-37) and the methylene protons (δ 2.36 (H₁-20) and δ 2.25 (H₂-20)), but also with the gem-dimethyl group (δ 1.16 (H-39 and H-40)), and another olefinic proton (δ 5.34 (H-3)) is correlated with δ 1.38 (H-19) and δ 2.25 (H₂-20). Since δ 1.38 (H-19) is correlated with δ 1.70 (H-29), C-2 is in an R configuration.

Based on the above information, Product Gh-3272 is identified to be a new compound having the following chemical structure:

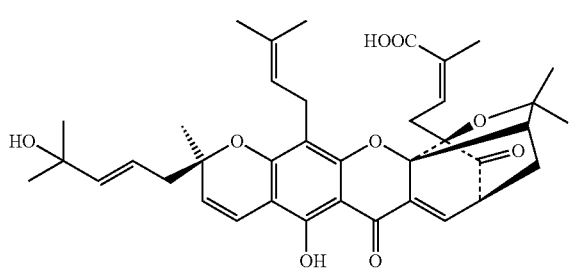

Product Gh-3272 is identified by the name "formoxanthone H" {IUPAC nomenclature: [2-butenoic acid, 2-methyl-4-[(1R,3aS,5S,11R,14aS)-3a,4,5,7-tetrahydro-8-hydroxy-3,3,11-trimethyl-13-(3-methyl-2-butenyl)-11-(4-hydroxy-4-methyl-2E-pentenyl)-7,15-dioxo-1,5-methano-1H,3H,11H-furo[3.4-g]pyrano[3.2-b]xanthen-1-yl]-,(2Z)-]}.

33. Product Gh-3332:

Product Gh-3332, which was purified from eluate 5 of fraction 1, was determined to have the following properties:

Yellow powder; mp 102-106° C.

EIMS m/z (relative intensity): 626 [M–H$_2$O]$^+$ (5), 575 (2), 545 (100), 499 (2), 471 (1), 389 (4), 347 (4), 271 (3), 245 (5), 215 (15), 189 (5), 147 (2), 105 (3), 69 (2); HRFABMS [M–H$_2$O+H]$^+$ m/z: 627.2966; calculated for C$_{38}$H$_{43}$O$_8$, 627.2958.

$^1$H-NMR (600 MHz, CDCl$_3$): δ 12.81 (1H, s, OH-6), 7.55 (1H, d, J=6.9 Hz, H-10), 6.83 (1H, dt, J=7.4, 1.3 Hz, H-27), 6.64 (1H, J=10.0 Hz, H-4), 5.68 (1H, d, J=8.4 Hz, H-37), 5.67 (1H, m, H-36), 5.44 (1H, d, J=10.0 Hz, H-3), 4.97 (1H, br t, J=6.2 Hz, H-32), 3.48 (1H, dd, J=6.8, 4.5 Hz, H-11), 3.28 (1H, dd, J=14.9, 8.9 Hz, H$_1$-31), 3.14 (1H, br dd, J=13.5, 3.4 Hz, H$_2$-31), 2.69 (1H, ddd, J=16.4, 6.2, 1.3 Hz, H$_1$-26), 2.52 (1H, d, J=9.3 Hz, H-22), 2.42 (1H, dd, J=14.3, 4.8 Hz, H$_1$-21), 2.32 (2H, m, H-20), 2.20 (1H, dd, J=16.3, 8.5 Hz, H$_2$-26), 1.71 (3H, s, H-34), 1.69 (3H, s, H-25), 1.61 (3H, s, H-35), 1.38 (3H, s, H-19), 1.37 (3H, s, H-39), 1.36 (1H, m, H$_2$-21), 1.33 (3H, s, H-40), 1.30 (3H, s, H-29), 1.27 (3H, s, H-24).

$^{13}$C-NMR (150 MHz, CDCl$_3$): δ 203.38 (C-12), 178.82 (C-8), 169.45 (C-30), 161.28 (C-18), 157.69 (C-16), 157.35 (C-6), 141.00 (C-37), 136.22 (C-27), 135.59 (C-10), 133.32 (C-9), 131.48 (C-33), 128.43 (C-28), 125.06 (C-3), 122.22 (C-32), 121.48 (C-36), 116.22 (C-4), 108.22 (C-17), 102.82 (C-5), 100.33 (C-7), 91.06 (C-14), 83.85 (C-23), 83.55 (C-13), 80.41 (C-2), 71.65 (C-38), 49.14 (C-22), 46.72 (C-11), 43.61 (C-20), 29.84 (C-25), 29.53 (C-39), 29.23 (C-40), 28.81 (C-24), 28.63 (C-26), 26.48 (C-19), 25.74 (C-35), 24.95 (C-21), 21.70 (C-31), 18.16 (C-34), 11.96 (C-29).

The EIMS data of Product Gh-3332 show [M–H$_2$O]$^+$ (5) at m/z 626 and a base peak at m/z 545 (100), and the HRFABMS data of Product Gh-3332 show a pseudomolecular ion peak [M–H$_2$O+H]$^+$ at m/z 627.2966, indicating that Product Gh-3332 has a molecular formula identical to that of product Gh-3272, C$_{38}$H$_{44}$O$_9$, which has 16 more mass units than the molecular formula of gambogic acid or isogambogic acid. As compared to gambogic acid, the unsaturation number of Product Gh-3332 remains unchanged.

The EIMS, $^1$H-NMR and $^{13}$C-NMR data of Product Gh-3332 are generally similar to those of Product Gh-3272, implying that Product Gh-3332 might be an isomer of Product Gh-3272. Besides, a comparison of the $^1$H-NMR data of a C-20 substituent group (δ 1.33 (3H, s, H-40), δ 1.37 (3H, s, H-39), δ 5.68 (1H, d, J=8.4 Hz, H-37) and δ 5.67 (1H, m, H-36)) of Product Gh-3332 with those of Product Gh-3272 reveals that $\Delta^{36,37}$ in Product Gh-3332 is in a Z configuration. Further, as compared to Product Gh-3272, in Product Gh-3332, H-27 has a significant downfield shift (δ$_H$ 6.83, Δδ=0.8), and C-29 is influenced by the γ-effect to have an upfield shift (δ$_C$ 11.96, Δδ=–8.76). As such, it is presumed that $\Delta^{27,28}$ in product Gh-3332 is in an E configuration.

Based on the above information, Product Gh-3332 is identified to be a new compound having the following chemical structure:

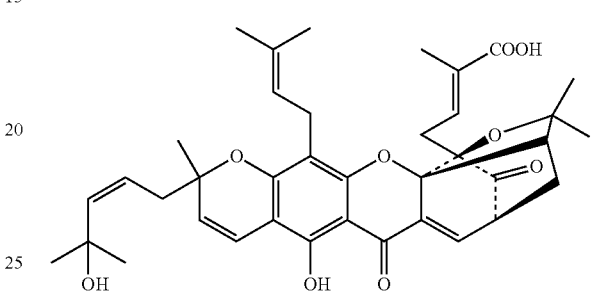

Product Gh-3332 is identified by the name "isoformoxanthone I" {IUPAC nomenclature: [2-butenoic acid, 2-methyl-4-[(1R,3aS,5S,14aS)-3a,4,5,7-tetrahydro-8-hydroxy-3,3,11-trimethyl-13-(3-methyl-2-butenyl)-11-(4-hydroxy-4-methyl-2Z-pentenyl)-7,15-dioxo-1H,3H,11H-furo[3.4-g]pyrano[3.2-b]xanthen-1-yl]-,(2E)-]}.

34. Product Gh-3261:

Product Gh-3261, which was purified from eluate 1 of fraction 1, was determined to have the following properties:

Yellow powder; mp 103-105° C.

EIMS m/z (relative intensity): 662 [M]$^+$ (15), 647 (5), 603 (2), 545 (100), 517 (12), 499 (2), 389 (4), 347 (3), 295 (1), 245 (3), 215 (6), 189 (2), 147 (1), 105 (2), 69 (3), 59 (3); HREIMS [M]$^+$ m/z: 662.3098; calculated for C$_{38}$H$_{46}$O$_{10}$, 662.3091.

$^1$H-NMR (600 MHz, CDCl$_3$): δ 12.73 (1H, s, OH-6), 7.49 (1H, d, J=7.0 Hz, H-10), 6.65 (1H, dd, J=10.2, 2.5 Hz, H-4), 5.54 (1H, br t, J=4.6 Hz, H-27), 5.36 (1H, d, J=10.3 Hz, H-3), 5.06 (1H, br s, H-32), 3.50 (1H, t, J=5.7 Hz, H-11), 3.39 (1H, m, H$_1$-26), 3.36 (1H, d, J=10.1 Hz, H-37), 3.27 (1H, dd, J=14.9, 7.4 Hz, H$_1$-31), 3.22 (1H, br dd, J=14.3, 4.7 Hz, H$_2$-31), 2.86 (1H, br d, J=14.1 Hz, H$_2$-26), 2.51 (1H, d, J=9.4 Hz, H-22), 2.33 (1H, dd, J=13.5, 4.7 Hz, H$_1$-21), 2.04 (1H, m, H$_1$-20), 1.74 (1H, m, H$_1$-36), 1.72 (3H, s, H-34), 1.68 (1H, m, H$_2$-20), 1.65 (3H, s, H-25), 1.64 (3H, s, H-35), 1.60 (3H, s, H-29), 1.459 (1H, m, H$_2$-36), 1.456 (3H, s, H-19), 1.39 (1H, dd, J=13.5, 9.6 Hz, H$_2$-21), 1.27 (3H, s, H-24), 1.21 (3H, s, H-39), 1.11 (3H, s, H-40).

$^{13}$C-NMR (150 MHz, CDCl$_3$): δ 203.34 (C-12), 179.20 (C-8), 168.78 (C-30), 161.13 (C-18), 157.75 (C-16), 157.43 (C-6), 136.34 (C-27), 134.74 (C-10), 133.91 (C-9), 131.41 (C-33), 128.56 (C-28), 124.18 (C-3), 122.33 (C-32), 116.18 (C-4), 107.80 (C-17), 102.49 (C-5), 100.63 (C-7), 90.57 (C-14), 84.03 (C-13), 83.64 (C-23), 81.24 (C-2), 78.23 (C-37), 73.70 (C-38), 49.01 (C-22), 47.02 (C-11), 38.73 (C-20), 29.92 (C-25), 29.87 (C-26), 29.05 (C-24), 27.88 (C-19), 26.70 (C-39), 25.70 (C-35), 25.28 (C-36), 25.25 (C-21), 24.28 (C-40), 21.71 (C-31), 20.85 (C-29), 18.22 (C-34).

The EIMS data of Product Gh-3261 show a molecular ion peak [M]⁺ at m/z 662 and a base peak at m/z 545 (100), and the HREIMS data of Product Gh-3261 show [M]⁺ at m/z 662.3098, indicating that Product Gh-3261 has a molecular formula of $C_{38}H_{46}O_{10}$, which has thirty-four more mass units than the molecular formula of gambogic acid.

The ¹H-NMR, ¹³C-NMR and HMQC data of Product Gh-3261 show that Product Gh-3261 has a C-2 side chain different from that of gambogic acid, namely, a 3,4-dihydroxy-4-methylpentyl group in lieu of the 4-methyl-3-pentenyl group in gambogic acid. Besides, the ¹H-NMR and ¹³C-NMR data of Product Gh-3261 reveal that Product Gh-3261 has a secondary hydroxy group (δ 3.36 (1H, d, J=10.1 Hz) and δ 78.23) and an oxygen-bearing quaternary carbon (δ 73.70).

The ¹H-¹H COSY data of Product Gh-3261 show that: a hydroxymethine proton (δ 3.36 (1H, d, J=10.1 Hz)) is coupled to δ 1.459 (1H, m); δ 1.459 (1H, m) is coupled to δ 2.04 (1H, m, H₁-20); and four protons of two adjacent methylene groups at C-20 and C-36 (δ 2.04 (H₁-20), δ 1.68 (H₂-20) and δ 38.73 (C-20); and δ 1.74 (H₁-36), δ 1.459 (H₂-36) and δ 25.28 (C-36)] are coupled to each other, indicating that the hydroxymethine proton is H-37. As such, it can be known that a secondary hydroxy group is attached to C-37 (δ 78.23); a tertiary hydroxy group is attached to C-38 (δ 73.70); and C-39 (δ 26.70) and C-40 (δ 24.28) are tertiary methyl groups.

The HMBC data of Product Gh-3261 show that: the hydroxymethine proton (δ 3.36 (H-37)] is correlated with δ 38.73 (C-20); both δ 2.04 (H₁-20) and δ 1.68 (H₂-20) are correlated with δ 25.28 (C-36), δ 81.24 (C-2) and δ 124.18 (C-3); δ 5.36 (H-3) is correlated with δ 102.49 (C-5), δ 81.24 (C-2) and δ 27.88 (C-19); δ 1.456 (H-19) is correlated with δ 81.24 (C-2), δ 124.18 (C-3), δ 116.18 (C-4) and δ 38.73 (C-20); δ 1.21 (H-39) is correlated with δ 8.23 (C-37), δ 73.70 (C-38) and δ 24.28 (C-40); and δ 1.11 (H-40) is correlated with δ 78.23 (C-37), δ 73.70 (C-38) and δ 26.70 (C-39), evidencing that the side chain attached to C-2 is a 3,4-dihydroxy-4-methylpentyl group.

The NOESY data of Product Gh-3261 show that: δ 7.49 (H-10) is correlated with δ 3.50 (H-11); δ 3.50 (H-11) is correlated with δ 2.33 (H₁-21) and δ 1.39 (H₂-21); δ 1.39 (H₂-21) is correlated with δ 2.51 (H-22) and δ 1.27 (H-24); δ 2.51 (H-22) is correlated with δ 1.65 (H-25); and δ 5.54 (H-27) is correlated with δ 1.60 (H-29), evidencing that the stereostructure of Product Gh-3261 in this part is identical to that of gambogic acid, i.e., in a 11S,13R,14S,22S configuration, which includes H-27 and carboxyl group (C-30) in a trans relationship, and a double bond $Δ^{27,28}$ in a Z configuration. In addition, since δ 3.36 (H-37) is correlated with δ 1.21 (H-39) and δ 1.11 (H-40), while δ 1.456 (H-19) is correlated with δ 1.60 (H-29), C-2 is in an R configuration.

Based on the above information, Product Gh-3261 is identified to be a new compound having the following chemical structure:

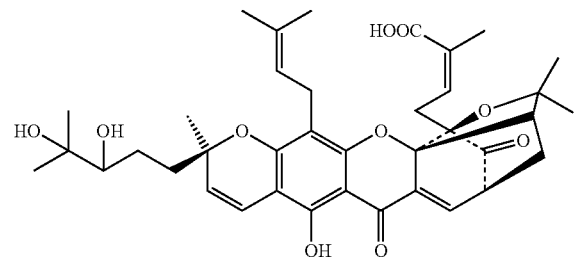

Product Gh-3261 is identified by the name "formoxanthone J" {IUPAC nomenclature: [2-butenoic acid, 2-methyl-4-[(1R,3aS,5S,11R,14aS)-3a,4,5,7-tetrahydro-8-hydroxy-3,3,11-trimethyl-13-(3-methyl-2-butenyl)-11-(3,4-dihydroxy-4-methylpentyl)-7,15-dioxo-1,5-methano-1H,3H,11H-furo[3.4-g]pyrano[3.2-b]xanthen-1-yl]-,(2Z)-]}.

35. Product Gh-3271:

Product Gh-3271, which was purified from eluate 2 of fraction 1, was determined to have the following properties:

Yellow powder; mp 99-102° C.

EIMS m/z (relative intensity): 662 [M]⁺ (14), 644 (5), 603 (4), 545 (100), 517 (15), 499 (3), 419 (4), 389 (6), 347 (5), 283 (5), 245 (6), 215 (11), 213 (5), 189 (5), 147 (4), 129 (4), 117 (5), 105 (8), 91 (7), 85.9 (12), 83.9 (19), 69 (11), 59 (8), 57 (11), 55 (11); HREIMS [M]⁺ m/z: 662.3097; calculated for $C_{38}H_{46}O_{10}$, 662.3091.

¹H-NMR (600 MHz, CDCl₃): δ 12.75 (1H, s, OH-6), 7.50 (1H, d, J=7.0 Hz, H-10), 6.65 (1H, d, J=10.0 Hz, H-4), 5.46 (1H, d, J=10.0 Hz, H-3), 5.39 (1H, ddd, J=10.7, 3.9, 1.4 Hz, H-27), 5.08 (1H, dd, J=7.2, 5.9 Hz, H-32), 3.50 (1H, m, H-11), 3.49 (1H, m, H₁-26), 3.38 (1H, dd, J=10.5, 1.9 Hz, H-37), 3.28 (1H, br dd, J=15.1, 5.6 Hz, H₁-31), 3.23 (1H, dd, J=15.0, 7.4 Hz, H₂-31), 2.83 (1H, ddd, J=15.8, 3.9, 2.4 Hz, H₂-26), 2.50 (1H, d, J=9.4 Hz, H-22), 2.34 (1H, dd, J=13.5, 4.7 Hz, H₁-21), 2.05 (1H, m, H₁-20), 1.71 (3H, s, H-34), 1.68 (1H, m, H₁-36), 1.64 (3H, s, H-35), 1.63 (3H, s, H-25), 1.62 (1H, m, H₂-20), 1.58 (3H, s, H-29), 1.52 (1H, m, H₂-36), 1.44 (3H, s, H-19), 1.37 (1H, dd, J=13.5, 9.5 Hz, H₂-21), 1.27 (3H, s, H-24), 1.18 (6H, s, H-39, H-40).

¹³C-NMR (150 MHz, CDCl₃): δ 203.26 (C-12), 179.32 (C-8), 168.56 (C-30), 160.44 (C-18), 157.89 (C-16), 157.53 (C-6), 135.74 (C-27), 134.69 (C-10), 133.85 (C-9), 131.67 (C-33), 129.00 (C-28), 125.28 (C-3), 122.40 (C-32), 116.13 (C-4), 108.14 (C-17), 102.95 (C-5), 100.68 (C-7), 90.47 (C-14), 84.20 (C-13), 83.57 (C-23), 80.56 (C-2), 78.09 (C-37), 73.63 (C-38), 49.07 (C-22), 47.05 (C-11), 36.88 (C-20), 29.99 (C-26), 29.86 (C-25), 29.11 (C-24), 26.39 (C-19), 25.89 (C-39), 25.66 (C-35), 25.56 (C-36), 25.22 (C-21), 23.40 (C-40), 21.76 (C-31), 20.81 (C-29), 18.07 (C-34).

The EIMS data of Product Gh-3271 show a molecular ion peak [M]⁺ at m/z 662 and a base peak at m/z 545 (100), and the HREIMS data of product Gh-3271 show [M]⁺ at m/z 662.3097, indicating that Product Gh-3271 has a molecular formula of $C_{38}H_{46}O_{10}$, which has thirty-four more mass units than the molecular formula of gambogic acid.

The ¹H-NMR, ¹³C-NMR and HMQC data of Product Gh-3271 show that Product Gh-3271 has a C-2 side chain different from that of gambogic acid, namely, a 3,4-dihydroxy-4-methylpentyl group in lieu of the 4-methyl-3-pentenyl in gambogic acid. Besides, the ¹H-NMR and ¹³C-NMR data of Product Gh-3271 show that Product Gh-3271 has a secondary hydroxy group (δ 3.38 (1H, dd, J=10.5, 1.9 Hz) and δ 78.09) and an oxygen-bearing quaternary carbon (δ 73.63).

The ¹H-¹H COSY data of Product Gh-3271 show that: a hydroxymethine proton (δ 3.38 (1H, dd, J=10.5, 1.9 Hz)) is coupled to δ 1.52 (1H, m); δ 1.52 (1H, m) is coupled to δ 2.05 (1H, m, H₁-20); and two adjacent methylene protons (δ 2.05 (H₁-20), δ 1.62 (H₂-20), δ 1.68 (H₁-36), and δ 1.52 (H₂-36)) are coupled to each other, evidencing that the hydroxymethine proton is H-37.

The HMQC data of Product Gh-3271 show that: δ 36.88 (C-20), δ 25.56 (C-36), and δ 73.63 (C-38), evidencing that the secondary hydroxy group is attached to C-37, and a tertiary hydroxy group is attached to C-38.

The HMBC data of Product Gh-3271 show that: δ 3.38 (H-37) is correlated with δ 36.88 (C-20); both δ 2.05 ($H_1$-20) and δ 1.62 ($H_2$-20) are correlated with δ 25.56 (C-36), δ 78.09 (C-37), δ 80.56 (C-2), δ 125.28 (C-3) and δ 26.39 (C-19); δ 5.46 (H-3) is correlated with δ 80.56 (C-2), δ 26.39 (C-19) and δ 102.95 (C-5); δ 1.44 (H-19) is correlated with δ 80.56 (C-2), δ 125.28 (C-3), δ 116.13 (C-4) and δ 160.44 (C-18); and δ 1.18 (H-39 and H-40) is correlated with δ 78.09 (C-37) and δ 73.63 (C-38), evidencing that the side chain attached to C-2 is a 3,4-dihydroxy-4-methylpentyl group.

The NOESY data of Product Gh-3271 show that: δ 7.50 (H-10) is correlated with δ 3.50 (H-11); δ 3.50 (H-11) is correlated with δ 2.34 ($H_1$-21) and δ 1.37 ($H_2$-21); δ 1.37 ($H_2$-21) is correlated with δ 2.50 (H-22) and δ 1.27 (H-24); δ 2.50 (H-22) is correlated with δ 1.63 (H-25); and δ 5.39 (H-27) is correlated with δ 1.58 (H-29), evidencing that the stereostructure of Product Gh-3271 in this part is identical to that of gambogic acid, i.e., in a 11S,13R,14S,22S configuration, which includes H-27 and carboxyl group (C-30) in a trans relationship, and a double bond $\Delta^{27,28}$ in a Z configuration. In addition, since δ 3.38 (H-37) is correlated with δ 1.18 (H-39 and H-40), and δ 2.05 ($H_1$-20) is correlated with δ 1.58 (H-29), C-2 is in an S configuration.

Based on the above information, Product Gh-3271 is identified to be a new compound having the following chemical structure:

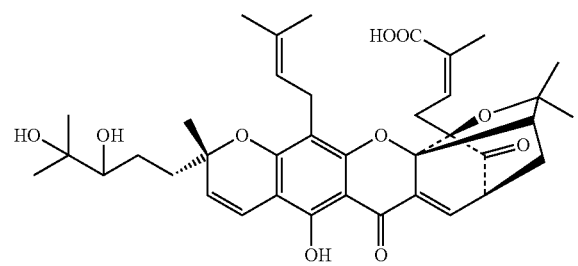

Product Gh-3271 is identified by the name "epiformoxanthone J" {IUPAC nomenclature: [2-butenoic acid, 2-methyl-4-[(1R,3aS,5S,11S,14aS)-3a,4,5,7-tetrahydro-8-hydroxy-3,3,11-trimethyl-13-(3-methyl-2-butenyl)-11-(3,4-dihydroxy-4-methylpentyl)-7,15-dioxo-1,5-methano-1H, 3H,11H-furo[3.4-g]pyrano[3.2-b]xanthen-1-yl]-,(2Z)-]}.

Conclusion:

According to the experimental results obtained above, the thirty-five products purified from fractions 1-3 are found to include 17 new compounds and 18 known compounds, as summarized in the following Table 4. Inasmuch as Products Gh-47, Gh-631, Gh-4601, Gh-4602 and Gh-2301 are found to be known compounds, the in vitro anti-cancer activities of which had been tested in U.S. Pat. No. 7,138,428 B2, these five products are not tested in the following pharmacological experiments.

TABLE 4

Thirty-five products purified from fractions 1-3

|  | Product no. | Nomenclature |
|---|---|---|
| New compounds | Gh-2607-B | Formoxanthone B |
|  | Gh-2607-1A | Epiformoxanthone B |
|  | Gh-2508 | β-Gambogellic acid |
|  | Gh-2507 | β-Epigambogellic acid |

TABLE 4-continued

Thirty-five products purified from fractions 1-3

|  | Product no. | Nomenclature |
|---|---|---|
|  | Gh-1631 | Formoxanthone C |
|  | Gh-1050 | 3α-Hydroxygambogellic acid |
|  | Gh-3291 | Formoxanthone D |
|  | Gh-3352 | Formoxanthone E |
|  | Gh-3351 | Epiformoxanthone E |
|  | Gh-1052 | Formoxanthone F |
|  | Gh-1036 | Epiformoxanthone F |
|  | Gh-3353 | Formoxanthone G |
|  | Gh-3311 | Epiformoxanthone G |
|  | Gh-3272 | Formoxanthone H |
|  | Gh-3332 | Isoformoxanthone I |
|  | Gh-3261 | Formoxanthone J |
|  | Gh-3271 | Epiformoxanthone J |
| Known compounds | Gh-47 | Isomorellic acid |
|  | Gh-631 | Formoxanthone A |
|  | Gh-4601 | Isomorellinol |
|  | Gh-4602 | Morellic acid |
|  | Gh-2301 | Desoxymorellin |
|  | Gh-4301 | Desoxygambogenin |
|  | Gh-2605 | Gambogic acid |
|  | Gh-2606 | Eepigambogic acid |
|  | Gh-1641 | Isogambogic acid |
|  | Gh-1642 | Epiisogambogic acid |
|  | Gh-2603-2 | Gambogellic acid |
|  | Gh-2603-1 | Epigambogellic acid |
|  | Gh-2501 | Isomorellin |
|  | Gh-2505 | Gambogenic acid |
|  | Gh-2642 | Isogambogenic acid |
|  | Gh-1601-A | 30-Hydroxygambogic acid |
|  | Gh-1602 | 30-Hydroxyepigambogic acid |
|  | Gh-2641-1 | Neogambogic acid |

Example 4

Pharmacological Experiment of the Purified Compounds Obtained from the Product TSB-14

In order to explore the possible biological activities of the purified products obtained in the above Example 2 (excluding Products Gh-47, Gh-631, Gh-4601, Gh-4602 and Gh-2301), the following pharmacological experiment was performed by the MDS Pharma Services.

In Vitro Anti-Cancer Test

The in vitro anti-cancer test was primarily used to detect the effect of a candidate drug on cancer cell proliferation. The working principle involved therein is the ability of viable cells to shift alamarBlue (AbD Serotec, UK) from its originally non-fluorescent oxidized state (non-fluorescent, blue) to a reduced form (fluorescent, red) having fluorescence via metabolic reaction. According to the fluorescent data result generated by the alamarBlue reagent thus obtained, the proliferation of the viable cells and cell activity can be quantified for detection.

In the in vitro anti-cancer tests, a candidate drug was tested at 5 different concentrations of 0.01, 0.1, 1, 10, and 100 μg/ml, and six human cancer cell lines and a normal human cell line were used (see Table 5). In addition, 40% dimethylsulfoxide (DMSO) was used as a normal control, and mitomycin was used as a positive control.

TABLE 5

Cell lines used in the in vitro anti-cancer tests

| Cell line | Source |
|---|---|
| Human breast adenocarcinoma cell MCF7 | ATCC HTB-22 |
| Human colon adenocarcinoma cell HT-29 | ATCC HTB-38 |
| Human promyelocytic leukemia cell HL-60 | ATCC CCL-240 |
| Human hepatocellular carcinoma cell HepG2 | ATCC HB-8065 |
| Human lung carcinoma cell A549 | ATCC CCL-185 |
| Human histocytic lymphoma cell U937 | ATCC CRL-1593 |
| Human umbilical venal epithelial cell (HUVEC) | ATCC CRL-1730 |

According to the experimental reports provided by the MDS Pharma Services, $IC_{50}$ (50% inhibition concentration) and $LC_{50}$ (50% lethal concentration) of the thirty purified products obtained in the above Example 2 are shown in Tables 6-7, respectively.

TABLE 6

$IC_{50}$ (μg/mL) of thirty purified products obtained in Example 2 with respect to cancer cells

| Tested product | MCF-7 | HT-29 | HL-60 | HepG2 | A549 | U937 | HUVEC |
|---|---|---|---|---|---|---|---|
| Gh-3353 | 2.4 | 5.0 | 1.3 | 5.3 | 2.6 | 4.8 | 5.5 |
| Gh-3271 | 0.16 | 1.8 | 3.0 | 0.46 | 0.25 | 0.11 | 0.42 |
| Gh-3311 | 8.0 | 7.9 | 1.4 | 7.9 | 5.0 | 1.9 | 4.0 |
| Gh-3261 | 0.36 | 1.1 | 1.9 | 1.0 | 0.19 | 0.11 | 0.29 |
| Gh-3351 | 0.99 | 1.9 | 11.7 | 2.9 | 0.77 | 0.24 | 0.11 |
| Gh-3272 | 0.73 | 0.36 | 1.7 | 1.2 | 1.7 | 0.16 | 0.12 |
| Gh-3332 | 0.87 | 0.85 | 11.8 | 6.7 | 1.3 | 0.23 | 0.11 |
| Gh-3291 | 0.45 | 0.081 | 4.5 | 0.65 | 0.62 | 0.22 | 0.34 |
| Gh-2507 | 0.19 | 1.6 | 0.20 | 1.7 | 0.13 | 0.45 | 0.41 |
| Gh-2508 | 0.087 | 1.8 | 0.28 | 1.9 | 0.16 | 0.28 | 0.52 |
| Gh-1050 | 0.14 | 4.8 | 0.17 | 1.1 | 0.13 | 0.21 | 0.78 |
| Gh-1631 | 0.14 | 6.1 | 0.19 | 0.85 | 0.14 | 0.18 | 0.58 |
| Gh-2641-1 | 0.20 | 2.6 | 0.18 | 1.7 | 0.15 | 0.26 | 0.54 |
| Gh-1036 | 0.35 | 1.4 | 0.45 | 0.88 | 0.22 | 0.29 | 0.46 |
| Gh-1052 | 0.52 | 1.6 | 0.23 | 1.2 | 0.46 | 0.22 | 0.47 |
| Mitomycin (μM) | 0.79 | 0.099 | 0.13 | 0.47 | 0.35 | 0.18 | 0.37 |
| Gh-2505 | 1.9 | 2.1 | 0.75 | 2.1 | 0.62 | 1.1 | 0.28 |
| Gh-2501 | 1.3 | 2.1 | 1.0 | 2.2 | 0.61 | 0.90 | 0.26 |
| Mitomycin (μM) | 0.069 | 0.39 | 0.048 | 0.053 | 0.11 | 0.050 | 0.14 |
| Gh-4301 | 19 | 13 | 3.5 | 12 | 0.51 | 11 | 0.29 |
| Mitomycin (μM) | 0.089 | 0.50 | 0.078 | 0.069 | 0.097 | 0.059 | 0.075 |
| Gh-2603-1 | 2.2 | 1.6 | 1.0 | 1.0 | 0.036 | 1.3 | 0.26 |
| Gh-2603-2 | 2.2 | 1.4 | 0.93 | 0.65 | 0.20 | 1.5 | 0.14 |
| Gh-2605 | 4.4 | 0.18 | 0.17 | 0.23 | 0.12 | 0.76 | 0.098 |
| Gh-2606 | 1.3 | 0.39 | 0.66 | 0.38 | 0.10 | 0.41 | 0.11 |
| Gh-2607-B + Gh-2607-1A | 1.4 | 0.94 | 0.90 | 1.1 | 0.091 | 0.84 | 0.15 |
| Mitomycin (μM) | 0.15 | 0.49 | 0.098 | 0.11 | 0.099 | 0.072 | 0.12 |
| Gh-1641 | 1.7 | 1.4 | 8.0 | 0.86 | 0.47 | 9.4 | 0.18 |
| Gh-1642 | 2.4 | 1.9 | 6.0 | 1.1 | 0.51 | 8.8 | 0.18 |
| Mitomycin (μM) | 0.080 | 0.51 | 0.062 | 0.075 | 0.15 | 0.098 | 0.10 |
| Gh-2642 | 3.0 | 12 | 9.0 | 11 | 1.5 | 1.3 | 2.4 |
| Mitomycin (μM) | 0.13 | 0.57 | 0.12 | 0.062 | 0.24 | 0.17 | 0.13 |
| Gh-1602 | 0.27 | 0.94 | 1.0 | 1.3 | 0.40 | 0.14 | 0.25 |
| Mitomycin (μM) | 0.079 | 0.37 | 0.20 | 0.073 | 0.21 | 0.19 | 0.088 |
| Gh-2607-B | 0.10 | 0.30 | 0.13 | 0.31 | 0.10 | 0.10 | 0.07 |
| Gh-2607-1A | 0.12 | 0.24 | 0.49 | 0.43 | 0.19 | 0.15 | 0.43 |
| Gh-1601-A | 0.72 | 0.17 | 0.56 | 1.3 | 0.11 | 0.09 | 0.19 |
| Gh-3352 | 0.075 | 0.18 | 0.26 | 0.16 | 0.18 | 0.11 | 0.084 |
| Mitomycin (μM) | 0.15 | 0.11 | 0.24 | 0.21 | 0.098 | 0.18 | 0.15 |

TABLE 7

$LC_{50}$ (μg/mL) of thirty purified products obtained in Example 2 with respect to cancer cells

| Tested product | MCF-7 | HT-29 | HL-60 | HepG2 | A549 | U937 | HUVEC |
|---|---|---|---|---|---|---|---|
| Gh-3353 | 9.6 | 20.8 | 2.4 | 35.5 | 8.2 | 14.6 | 8.4 |
| Gh-3271 | 0.62 | 5.8 | 17.1 | 4.6 | 0.51 | 0.35 | 1.5 |
| Gh-3311 | 14.0 | 38.0 | 2.2 | 25.6 | 21.2 | 5.4 | 13.9 |
| Gh-3261 | 2.8 | 3.9 | 7.0 | 2.8 | 0.50 | 0.31 | 1.4 |
| Gh-3351 | 3.8 | 72.6 | 22.1 | 31.2 | 3.4 | 0.62 | 3.3 |
| Gh-3272 | 2.8 | 6.6 | 5.1 | 3.7 | 4.7 | 0.43 | 2.5 |

TABLE 7-continued

LC$_{50}$ (μg/mL) of thirty purified products obtained in Example 2 with respect to cancer cells

| Tested product | Cell line | | | | | | |
|---|---|---|---|---|---|---|---|
| | MCF-7 | HT-29 | HL-60 | HepG2 | A549 | U937 | HUVEC |
| Gh-3332 | 3.3 | 73.8 | 30.5 | 19.6 | 4.6 | 1.4 | 3.3 |
| Gh-3291 | 2.8 | 4.7 | 30.0 | 8.7 | 3.3 | 0.61 | 1.4 |
| Gh-2507 | 2.2 | 8.6 | 5.3 | 7.1 | 0.53 | 2.7 | 21.0 |
| Gh-2508 | 1.7 | 5.5 | 6.6 | 5.9 | 0.46 | 2.2 | 5.4 |
| Gh-1050 | 1.0 | 7.7 | 7.0 | 3.8 | 0.74 | 2.3 | 3.4 |
| Gh-1631 | 0.87 | 8.3 | 4.1 | 3.7 | 0.20 | 0.86 | 2.3 |
| Gh-2641-1 | 3.5 | 6.8 | 4.5 | 4.6 | 0.22 | 1.0 | 4.3 |
| Gh-1036 | 3.8 | 12.0 | 3.1 | 8.6 | 0.52 | 0.81 | 4.8 |
| Gh-1052 | 2.4 | 5.7 | 3.4 | 4.0 | 2.5 | 0.69 | 3.1 |
| Mitomycin (μM) | >10 | 8.9 | 1.3 | 4.7 | 4.0 | 0.75 | 8.3 |
| Gh-2505 | 19 | 4.4 | 7.2 | 6.5 | 12 | 3.7 | 2.3 |
| Gh-2501 | 3.7 | 4.0 | 4.0 | 4.5 | 2.1 | 3.1 | 1.8 |
| Mitomycin (μM) | 6.4 | 5.6 | 0.81 | 1.8 | 2.0 | 1.1 | 1.4 |
| Gh-4301 | 56 | 42 | >100 | 51 | 6.2 | >100 | 1.3 |
| Mitomycin (μM) | 5.8 | 7.8 | 2.5 | 2.6 | 2.1 | 3.3 | 8.5 |
| Gh-2603-1 | 4.2 | 3.7 | 2.9 | 3.3 | 0.34 | 3.1 | 1.7 |
| Gh-2603-2 | 4.2 | 3.9 | 2.4 | 3.5 | 0.47 | 3.6 | 1.7 |
| Gh-2605 | 5.9 | 0.61 | 2.9 | 3.5 | 0.37 | 2.9 | 1.6 |
| Gh-2606 | 1.6 | 2.0 | 2.4 | 3.0 | 0.31 | 3.1 | 1.4 |
| Gh-2607-B + Gh-2607-1A | 2.2 | 2.1 | 2.7 | 2.5 | 0.51 | 2.7 | 1.4 |
| Mitomycin (μM) | 1.8 | 9.3 | 1.3 | 1.3 | 1.9 | 2.0 | 6.6 |
| Gh-1641 | 33 | 4.4 | 32 | 4.5 | 3.0 | 36 | 1.3 |
| Gh-1642 | 29 | 4.8 | 35 | 5.3 | 2.8 | 33 | 1.3 |
| Mitomycin (μM) | 5.8 | 8.5 | 1.2 | 2.3 | 3.6 | 1.9 | 2.4 |
| Gh-2642 | 10 | 42 | 32 | 29 | 4.6 | 4.1 | 11 |
| Mitomycin (μM) | >10 | >10 | 2.3 | 1.6 | 4.5 | 0.87 | 2.4 |
| Gh-1602 | 4.0 | 4.2 | 3.3 | 3.5 | 3.7 | 0.69 | 0.94 |
| Mitomycin (μM) | >10 | >10 | 1.8 | 2.4 | 5.3 | 0.82 | 1.7 |
| Gh-2607-B | 0.68 | 1.0 | 3.1 | 4.0 | 0.33 | 0.25 | 1.6 |
| Gh-2607-1A | 1.5 | 0.84 | 2.6 | 3.9 | 0.45 | 0.37 | 1.5 |
| Gh-1601-A | 4.4 | 0.77 | 3.0 | 4.1 | 6.6 | 0.28 | 5.4 |
| GH-3352 | 1.8 | 0.68 | 0.93 | 2.0 | 0.99 | 0.26 | 0.85 |
| Mitomycin (μM) | 17 | 22 | 0.89 | 5.2 | 4.4 | 0.85 | 1.8 |

It can be known from the results shown in Tables 6-7 that the seventeen new compounds obtained in the above Example 2 all have significant effects in inhibiting the growth of tumor/cancer cells and killing tumor/cancer cells. Therefore, the seventeen new compounds obtained in the above Example 2 all have high potentials for serving as anti-cancer drugs.

All patents and literature references cited in the present specification are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

I claim:

1. A method of inhibiting the growth of tumor/cancer cells wherein the tumor/cancer cells comprise one or more of: human breast adenocarcinoma cells, human colon adenocarcinoma cells, human promyelocytic leukemia cells, human hepatocellular carcinoma cells, human lung carcinoma cells, or human histocytic lymphoma cells, the method comprising contacting the cells with one or more compounds selected from the group consisting of:

(1) a compound of the formula:

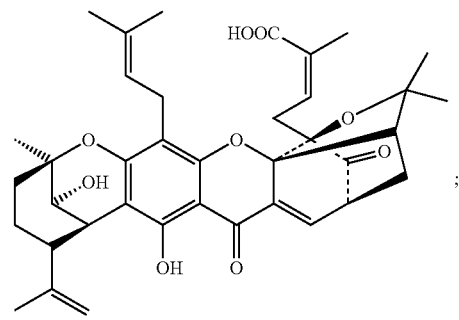

;

(2) a compound of the formula:

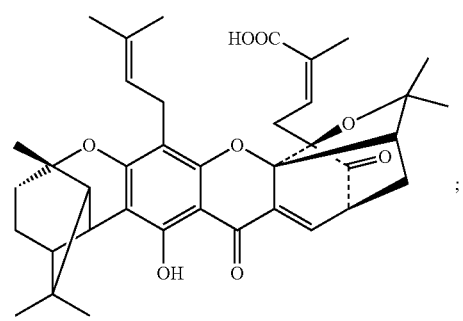

;

(3) a compound of the formula:
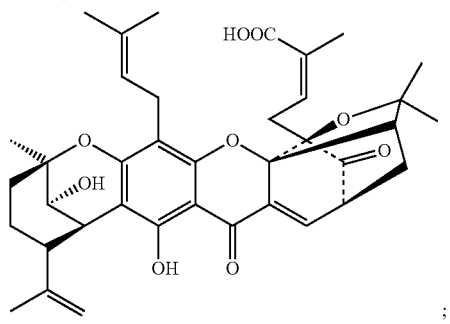
;
(4) a compound of the formula:
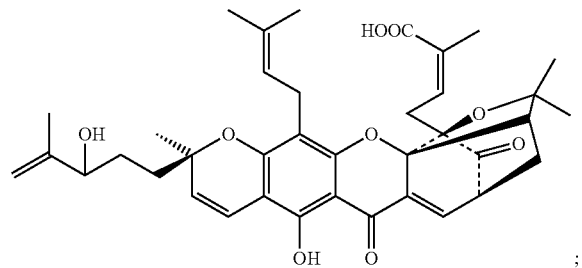
;
(5) a compound of the formula:
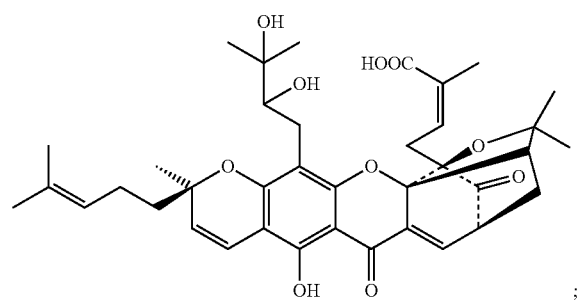
;
(6) a compound of the formula:
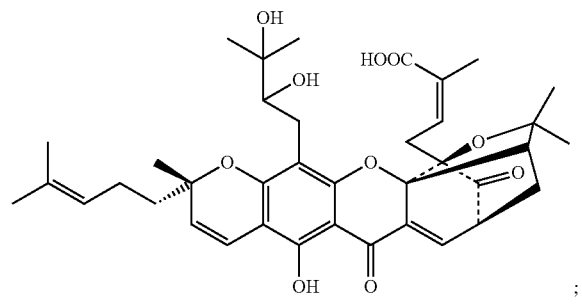
;
(7) a compound of the formula:
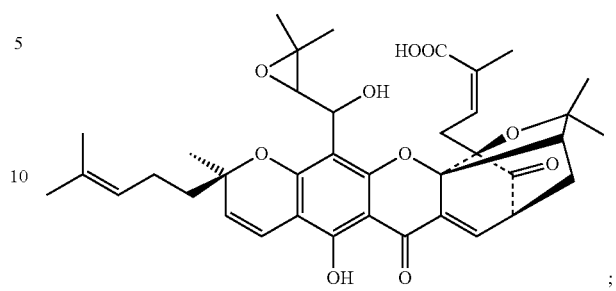
;
(8) a compound of the formula:
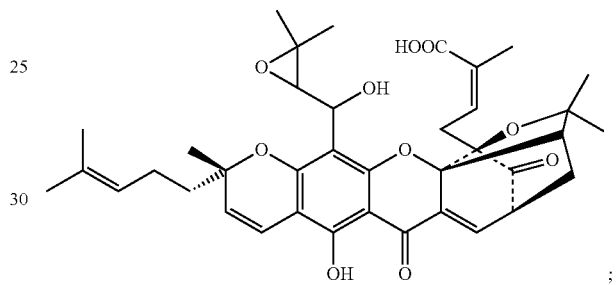
;
and,
(9) a compound of the formula:
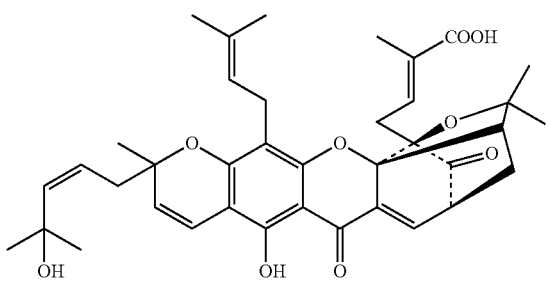
.
* * * * *